US010194972B2

(12) United States Patent
Yates et al.

(10) Patent No.: US 10,194,972 B2
(45) Date of Patent: Feb. 5, 2019

(54) MANAGING TISSUE TREATMENT

(71) Applicant: Ethicon Endo-Surgery, Inc., Cincinnati, OH (US)

(72) Inventors: David C. Yates, West Chester, OH (US); Eitan T. Wiener, Cincinnati, OH (US); Mark A. Davison, Mason, OH (US)

(73) Assignee: Ethicon LLC, Guaynabo, PR (US)

( * ) Notice: Subject to any disclaimer, the term of this patent is extended or adjusted under 35 U.S.C. 154(b) by 1001 days.

(21) Appl. No.: 14/469,093

(22) Filed: Aug. 26, 2014

(65) Prior Publication Data
US 2016/0058492 A1 Mar. 3, 2016

(51) Int. Cl.
A61B 18/12 (2006.01)
A61B 18/00 (2006.01)
A61B 18/14 (2006.01)
A61B 18/10 (2006.01)
(Continued)

(52) U.S. Cl.
CPC ...... A61B 18/1206 (2013.01); A61B 18/1233 (2013.01); A61B 18/085 (2013.01); A61B 18/10 (2013.01); A61B 18/1445 (2013.01); A61B 2018/00607 (2013.01); A61B 2018/00642 (2013.01); A61B 2018/00648 (2013.01); A61B 2018/00678 (2013.01); A61B 2018/00702 (2013.01); A61B 2018/00779 (2013.01);
(Continued)

(58) Field of Classification Search
CPC ... A61B 18/085; A61B 18/10; A61B 18/1206; A61B 18/1233

USPC .......................................................... 606/34
See application file for complete search history.

(56) References Cited

U.S. PATENT DOCUMENTS 2,366,274 A 1/1945 Luth et al.
2,458,152 A 1/1949 Eakins
2,510,693 A 6/1950 Green
(Continued)

FOREIGN PATENT DOCUMENTS

CN 2868227 Y 2/2007
CN 102834069 A 12/2012
(Continued)

OTHER PUBLICATIONS

International Search Report for Application No. PCT/US2015/044206, dated Nov. 4, 2015 (4 pages).
(Continued)

*Primary Examiner* — Christopher A Flory

(57) ABSTRACT

Various embodiments are directed to systems and methods for providing a drive signal to a surgical device for treating tissue. A surgical generator may deliver the drive signal according to a first composite load curve. The surgical generator may receive a first tissue measurement indicating a property of the tissue at a first time during the delivery of the drive signal, receive a second tissue measurement indicating the property of the tissue at a second time during the delivery of the drive signal after the first time, and based on the first and second tissue measurements, determine a difference in the property of the tissue between the first time and the second time. When the difference in the property of the tissue exceeds a difference threshold, the generator may deliver the drive signal according to a second composite load curve that is more aggressive than the first composite load curve.

14 Claims, 33 Drawing Sheets

(51) Int. Cl.
*A61B 18/08* (2006.01)
*A61N 7/02* (2006.01)
(52) U.S. Cl.
CPC ............. *A61B 2018/00791* (2013.01); *A61B 2018/00875* (2013.01); *A61N 2007/025* (2013.01)

(56) References Cited

U.S. PATENT DOCUMENTS

| | | | |
|---|---|---|---|
| 2,867,039 A | 1/1959 | Zach | |
| 3,166,971 A | 1/1965 | Stoecker | |
| 3,525,912 A | 8/1970 | Wallin | |
| 3,580,841 A | 5/1971 | Cadotte et al. | |
| 3,703,651 A | 11/1972 | Blowers | |
| 3,777,760 A | 12/1973 | Essner | |
| 4,005,714 A | 2/1977 | Hiltebrandt | |
| 4,034,762 A | 7/1977 | Cosens et al. | |
| 4,058,126 A | 11/1977 | Leveen | |
| 4,203,430 A | 5/1980 | Takahashi | |
| 4,220,154 A | 9/1980 | Semm | |
| 4,237,441 A | 12/1980 | van Konynenburg et al. | |
| 4,281,785 A | 8/1981 | Brooks | |
| 4,304,987 A | 12/1981 | van Konynenburg | |
| 4,314,559 A | 2/1982 | Allen | |
| 4,463,759 A | 8/1984 | Garito et al. | |
| 4,492,231 A | 1/1985 | Auth | |
| 4,535,773 A | 8/1985 | Yoon | |
| 4,545,926 A | 10/1985 | Fouts, Jr. et al. | |
| 4,549,147 A * | 10/1985 | Kondo | G05F 1/62 330/207 P |
| 4,550,870 A | 11/1985 | Krumme et al. | |
| 4,582,236 A | 4/1986 | Hirose | |
| 4,617,927 A | 10/1986 | Manes | |
| 4,735,603 A | 4/1988 | Goodson et al. | |
| 4,761,871 A | 8/1988 | O'Connor et al. | |
| 4,830,462 A | 5/1989 | Karny et al. | |
| 4,849,133 A | 7/1989 | Yoshida et al. | |
| 4,860,745 A | 8/1989 | Farin et al. | |
| 4,878,493 A | 11/1989 | Pasternak et al. | |
| 4,880,015 A | 11/1989 | Nierman | |
| 4,910,389 A | 3/1990 | Sherman et al. | |
| 4,920,978 A | 5/1990 | Colvin | |
| 4,936,842 A | 6/1990 | D'Amelio et al. | |
| 5,020,514 A | 6/1991 | Heckele | |
| 5,061,269 A | 10/1991 | Muller | |
| 5,099,840 A | 3/1992 | Goble et al. | |
| 5,104,025 A | 4/1992 | Main et al. | |
| 5,106,538 A | 4/1992 | Barma et al. | |
| 5,108,383 A | 4/1992 | White | |
| 5,156,633 A | 10/1992 | Smith | |
| 5,160,334 A | 11/1992 | Billings et al. | |
| 5,190,541 A | 3/1993 | Abele et al. | |
| 5,196,007 A | 3/1993 | Ellman et al. | |
| 5,205,459 A | 4/1993 | Brinkerhoff et al. | |
| 5,217,460 A | 6/1993 | Knoepfler | |
| 5,234,428 A | 8/1993 | Kaufman | |
| 5,258,006 A | 11/1993 | Rydell et al. | |
| 5,285,945 A | 2/1994 | Brinkerhoff et al. | |
| 5,290,286 A | 3/1994 | Parins | |
| 5,309,927 A | 5/1994 | Welch | |
| 5,312,023 A | 5/1994 | Green et al. | |
| 5,318,563 A | 6/1994 | Malis et al. | |
| 5,318,564 A | 6/1994 | Eggers | |
| 5,318,589 A | 6/1994 | Lichtman | |
| 5,326,013 A | 7/1994 | Green et al. | |
| 5,330,471 A | 7/1994 | Eggers | |
| 5,330,502 A | 7/1994 | Hassler et al. | |
| 5,339,723 A | 8/1994 | Huitema | |
| 5,342,359 A | 8/1994 | Rydell | |
| 5,361,583 A | 11/1994 | Huitema | |
| 5,383,874 A | 1/1995 | Jackson et al. | |
| 5,387,207 A | 2/1995 | Dyer et al. | |
| 5,389,098 A | 2/1995 | Tsuruta et al. | |
| 5,395,312 A | 3/1995 | Desai | |
| 5,395,363 A | 3/1995 | Billings et al. | |
| 5,395,364 A | 3/1995 | Anderhub et al. | |
| 5,396,266 A | 3/1995 | Brimhall | |
| 5,396,900 A | 3/1995 | Slater et al. | |
| 5,403,312 A | 4/1995 | Yates et al. | |
| 5,417,709 A | 5/1995 | Slater | |
| 5,428,504 A | 6/1995 | Bhatla | |
| 5,429,131 A | 7/1995 | Scheinman et al. | |
| 5,443,463 A | 8/1995 | Stern et al. | |
| 5,445,638 A | 8/1995 | Rydell et al. | |
| 5,451,227 A | 9/1995 | Michaelson | |
| 5,456,684 A | 10/1995 | Schmidt et al. | |
| 5,458,598 A | 10/1995 | Feinberg et al. | |
| 5,465,895 A | 11/1995 | Knodel et al. | |
| 5,472,443 A * | 12/1995 | Cordis | A61B 18/12 606/32 |
| 5,476,479 A | 12/1995 | Green et al. | |
| 5,478,003 A | 12/1995 | Green et al. | |
| 5,480,409 A | 1/1996 | Riza | |
| 5,484,436 A | 1/1996 | Eggers et al. | |
| 5,486,189 A | 1/1996 | Mudry et al. | |
| 5,496,317 A | 3/1996 | Goble et al. | |
| 5,504,650 A | 4/1996 | Katsui et al. | |
| 5,509,922 A | 4/1996 | Aranyi et al. | |
| 5,511,556 A | 4/1996 | DeSantis | |
| 5,520,704 A | 5/1996 | Castro et al. | |
| 5,522,839 A | 6/1996 | Pilling | |
| 5,531,744 A | 7/1996 | Nardella et al. | |
| 5,540,681 A | 7/1996 | Strul et al. | |
| 5,542,916 A | 8/1996 | Hirsch et al. | |
| 5,558,671 A | 9/1996 | Yates | |
| 5,563,179 A | 10/1996 | Stone et al. | |
| 5,569,164 A | 10/1996 | Lurz | |
| 5,571,121 A | 11/1996 | Heifetz | |
| 5,573,534 A | 11/1996 | Stone | |
| 5,584,830 A | 12/1996 | Ladd et al. | |
| 5,599,350 A * | 2/1997 | Schulze | A61B 18/1442 606/171 |
| 5,600,526 A * | 2/1997 | Russell | G01R 31/025 361/115 |
| 5,607,450 A | 3/1997 | Zvenyatsky et al. | |
| 5,611,813 A | 3/1997 | Lichtman | |
| 5,618,307 A | 4/1997 | Donlon et al. | |
| 5,624,452 A | 4/1997 | Yates | |
| 5,632,432 A | 5/1997 | Schulze et al. | |
| 5,647,871 A | 7/1997 | Levine et al. | |
| 5,658,281 A | 8/1997 | Heard | |
| 5,662,667 A | 9/1997 | Knodel | |
| 5,665,085 A | 9/1997 | Nardella | |
| 5,665,100 A | 9/1997 | Yoon | |
| 5,674,219 A | 10/1997 | Monson et al. | |
| 5,674,220 A | 10/1997 | Fox et al. | |
| 5,688,270 A | 11/1997 | Yates et al. | |
| 5,693,051 A * | 12/1997 | Schulze | A61B 17/07207 606/41 |
| 5,709,680 A | 1/1998 | Yates et al. | |
| 5,711,472 A | 1/1998 | Bryan | |
| 5,713,896 A | 2/1998 | Nardella | |
| 5,716,366 A | 2/1998 | Yates | |
| 5,720,742 A | 2/1998 | Zacharias | |
| 5,720,744 A | 2/1998 | Eggleston et al. | |
| 5,735,848 A | 4/1998 | Yates et al. | |
| 5,743,906 A | 4/1998 | Parins et al. | |
| 5,752,973 A | 5/1998 | Kieturakis | |
| 5,755,717 A | 5/1998 | Yates et al. | |
| 5,762,255 A | 6/1998 | Chrisman et al. | |
| 5,779,701 A | 7/1998 | McBrayer et al. | |
| 5,782,834 A | 7/1998 | Lucey et al. | |
| 5,792,135 A | 8/1998 | Madhani et al. | |
| 5,792,138 A | 8/1998 | Shipp | |
| 5,796,188 A | 8/1998 | Bays | |
| 5,797,941 A | 8/1998 | Schulze et al. | |
| 5,800,432 A | 9/1998 | Swanson | |
| 5,800,449 A | 9/1998 | Wales | |
| 5,805,140 A | 9/1998 | Rosenberg et al. | |
| 5,807,393 A | 9/1998 | Williamson, IV et al. | |
| 5,810,811 A | 9/1998 | Yates et al. | |
| 5,817,033 A | 10/1998 | DeSantis et al. | |
| 5,817,084 A | 10/1998 | Jensen | |
| 5,817,093 A | 10/1998 | Williamson, IV et al. | |

(56) References Cited

U.S. PATENT DOCUMENTS

| | | | |
|---|---|---|---|
| 5,827,323 A | 10/1998 | Klieman | |
| 5,836,909 A | 11/1998 | Cosmescu | |
| 5,836,943 A | 11/1998 | Miller, III | |
| 5,836,990 A | 11/1998 | Li | |
| 5,853,412 A | 12/1998 | Mayenberger | |
| 5,876,401 A * | 3/1999 | Schulze | A61B 17/07207 606/41 |
| 5,878,193 A | 3/1999 | Wang et al. | |
| 5,880,668 A | 3/1999 | Hall | |
| 5,891,142 A | 4/1999 | Eggers et al. | |
| 5,906,625 A | 5/1999 | Bito et al. | |
| 5,910,129 A | 6/1999 | Koblish et al. | |
| 5,921,956 A | 7/1999 | Grinberg et al. | |
| 5,929,846 A | 7/1999 | Rosenberg et al. | |
| 5,954,717 A * | 9/1999 | Behl | A61B 18/1477 604/114 |
| 5,984,938 A | 11/1999 | Yoon | |
| 6,003,517 A | 12/1999 | Sheffield et al. | |
| 6,013,052 A | 1/2000 | Durman et al. | |
| 6,024,741 A | 2/2000 | Williamson, IV et al. | |
| 6,024,744 A | 2/2000 | Kese et al. | |
| 6,033,399 A | 3/2000 | Gines | |
| 6,039,734 A | 3/2000 | Goble | |
| 6,050,996 A | 4/2000 | Schmaltz et al. | |
| 6,063,098 A | 5/2000 | Houser et al. | |
| 6,068,629 A | 5/2000 | Haissaguerre et al. | |
| 6,074,389 A | 6/2000 | Levine et al. | |
| 6,080,149 A * | 6/2000 | Huang | A61B 18/1206 324/600 |
| 6,091,995 A | 7/2000 | Ingle et al. | |
| 6,099,483 A | 8/2000 | Palmer et al. | |
| 6,099,550 A | 8/2000 | Yoon | |
| H1904 H | 10/2000 | Yates et al. | |
| 6,132,368 A | 10/2000 | Cooper | |
| 6,144,402 A | 11/2000 | Norsworthy et al. | |
| 6,152,923 A | 11/2000 | Ryan | |
| 6,154,198 A | 11/2000 | Rosenberg | |
| 6,162,208 A | 12/2000 | Hipps | |
| 6,174,309 B1 | 1/2001 | Wrublewski et al. | |
| 6,176,857 B1 | 1/2001 | Ashley | |
| 6,190,386 B1 | 2/2001 | Rydell | |
| 6,206,876 B1 | 3/2001 | Levine et al. | |
| 6,228,080 B1 | 5/2001 | Gines | |
| 6,231,565 B1 | 5/2001 | Tovey et al. | |
| 6,259,230 B1 | 7/2001 | Chou | |
| 6,277,117 B1 | 8/2001 | Tetzlaff et al. | |
| 6,292,700 B1 | 9/2001 | Morrison et al. | |
| 6,325,799 B1 | 12/2001 | Goble | |
| 6,340,878 B1 | 1/2002 | Oglesbee | |
| 6,358,246 B1 * | 3/2002 | Behl | A61B 18/1482 606/27 |
| 6,364,888 B1 | 4/2002 | Niemeyer et al. | |
| 6,387,109 B1 | 5/2002 | Davison et al. | |
| 6,391,026 B1 | 5/2002 | Hung et al. | |
| 6,398,779 B1 | 6/2002 | Buysse et al. | |
| 6,409,722 B1 | 6/2002 | Hoey et al. | |
| H2037 H | 7/2002 | Yates et al. | |
| 6,419,675 B1 | 7/2002 | Gallo, Sr. | |
| 6,430,446 B1 | 8/2002 | Knowlton | |
| 6,443,963 B1 | 9/2002 | Holthaus et al. | |
| 6,458,128 B1 | 10/2002 | Schulze | |
| 6,464,689 B1 | 10/2002 | Qin et al. | |
| 6,464,702 B2 | 10/2002 | Schulze et al. | |
| 6,468,270 B1 * | 10/2002 | Hovda | A61B 18/148 128/898 |
| 6,480,796 B2 | 11/2002 | Wiener | |
| 6,491,690 B1 | 12/2002 | Goble et al. | |
| 6,500,112 B1 | 12/2002 | Khouri | |
| 6,500,176 B1 | 12/2002 | Truckai et al. | |
| 6,503,248 B1 | 1/2003 | Levine | |
| 6,511,480 B1 | 1/2003 | Tetzlaff et al. | |
| 6,514,252 B2 | 2/2003 | Nezhat et al. | |
| 6,517,565 B1 | 2/2003 | Whitman et al. | |
| 6,531,846 B1 | 3/2003 | Smith | |
| 6,533,784 B2 | 3/2003 | Truckai et al. | |
| 6,537,272 B2 | 3/2003 | Christopherson et al. | |
| 6,537,291 B2 * | 3/2003 | Friedman | A61B 17/320068 606/169 |
| 6,551,309 B1 | 4/2003 | LePivert | |
| 6,554,829 B2 | 4/2003 | Schulze et al. | |
| 6,558,376 B2 | 5/2003 | Bishop | |
| 6,562,037 B2 | 5/2003 | Paton et al. | |
| 6,572,639 B1 | 6/2003 | Ingle et al. | |
| 6,575,969 B1 | 6/2003 | Rittman, III et al. | |
| 6,582,451 B1 | 6/2003 | Marucci et al. | |
| 6,584,360 B2 | 6/2003 | Francischelli et al. | |
| 6,585,735 B1 | 7/2003 | Frazier et al. | |
| 6,589,200 B1 | 7/2003 | Schwemberger et al. | |
| 6,602,252 B2 | 8/2003 | Mollenauer | |
| 6,610,060 B2 | 8/2003 | Mulier et al. | |
| 6,619,529 B2 | 9/2003 | Green et al. | |
| 6,620,161 B2 | 9/2003 | Schulze et al. | |
| 6,622,731 B2 | 9/2003 | Daniel et al. | |
| 6,623,482 B2 | 9/2003 | Pendekanti et al. | |
| 6,635,057 B2 | 10/2003 | Harano et al. | |
| 6,644,532 B2 | 11/2003 | Green et al. | |
| 6,651,669 B1 | 11/2003 | Burnside | |
| 6,656,177 B2 | 12/2003 | Truckai et al. | |
| 6,656,198 B2 | 12/2003 | Tsonton et al. | |
| 6,662,127 B2 * | 12/2003 | Wiener | A61B 17/320068 606/169 |
| 6,673,248 B2 | 1/2004 | Chowdhury | |
| 6,679,882 B1 | 1/2004 | Kornerup | |
| 6,682,501 B1 | 1/2004 | Nelson et al. | |
| 6,695,840 B2 | 2/2004 | Schulze | |
| 6,722,552 B2 | 4/2004 | Fenton, Jr. | |
| 6,733,498 B2 | 5/2004 | Paton et al. | |
| 6,746,443 B1 | 6/2004 | Morley et al. | |
| 6,752,815 B2 | 6/2004 | Beaupre | |
| 6,766,202 B2 | 7/2004 | Underwood et al. | |
| 6,770,072 B1 | 8/2004 | Truckai et al. | |
| 6,773,409 B2 | 8/2004 | Truckai et al. | |
| 6,773,435 B2 | 8/2004 | Schulze et al. | |
| 6,775,575 B2 | 8/2004 | Bommannan et al. | |
| 6,783,524 B2 | 8/2004 | Anderson et al. | |
| 6,789,939 B2 | 9/2004 | Schrödinger et al. | |
| 6,796,981 B2 | 9/2004 | Wham et al. | |
| 6,800,085 B2 | 10/2004 | Selmon et al. | |
| 6,802,843 B2 | 10/2004 | Truckai et al. | |
| 6,811,842 B1 | 11/2004 | Ehrnsperger et al. | |
| 6,821,273 B2 | 11/2004 | Mollenauer | |
| 6,835,199 B2 | 12/2004 | McGuckin, Jr. et al. | |
| 6,840,938 B1 | 1/2005 | Morley et al. | |
| 6,860,880 B2 | 3/2005 | Treat et al. | |
| 6,877,647 B2 | 4/2005 | Green et al. | |
| 6,893,435 B2 | 5/2005 | Goble | |
| 6,905,497 B2 | 6/2005 | Truckai et al. | |
| 6,908,463 B2 | 6/2005 | Treat et al. | |
| 6,913,579 B2 | 7/2005 | Truckai et al. | |
| 6,926,716 B2 | 8/2005 | Baker et al. | |
| 6,929,622 B2 | 8/2005 | Chian | |
| 6,929,644 B2 | 8/2005 | Truckai et al. | |
| 6,953,461 B2 | 10/2005 | McClurken et al. | |
| 6,977,495 B2 | 12/2005 | Donofrio | |
| 6,994,709 B2 | 2/2006 | Iida | |
| 7,000,818 B2 | 2/2006 | Shelton, IV et al. | |
| 7,011,657 B2 | 3/2006 | Truckai et al. | |
| 7,025,732 B2 * | 4/2006 | Thompson | A61B 10/0275 600/564 |
| 7,041,102 B2 | 5/2006 | Truckai et al. | |
| 7,052,496 B2 | 5/2006 | Yamauchi | |
| 7,055,731 B2 | 6/2006 | Shelton, IV et al. | |
| 7,063,699 B2 | 6/2006 | Hess et al. | |
| 7,066,936 B2 | 6/2006 | Ryan | |
| 7,077,853 B2 | 7/2006 | Kramer et al. | |
| 7,033,619 B2 | 8/2006 | Truckai et al. | |
| 7,037,054 B2 | 8/2006 | Truckai et al. | |
| 7,083,618 B2 | 8/2006 | Couture et al. | |
| 7,083,619 B2 | 8/2006 | Truckai et al. | |
| 7,094,235 B2 | 8/2006 | Francischelli et al. | |
| 7,101,371 B2 | 9/2006 | Dycus et al. | |
| 7,101,372 B2 | 9/2006 | Dycus et al. | |
| 7,101,373 B2 | 9/2006 | Dycus et al. | |

(56) References Cited

U.S. PATENT DOCUMENTS

| | | |
|---|---|---|
| 7,112,201 B2 | 9/2006 | Truckai et al. |
| 7,118,570 B2 | 10/2006 | Tetzlaff et al. |
| 7,125,409 B2 | 10/2006 | Truckai et al. |
| 7,131,970 B2 | 11/2006 | Moses et al. |
| 7,137,980 B2 | 11/2006 | Buysse et al. |
| 7,143,925 B2 | 12/2006 | Shelton, IV et al. |
| 7,147,138 B2 | 12/2006 | Shelton, IV |
| 7,156,846 B2 | 1/2007 | Dycus et al. |
| 7,160,296 B2 | 1/2007 | Pearson et al. |
| 7,169,146 B2 | 1/2007 | Truckai et al. |
| 7,169,156 B2 | 1/2007 | Hart |
| 7,179,271 B2 | 2/2007 | Friedman et al. |
| 7,186,253 B2 | 3/2007 | Truckai et al. |
| 7,189,233 B2 | 3/2007 | Truckai et al. |
| 7,195,631 B2 | 3/2007 | Dumbauld |
| 7,207,471 B2 | 4/2007 | Heinrich et al. |
| 7,220,951 B2 | 5/2007 | Truckai et al. |
| 7,225,964 B2 | 6/2007 | Mastri et al. |
| 7,226,448 B2 | 6/2007 | Bertolero et al. |
| 7,232,440 B2 | 6/2007 | Dumbauld et al. |
| 7,235,073 B2 | 6/2007 | Levine et al. |
| 7,241,294 B2 | 7/2007 | Reschke |
| 7,251,531 B2 | 7/2007 | Mosher et al. |
| 7,252,641 B2 * | 8/2007 | Thompson ......... A61B 10/0275 600/564 |
| 7,252,667 B2 | 8/2007 | Moses et al. |
| 7,267,677 B2 | 9/2007 | Johnson et al. |
| 7,267,685 B2 | 9/2007 | Butaric et al. |
| 7,273,483 B2 | 9/2007 | Wiener et al. |
| 7,237,682 B2 | 10/2007 | Ezzat et al. |
| 7,297,149 B2 | 11/2007 | Vitali et al. |
| 7,300,450 B2 | 11/2007 | Vleugels et al. |
| 7,303,557 B2 | 12/2007 | Wham et al. |
| 7,307,313 B2 | 12/2007 | Ohyanagi et al. |
| 7,309,849 B2 | 12/2007 | Truckai et al. |
| 7,311,709 B2 | 12/2007 | Truckai et al. |
| 7,329,257 B2 | 2/2008 | Kanehira et al. |
| 7,354,440 B2 | 4/2008 | Truckai et al. |
| 7,357,287 B2 | 4/2008 | Shelton, IV et al. |
| 7,364,577 B2 | 4/2008 | Wham et al. |
| 7,367,976 B2 | 5/2008 | Lawes et al. |
| 7,371,227 B2 | 5/2008 | Zeiner |
| RE40,388 E | 6/2008 | Gines |
| 7,381,209 B2 | 6/2008 | Truckai et al. |
| 7,384,420 B2 | 6/2008 | Dycus et al. |
| 7,396,356 B2 | 7/2008 | Mollenauer |
| 7,403,224 B2 | 7/2008 | Fuller et al. |
| 7,404,508 B2 | 7/2008 | Smith et al. |
| 7,407,077 B2 | 8/2008 | Ortiz et al. |
| 7,416,101 B2 | 8/2008 | Shelton, IV et al. |
| 7,422,139 B2 | 9/2008 | Shelton, IV et al. |
| 7,435,582 B2 | 10/2008 | Zimmermann et al. |
| 7,441,684 B2 | 10/2008 | Shelton, IV et al. |
| 7,442,193 B2 | 10/2008 | Shields et al. |
| 7,445,621 B2 | 11/2008 | Dumbauld et al. |
| 7,464,846 B2 | 12/2008 | Shelton, IV et al. |
| 7,473,253 B2 | 1/2009 | Dycus et al. |
| 7,488,319 B2 | 2/2009 | Yates |
| 7,491,201 B2 | 2/2009 | Shields et al. |
| 7,494,501 B2 | 2/2009 | Ahlberg et al. |
| 7,498,080 B2 | 3/2009 | Tung et al. |
| 7,506,791 B2 | 3/2009 | Omaits et al. |
| 7,510,107 B2 | 3/2009 | Timm et al. |
| 7,513,025 B2 | 4/2009 | Fischer |
| 7,517,349 B2 | 4/2009 | Truckai et al. |
| 7,524,320 B2 | 4/2009 | Tierney et al. |
| 7,535,233 B2 * | 5/2009 | Kojovic ............... G01R 31/085 324/509 |
| 7,540,872 B2 | 6/2009 | Schechter et al. |
| 7,543,730 B1 | 6/2009 | Marczyk |
| 7,550,216 B2 | 6/2009 | Ofer et al. |
| 7,553,309 B2 | 6/2009 | Buysse et al. |
| 7,559,452 B2 | 7/2009 | Wales et al. |
| 7,582,086 B2 | 9/2009 | Privitera et al. |
| 7,586,289 B2 | 9/2009 | Andruk et al. |
| 7,588,176 B2 | 9/2009 | Timm et al. |
| 7,594,925 B2 | 9/2009 | Danek et al. |
| 7,604,150 B2 | 10/2009 | Boudreaux |
| 7,621,930 B2 | 11/2009 | Houser |
| 7,628,791 B2 | 12/2009 | Garrison |
| 7,628,792 B2 | 12/2009 | Guerra |
| 7,632,267 B2 | 12/2009 | Dahla |
| 7,632,269 B2 | 12/2009 | Truckai et al. |
| 7,641,653 B2 | 1/2010 | Dalla Betta et al. |
| 7,641,671 B2 | 1/2010 | Crainich |
| 7,644,848 B2 | 1/2010 | Swayze et al. |
| 7,645,240 B2 * | 1/2010 | Thompson ......... A61B 10/0275 600/568 |
| 7,645,277 B2 | 1/2010 | McClurken et al. |
| 7,648,499 B2 | 1/2010 | Orszulak et al. |
| 7,658,311 B2 | 2/2010 | Boudreaux |
| 7,665,647 B2 | 2/2010 | Shelton, IV et al. |
| 7,666,206 B2 | 2/2010 | Taniguchi et al. |
| 7,670,334 B2 | 3/2010 | Hueil et al. |
| 7,691,095 B2 | 4/2010 | Bednarek et al. |
| 7,691,098 B2 | 4/2010 | Wallace et al. |
| 7,703,459 B2 | 4/2010 | Saadat et al. |
| 7,703,653 B2 | 4/2010 | Shah et al. |
| 7,708,751 B2 | 5/2010 | Hughes et al. |
| 7,717,915 B2 | 5/2010 | Miyazawa |
| 7,722,527 B2 | 5/2010 | Bouchier et al. |
| 7,722,607 B2 | 5/2010 | Dumbauld et al. |
| 7,726,537 B2 | 6/2010 | Olson et al. |
| 7,753,904 B2 | 7/2010 | Shelton, IV et al. |
| 7,753,908 B2 | 7/2010 | Swanson |
| 7,762,445 B2 | 7/2010 | Heinrich et al. |
| 7,730,663 B2 | 8/2010 | Yates et al. |
| 7,734,663 B2 | 8/2010 | Shelton, IV |
| 7,766,210 B2 | 8/2010 | Shelton, IV et al. |
| 7,766,910 B2 | 8/2010 | Hixson et al. |
| 7,770,775 B2 | 8/2010 | Shelton, IV et al. |
| 7,775,972 B2 | 8/2010 | Brock et al. |
| 7,776,037 B2 | 8/2010 | Odom |
| 7,780,651 B2 | 8/2010 | Madhani et al. |
| 7,739,883 B2 | 9/2010 | Takashino et al. |
| 7,793,814 B2 | 9/2010 | Racenet et al. |
| 7,803,156 B2 | 9/2010 | Eder et al. |
| 7,806,891 B2 | 10/2010 | Nowlin et al. |
| 7,810,693 B2 | 10/2010 | Broehl et al. |
| 7,815,641 B2 | 10/2010 | Dodde et al. |
| 7,819,298 B2 | 10/2010 | Hall et al. |
| 7,819,299 B2 | 10/2010 | Shelton, IV et al. |
| 7,819,872 B2 | 10/2010 | Johnson et al. |
| 7,824,401 B2 | 11/2010 | Manzo et al. |
| 7,832,408 B2 | 11/2010 | Shelton, IV et al. |
| 7,832,612 B2 | 11/2010 | Baxter, III et al. |
| 7,845,537 B2 | 12/2010 | Shelton, IV et al. |
| 7,846,159 B2 | 12/2010 | Morrison et al. |
| 7,846,160 B2 | 12/2010 | Payne et al. |
| 7,861,906 B2 | 1/2011 | Doll et al. |
| 7,879,035 B2 | 2/2011 | Garrison et al. |
| 7,879,070 B2 | 2/2011 | Ortiz et al. |
| 7,896,875 B2 | 3/2011 | Heim et al. |
| 7,901,400 B2 | 3/2011 | Wham et al. |
| 7,909,220 B2 | 3/2011 | Viola |
| 7,919,184 B2 | 4/2011 | Mohapatra et al. |
| 7,922,061 B2 | 4/2011 | Shelton, IV et al. |
| 7,922,651 B2 | 4/2011 | Yamada et al. |
| 7,931,649 B2 | 4/2011 | Couture et al. |
| 7,935,114 B2 | 5/2011 | Takashino et al. |
| 7,951,165 B2 | 5/2011 | Golden et al. |
| 7,955,331 B2 | 6/2011 | Truckai et al. |
| 7,963,963 B2 | 6/2011 | Francischelli et al. |
| 7,967,602 B2 | 6/2011 | Lindquist |
| 7,981,113 B2 | 7/2011 | Truckai et al. |
| 7,997,278 B2 | 8/2011 | Utley et al. |
| 8,020,743 B2 | 9/2011 | Shelton, IV |
| 8,038,693 B2 | 10/2011 | Allen |
| 8,056,720 B2 | 11/2011 | Hawkes |
| 8,056,787 B2 | 11/2011 | Boudreaux et al. |
| 8,058,771 B2 | 11/2011 | Giordano et al. |
| 8,061,014 B2 | 11/2011 | Smith et al. |
| 8,070,036 B1 | 12/2011 | Knodel et al. |
| 8,105,323 B2 | 1/2012 | Buysse et al. |

(56) References Cited

U.S. PATENT DOCUMENTS

| | | | |
|---|---|---|---|
| 8,128,624 B2 | 3/2012 | Couture et al. |
| 8,136,712 B2 | 3/2012 | Zingman |
| 8,141,762 B2 | 3/2012 | Bedi et al. |
| 8,157,145 B2 | 4/2012 | Shelton, IV et al. |
| 8,197,472 B2 | 6/2012 | Lau et al. |
| 8,197,479 B2 | 6/2012 | Olson et al. |
| 8,197,502 B2 | 6/2012 | Smith et al. |
| 8,221,415 B2 | 7/2012 | Francischelli |
| 8,236,020 B2 | 8/2012 | Smith et al. |
| 8,241,235 B2 | 8/2012 | Kahler et al. |
| 8,241,284 B2 | 8/2012 | Dycus et al. |
| 8,246,615 B2 | 8/2012 | Behnke |
| 8,246,618 B2 | 8/2012 | Bucciaglia et al. |
| 8,251,994 B2 | 8/2012 | McKenna et al. |
| 8,262,563 B2 | 9/2012 | Bakos et al. |
| 8,267,300 B2 | 9/2012 | Boudreaux |
| 8,237,528 B2 | 10/2012 | Wham et al. |
| 8,277,446 B2 | 10/2012 | Heard |
| 8,277,447 B2 | 10/2012 | Garrison et al. |
| 8,282,669 B2 | 10/2012 | Gerber et al. |
| 8,292,886 B2 | 10/2012 | Kerr et al. |
| 8,298,232 B2 | 10/2012 | Unger |
| 8,303,533 B2 | 11/2012 | Hosier et al. |
| 8,323,310 B2 | 12/2012 | Kingsley |
| 8,333,778 B2 | 12/2012 | Smith et al. |
| 8,333,779 B2 | 12/2012 | Smith et al. |
| 8,334,468 B2 | 12/2012 | Palmer et al. |
| 8,338,726 B2 | 12/2012 | Palmer et al. |
| 8,357,158 B2 | 1/2013 | McKenna et al. |
| 8,361,569 B2 | 1/2013 | Saito et al. |
| 8,372,064 B2 | 2/2013 | Douglass et al. |
| 8,372,099 B2 | 2/2013 | Deville et al. |
| 8,372,101 B2 | 2/2013 | Smith et al. |
| 8,377,059 B2 | 2/2013 | Deville et al. |
| 8,377,085 B2 | 2/2013 | Smith et al. |
| 8,397,971 B2 | 3/2013 | Yates et al. |
| 8,403,948 B2 | 3/2013 | Deville et al. |
| 8,403,949 B2 | 3/2013 | Palmer et al. |
| 8,403,950 B2 | 3/2013 | Palmer et al. |
| 8,414,577 B2 | 4/2013 | Boudreaux et al. |
| 8,418,349 B2 | 4/2013 | Smith et al. |
| 8,419,757 B2 | 4/2013 | Smith et al. |
| 8,419,758 B2 | 4/2013 | Smith et al. |
| 8,425,545 B2 | 4/2013 | Smith et al. |
| 8,430,876 B2 | 4/2013 | Kappus et al. |
| 8,435,257 B2 | 5/2013 | Smith et al. |
| 8,439,939 B2 | 5/2013 | Deville et al. |
| 8,444,662 B2 | 5/2013 | Palmer et al. |
| 8,444,664 B2 | 5/2013 | Balanev et al. |
| 8,453,906 B2 | 6/2013 | Huang et al. |
| 8,460,288 B2 | 6/2013 | Tamai et al. |
| 8,460,292 B2 | 6/2013 | Truckai et al. |
| 8,461,744 B2 | 6/2013 | Wiener et al. |
| 8,480,703 B2 | 7/2013 | Nicholas et al. |
| 8,485,413 B2 | 7/2013 | Scheib et al. |
| 8,486,057 B2 | 7/2013 | Behnke, II |
| 8,496,682 B2 | 7/2013 | Guerra et al. |
| 8,535,311 B2 | 9/2013 | Schall |
| 8,535,340 B2 | 9/2013 | Allen |
| 8,535,341 B2 | 9/2013 | Allen |
| 8,540,128 B2 | 9/2013 | Shelton, IV et al. |
| 8,562,598 B2 | 10/2013 | Falkenstein et al. |
| 8,562,604 B2 | 10/2013 | Nishimura |
| 8,568,390 B2 | 10/2013 | Mueller |
| 8,568,412 B2 | 10/2013 | Brandt et al. |
| 8,569,997 B2 | 10/2013 | Lee |
| 8,574,231 B2 | 11/2013 | Boudreaux et al. |
| 8,588,371 B2 * | 11/2013 | Ogawa ............ H02M 7/53871 378/101 |
| 8,591,506 B2 | 11/2013 | Wham et al. |
| D695,407 S | 12/2013 | Price et al. |
| 8,608,044 B2 | 12/2013 | Hueil et al. |
| 8,613,383 B2 | 12/2013 | Beckman et al. |
| 8,623,011 B2 | 1/2014 | Spivey |
| 8,623,016 B2 | 1/2014 | Fischer |
| 8,623,027 B2 | 1/2014 | Price et al. |
| 8,623,044 B2 | 1/2014 | Timm et al. |
| 8,628,529 B2 | 1/2014 | Aldridge et al. |
| 8,632,461 B2 | 1/2014 | Glossop |
| 8,638,428 B2 | 1/2014 | Brown |
| 8,647,350 B2 | 2/2014 | Mohan et al. |
| 8,663,220 B2 | 3/2014 | Wiener et al. |
| 8,663,222 B2 | 3/2014 | Anderson et al. |
| 8,684,253 B2 | 4/2014 | Giordano et al. |
| 8,685,020 B2 | 4/2014 | Weizman et al. |
| 8,696,665 B2 | 4/2014 | Hunt et al. |
| 8,702,609 B2 | 4/2014 | Hadjicostis |
| 8,702,704 B2 | 4/2014 | Shelton, IV et al. |
| 8,709,035 B2 | 4/2014 | Johnson et al. |
| 8,715,270 B2 | 5/2014 | Weitzner et al. |
| 8,715,277 B2 | 5/2014 | Weizman |
| 8,734,443 B2 | 5/2014 | Hixson et al. |
| 8,747,238 B2 | 6/2014 | Shelton, IV et al. |
| 8,747,351 B2 | 6/2014 | Schultz |
| 8,747,404 B2 | 6/2014 | Boudreaux et al. |
| 8,752,264 B2 | 6/2014 | Ackley et al. |
| 8,752,749 B2 | 6/2014 | Moore et al. |
| 8,753,338 B2 | 6/2014 | Widenhouse et al. |
| 8,764,747 B2 | 7/2014 | Cummings et al. |
| 8,790,342 B2 | 7/2014 | Stulen et al. |
| 8,795,276 B2 | 8/2014 | Dietz et al. |
| 8,795,327 B2 | 8/2014 | Dietz et al. |
| 8,827,992 B2 | 9/2014 | Koss et al. |
| 8,834,466 B2 | 9/2014 | Cummings et al. |
| 8,834,518 B2 | 9/2014 | Faller et al. |
| 8,845,630 B2 | 9/2014 | Mehta et al. |
| 8,888,776 B2 | 11/2014 | Dietz et al. |
| 8,888,809 B2 | 11/2014 | Davison et al. |
| 8,906,016 B2 | 12/2014 | Boudreaux et al. |
| 8,926,607 B2 | 1/2015 | Norvell et al. |
| 8,926,608 B2 | 1/2015 | Bacher et al. |
| 8,931,682 B2 | 1/2015 | Timm et al. |
| 8,939,974 B2 | 1/2015 | Boudreaux et al. |
| 8,951,248 B2 | 2/2015 | Messerly et al. |
| 8,956,349 B2 | 2/2015 | Aldridge et al. |
| 8,979,843 B2 | 3/2015 | Timm et al. |
| 8,979,844 B2 | 3/2015 | White et al. |
| 8,979,890 B2 | 3/2015 | Boudreaux |
| 8,986,302 B2 | 3/2015 | Aldridge et al. |
| 8,992,422 B2 | 3/2015 | Spivey et al. |
| 9,005,199 B2 | 4/2015 | Beckman et al. |
| 9,011,437 B2 | 4/2015 | Woodruff et al. |
| 9,017,326 B2 | 4/2015 | DiNardo et al. |
| 9,028,494 B2 | 5/2015 | Shelton, IV et al. |
| 9,028,519 B2 | 5/2015 | Yates et al. |
| 9,039,731 B2 | 5/2015 | Joseph |
| 9,044,243 B2 | 6/2015 | Johnson et al. |
| 9,044,256 B2 | 6/2015 | Cadeddu et al. |
| 9,055,961 B2 | 6/2015 | Manzo et al. |
| 9,060,770 B2 | 6/2015 | Shelton, IV et al. |
| 9,066,723 B2 | 6/2015 | Beller et al. |
| 9,072,535 B2 | 7/2015 | Shelton, IV et al. |
| 9,072,536 B2 | 7/2015 | Shelton, IV et al. |
| 9,101,335 B2 | 8/2015 | Shelton, IV et al. |
| 9,119,657 B2 | 9/2015 | Shelton, IV et al. |
| 9,125,662 B2 | 9/2015 | Shelton, IV |
| 9,149,324 B2 | 10/2015 | Huang et al. |
| 9,149,325 B2 | 10/2015 | Worrell et al. |
| 9,168,085 B2 | 10/2015 | Juzkiw et al. |
| 9,176,912 B2 | 11/2015 | Yates et al. |
| 9,192,380 B2 | 11/2015 | (Tarinelli) Racenet et al. |
| 9,192,421 B2 | 11/2015 | Garrison |
| 9,192,431 B2 | 11/2015 | Woodruff et al. |
| 9,198,714 B2 | 12/2015 | Worrell et al. |
| 9,204,879 B2 | 12/2015 | Shelton, IV |
| 9,216,050 B2 | 12/2015 | Condie et al. |
| 9,226,751 B2 | 1/2016 | Shelton, IV et al. |
| 9,226,766 B2 * | 1/2016 | Aldridge ........ A61B 17/320068 |
| 9,226,767 B2 | 1/2016 | Stulen et al. |
| 9,237,891 B2 | 1/2016 | Shelton, IV |
| 9,237,921 B2 * | 1/2016 | Messerly ........ A61B 17/320068 |
| 9,241,731 B2 * | 1/2016 | Boudreaux .... A61B 17/320068 |
| 9,259,265 B2 | 2/2016 | Harris et al. |
| 9,265,926 B2 | 2/2016 | Strobl et al. |

(56) References Cited

U.S. PATENT DOCUMENTS

| | | |
|---|---|---|
| 9,233,027 B1 | 3/2016 | Monson et al. |
| 9,277,962 B2 | 3/2016 | Koss et al. |
| 9,283,045 B2 | 3/2016 | Rhee et al. |
| 9,295,514 B2 | 3/2016 | Shelton, IV et al. |
| 9,314,292 B2 | 4/2016 | Trees et al. |
| 9,326,788 B2 | 5/2016 | Batross et al. |
| 9,333,025 B2 | 5/2016 | Monson et al. |
| 9,351,754 B2 | 5/2016 | Vakharia et al. |
| 9,375,232 B2 | 6/2016 | Hunt et al. |
| 9,375,256 B2 | 6/2016 | Cunningham et al. |
| 9,375,267 B2 | 6/2016 | Kerr et al. |
| 9,408,660 B2 | 8/2016 | Strobl et al. |
| 9,414,880 B2 | 8/2016 | Monson et al. |
| 9,421,060 B2 | 8/2016 | Monson et al. |
| 9,456,863 B2 | 10/2016 | Moua |
| 9,456,864 B2 | 10/2016 | Witt et al. |
| 9,510,906 B2 | 12/2016 | Boudreaux et al. |
| 9,522,029 B2 | 12/2016 | Yates et al. |
| 2002/0022836 A1 | 2/2002 | Goble et al. |
| 2002/0029036 A1* | 3/2002 | Goble ................ A61B 18/082 606/38 |
| 2002/0035362 A1* | 3/2002 | Behl ................ A61B 18/1482 606/34 |
| 2002/0049551 A1 | 4/2002 | Friedman et al. |
| 2002/0049552 A1* | 4/2002 | Wiener .......... A61B 17/320068 702/72 |
| 2002/0049555 A1* | 4/2002 | Wiener .......... A61B 17/320068 702/106 |
| 2002/0107517 A1 | 8/2002 | Witt et al. |
| 2002/0165531 A1* | 11/2002 | Goble ................ A61B 18/1206 606/32 |
| 2002/0165541 A1 | 11/2002 | Whitman |
| 2003/0009303 A1* | 1/2003 | Wiener .......... A61B 17/320068 702/106 |
| 2003/0014053 A1 | 1/2003 | Nguyen et al. |
| 2003/0105474 A1 | 6/2003 | Bonutti |
| 2003/0109875 A1 | 6/2003 | Tetzlaff et al. |
| 2003/0114851 A1 | 6/2003 | Truckai et al. |
| 2003/0130693 A1 | 7/2003 | Levin et al. |
| 2003/0139741 A1 | 7/2003 | Goble et al. |
| 2003/0158548 A1 | 8/2003 | Phan et al. |
| 2003/0171747 A1 | 9/2003 | Kanehira et al. |
| 2003/0216722 A1 | 11/2003 | Swanson |
| 2003/0229344 A1 | 12/2003 | Dycus et al. |
| 2004/0019350 A1 | 1/2004 | O'Brien et al. |
| 2004/0054364 A1 | 3/2004 | Aranyi et al. |
| 2004/0092992 A1 | 5/2004 | Adams et al. |
| 2004/0138621 A1 | 7/2004 | Jahns et al. |
| 2004/0147919 A1* | 7/2004 | Behl ................ A61B 18/1482 606/34 |
| 2004/0167508 A1 | 8/2004 | Wham et al. |
| 2004/0193150 A1 | 9/2004 | Sharkey et al. |
| 2004/0232196 A1 | 11/2004 | Shelton, IV et al. |
| 2004/0249374 A1 | 12/2004 | Tetzlaff et al. |
| 2004/0260273 A1 | 12/2004 | Wan |
| 2005/0015125 A1 | 1/2005 | Mioduski et al. |
| 2005/0033278 A1 | 2/2005 | McClurken et al. |
| 2005/0085809 A1 | 4/2005 | Mucko et al. |
| 2005/0090817 A1 | 4/2005 | Phan |
| 2005/0103819 A1 | 5/2005 | Racenet et al. |
| 2005/0131390 A1 | 6/2005 | Heinrich et al. |
| 2005/0165429 A1 | 7/2005 | Douglas et al. |
| 2005/0171522 A1 | 8/2005 | Christopherson |
| 2005/0203504 A1* | 9/2005 | Wham ................ A61B 18/1442 606/34 |
| 2005/0203507 A1 | 9/2005 | Truckai et al. |
| 2005/0256405 A1 | 11/2005 | Makin et al. |
| 2005/0261581 A1 | 11/2005 | Hughes et al. |
| 2005/0267464 A1 | 12/2005 | Truckai et al. |
| 2006/0052778 A1 | 3/2006 | Chapman et al. |
| 2006/0058825 A1 | 3/2006 | Ogura et al. |
| 2006/0064086 A1 | 3/2006 | Odom |
| 2006/0069388 A1 | 3/2006 | Truckai et al. |
| 2006/0159731 A1 | 7/2006 | Shoshan |
| 2006/0217707 A1* | 9/2006 | Daniel ................ A61B 18/1477 606/50 |
| 2006/0270916 A1 | 11/2006 | Skwarek et al. |
| 2006/0293656 A1 | 12/2006 | Shadduck et al. |
| 2007/0027469 A1 | 2/2007 | Smith et al. |
| 2007/0073185 A1 | 3/2007 | Nakao |
| 2007/0073341 A1 | 3/2007 | Smith et al. |
| 2007/0106158 A1 | 5/2007 | Madan et al. |
| 2007/0106317 A1 | 5/2007 | Shelton, IV et al. |
| 2007/0118115 A1 | 5/2007 | Artale et al. |
| 2007/0146113 A1 | 6/2007 | Truckai et al. |
| 2007/0173803 A1 | 7/2007 | Wham et al. |
| 2007/0173811 A1 | 7/2007 | Couture et al. |
| 2007/0173813 A1 | 7/2007 | Odom |
| 2007/0175949 A1 | 8/2007 | Shelton, IV et al. |
| 2007/0185474 A1 | 8/2007 | Nahen |
| 2007/0191713 A1 | 8/2007 | Eichmann et al. |
| 2007/0191830 A1 | 8/2007 | Cromton, Jr. et al. |
| 2007/0203483 A1 | 8/2007 | Kim et al. |
| 2007/0208312 A1 | 9/2007 | Norton et al. |
| 2007/0208340 A1 | 9/2007 | Ganz et al. |
| 2007/0232920 A1 | 10/2007 | Kowalski et al. |
| 2007/0232926 A1 | 10/2007 | Stulen et al. |
| 2007/0232927 A1 | 10/2007 | Madan et al. |
| 2007/0236213 A1 | 10/2007 | Paden et al. |
| 2007/0239025 A1 | 10/2007 | Wiener et al. |
| 2007/0260242 A1 | 11/2007 | Dycus et al. |
| 2007/0265613 A1 | 11/2007 | Edelstein et al. |
| 2007/0265616 A1 | 11/2007 | Couture et al. |
| 2008/0015575 A1 | 1/2008 | Odom et al. |
| 2008/0071269 A1 | 3/2008 | Hilario et al. |
| 2008/0114355 A1 | 5/2008 | Whayne et al. |
| 2008/0147058 A1 | 6/2008 | Horrell et al. |
| 2008/0147062 A1 | 6/2008 | Truckai et al. |
| 2008/0167522 A1 | 7/2008 | Giordano et al. |
| 2008/0188755 A1 | 8/2008 | Hart |
| 2008/0188851 A1 | 8/2008 | Truckai et al. |
| 2008/0188912 A1 | 8/2008 | Stone et al. |
| 2008/0214967 A1 | 9/2008 | Aranyi et al. |
| 2008/0221565 A1 | 9/2008 | Eder et al. |
| 2008/0255642 A1 | 10/2008 | Zarins et al. |
| 2008/0262491 A1 | 10/2008 | Swoyer et al. |
| 2008/0269862 A1 | 10/2008 | Elmouelhi et al. |
| 2008/0281315 A1* | 11/2008 | Gines ................ A61B 18/1206 606/38 |
| 2008/0287944 A1* | 11/2008 | Pearson ............ A61B 18/1477 606/41 |
| 2008/0294158 A1 | 11/2008 | Pappone et al. |
| 2008/0300588 A1 | 12/2008 | Groth et al. |
| 2009/0012516 A1 | 1/2009 | Curtis et al. |
| 2009/0048589 A1 | 2/2009 | Takashino et al. |
| 2009/0076506 A1 | 3/2009 | Baker |
| 2009/0076534 A1 | 3/2009 | Shelton, IV et al. |
| 2009/0082766 A1 | 3/2009 | Unger et al. |
| 2009/0099582 A1 | 4/2009 | Isaacs et al. |
| 2009/0112229 A1 | 4/2009 | Omori et al. |
| 2009/0125026 A1 | 5/2009 | Rioux et al. |
| 2009/0125027 A1 | 5/2009 | Fischer |
| 2009/0131929 A1 | 5/2009 | Shimizu |
| 2009/0138003 A1 | 5/2009 | Deville et al. |
| 2009/0138006 A1 | 5/2009 | Bales et al. |
| 2009/0182322 A1 | 7/2009 | D'Amelio et al. |
| 2009/0182331 A1 | 7/2009 | D'Amelio et al. |
| 2009/0182332 A1 | 7/2009 | Long et al. |
| 2009/0206140 A1 | 8/2009 | Scheib et al. |
| 2009/0209979 A1 | 8/2009 | Yates et al. |
| 2009/0240244 A1* | 9/2009 | Malis ................ A61B 18/1206 606/33 |
| 2009/0248002 A1 | 10/2009 | Takashino et al. |
| 2009/0248021 A1 | 10/2009 | McKenna |
| 2009/0254080 A1 | 10/2009 | Honda |
| 2009/0287205 A1 | 11/2009 | Ingle |
| 2009/0320268 A1 | 12/2009 | Cunningham et al. |
| 2009/0326530 A1 | 12/2009 | Orban, III et al. |
| 2010/0032470 A1 | 2/2010 | Hess et al. |
| 2010/0036370 A1 | 2/2010 | Mirel et al. |
| 2010/0036380 A1 | 2/2010 | Taylor et al. |
| 2010/0076433 A1 | 3/2010 | Taylor et al. |
| 2010/0081863 A1 | 4/2010 | Hess et al. |

(56) References Cited

U.S. PATENT DOCUMENTS

| | | |
|---|---|---|
| 2010/0081864 A1 | 4/2010 | Hess et al. |
| 2010/0081880 A1 | 4/2010 | Widenhouse et al. |
| 2010/0081881 A1 | 4/2010 | Murray et al. |
| 2010/0081882 A1 | 4/2010 | Hess et al. |
| 2010/0081883 A1 | 4/2010 | Murray et al. |
| 2010/0081995 A1 | 4/2010 | Widenhouse et al. |
| 2010/0094323 A1 | 4/2010 | Isaacs et al. |
| 2010/0168620 A1 | 7/2010 | Klimovitch et al. |
| 2010/0222752 A1 | 9/2010 | Collins, Jr. et al. |
| 2010/0237132 A1 | 9/2010 | Measamer et al. |
| 2010/0264194 A1 | 10/2010 | Huang et al. |
| 2010/0274278 A1 | 10/2010 | Fleenor et al. |
| 2011/0015627 A1 | 1/2011 | DiNardo et al. |
| 2011/0028963 A1* | 2/2011 | Gilbert ............... A61B 18/1206 606/33 |
| 2011/0037484 A1* | 2/2011 | Gilbert ............... A61B 18/1233 324/649 |
| 2011/0082486 A1 | 4/2011 | Messerly et al. |
| 2011/0087212 A1* | 4/2011 | Aldridge ........ A61B 17/320092 606/34 |
| 2011/0087214 A1 | 4/2011 | Giordano et al. |
| 2011/0087215 A1 | 4/2011 | Aldridge et al. |
| 2011/0087216 A1 | 4/2011 | Aldridge et al. |
| 2011/0087217 A1 | 4/2011 | Yates et al. |
| 2011/0087220 A1 | 4/2011 | Felder et al. |
| 2011/0118754 A1 | 5/2011 | Dachs, II et al. |
| 2011/0155781 A1 | 6/2011 | Swensgard et al. |
| 2011/0224668 A1 | 9/2011 | Johnson et al. |
| 2011/0276049 A1 | 11/2011 | Gerhardt |
| 2011/0276057 A1 | 11/2011 | Conlon et al. |
| 2011/0278343 A1 | 11/2011 | Knodel et al. |
| 2011/0284014 A1 | 11/2011 | Cededdu et al. |
| 2011/0290856 A1 | 12/2011 | Shelton, IV et al. |
| 2011/0295269 A1 | 12/2011 | Swensgard et al. |
| 2011/0295295 A1 | 12/2011 | Shelton, IV et al. |
| 2011/0301605 A1 | 12/2011 | Horner |
| 2011/0306967 A1 | 12/2011 | Payne et al. |
| 2011/0313415 A1 | 12/2011 | Fernandez et al. |
| 2011/0316606 A1* | 12/2011 | Ladurner ............... H03K 17/14 327/378 |
| 2012/0016413 A1 | 1/2012 | Timm et al. |
| 2012/0022519 A1 | 1/2012 | Huang et al. |
| 2012/0022526 A1 | 1/2012 | Aldridge et al. |
| 2012/0078139 A1* | 3/2012 | Aldridge ........ A61B 17/320092 601/2 |
| 2012/0078243 A1 | 3/2012 | Worrell et al. |
| 2012/0078244 A1 | 3/2012 | Worrell et al. |
| 2012/0078247 A1 | 3/2012 | Worrell et al. |
| 2012/0078248 A1 | 3/2012 | Worrell et al. |
| 2012/0083783 A1 | 4/2012 | Davison et al. |
| 2012/0109186 A1 | 5/2012 | Parrott et al. |
| 2012/0116265 A1 | 5/2012 | Houser et al. |
| 2012/0116379 A1 | 5/2012 | Yates et al. |
| 2012/0116380 A1 | 5/2012 | Madan et al. |
| 2012/0116391 A1 | 5/2012 | Houser et al. |
| 2012/0130256 A1 | 5/2012 | Buysse et al. |
| 2012/0136353 A1 | 5/2012 | Romero |
| 2012/0138660 A1 | 6/2012 | Shelton, IV |
| 2012/0150049 A1* | 6/2012 | Zielinski ............... A61B 5/027 600/481 |
| 2012/0150169 A1* | 6/2012 | Zielinksi ............... A61B 5/027 606/34 |
| 2012/0150170 A1 | 6/2012 | Buysse et al. |
| 2012/0150192 A1 | 6/2012 | Dachs, II et al. |
| 2012/0172859 A1 | 7/2012 | Condie et al. |
| 2012/0265196 A1 | 10/2012 | Turner et al. |
| 2012/0265241 A1 | 10/2012 | Hart et al. |
| 2012/0296371 A1 | 11/2012 | Kappus et al. |
| 2012/0323238 A1 | 12/2012 | Tyrrell et al. |
| 2013/0023925 A1 | 1/2013 | Mueller |
| 2013/0030428 A1 | 1/2013 | Worrell et al. |
| 2013/0030433 A1 | 1/2013 | Heard |
| 2013/0035685 A1 | 2/2013 | Fischer et al. |
| 2013/0079762 A1 | 3/2013 | Twomey et al. |
| 2013/0085496 A1 | 4/2013 | Unger et al. |
| 2013/0123776 A1 | 5/2013 | Monson et al. |
| 2013/0158659 A1 | 6/2013 | Bergs et al. |
| 2013/0158660 A1 | 6/2013 | Bergs et al. |
| 2013/0253256 A1 | 9/2013 | Griffith et al. |
| 2013/0253502 A1 | 9/2013 | Aronow et al. |
| 2013/0267975 A1* | 10/2013 | Timm ............... A61B 17/320068 606/169 |
| 2013/0282003 A1* | 10/2013 | Messerly ........ A61B 17/320068 606/37 |
| 2013/0296843 A1 | 11/2013 | Boudreaux et al. |
| 2013/0296908 A1 | 11/2013 | Schulte et al. |
| 2013/0338661 A1 | 12/2013 | Behnke, II |
| 2014/0001231 A1 | 1/2014 | Shelton, IV et al. |
| 2014/0001234 A1 | 1/2014 | Shelton, IV et al. |
| 2014/0001235 A1 | 1/2014 | Shelton, IV |
| 2014/0001236 A1 | 1/2014 | Shelton, IV et al. |
| 2014/0005640 A1 | 1/2014 | Shelton, IV et al. |
| 2014/0005653 A1 | 1/2014 | Shelton, IV et al. |
| 2014/0005678 A1 | 1/2014 | Shelton, IV et al. |
| 2014/0005680 A1 | 1/2014 | Shelton, IV et al. |
| 2014/0005681 A1 | 1/2014 | Gee et al. |
| 2014/0005693 A1 | 1/2014 | Shelton, IV et al. |
| 2014/0005694 A1 | 1/2014 | Shelton, IV et al. |
| 2014/0005695 A1 | 1/2014 | Shelton, IV |
| 2014/0005701 A1 | 1/2014 | Olson et al. |
| 2014/0005702 A1 | 1/2014 | Timm et al. |
| 2014/0005703 A1 | 1/2014 | Stulen et al. |
| 2014/0005705 A1 | 1/2014 | Weir et al. |
| 2014/0005718 A1 | 1/2014 | Shelton, IV et al. |
| 2014/0014544 A1 | 1/2014 | Bugnard et al. |
| 2014/0094801 A1 | 4/2014 | Boudreaux et al. |
| 2014/0180281 A1 | 6/2014 | Rusin |
| 2014/0194874 A1 | 7/2014 | Dietz et al. |
| 2014/0194875 A1 | 7/2014 | Reschke et al. |
| 2014/0194915 A1 | 7/2014 | Johnson et al. |
| 2014/0214019 A1 | 7/2014 | Baxter, III et al. |
| 2014/0228844 A1 | 8/2014 | Hörlle et al. |
| 2014/0232463 A1* | 8/2014 | Gilbert ............... A61B 18/1206 330/255 |
| 2014/0257270 A1* | 9/2014 | Behnke ............... A61B 18/1233 606/34 |
| 2014/0257284 A1 | 9/2014 | Artale |
| 2014/0276659 A1* | 9/2014 | Juergens ............ A61B 18/1233 604/542 |
| 2014/0276753 A1* | 9/2014 | Wham ............... A61B 18/1206 606/33 |
| 2014/0303551 A1 | 10/2014 | Germain et al. |
| 2014/0316408 A1 | 10/2014 | Davison et al. |
| 2014/0330271 A1 | 11/2014 | Dietz et al. |
| 2014/0343550 A1 | 11/2014 | Faller et al. |
| 2015/0018826 A1 | 1/2015 | Boudreaux |
| 2015/0032098 A1* | 1/2015 | Larson ............... A61B 18/1233 606/35 |
| 2015/0032100 A1* | 1/2015 | Coulson ............ A61B 18/1233 606/35 |
| 2015/0080876 A1 | 3/2015 | Worrell et al. |
| 2015/0080879 A1 | 3/2015 | Trees et al. |
| 2015/0080891 A1 | 3/2015 | Shelton, IV et al. |
| 2015/0088116 A1* | 3/2015 | Wham ............... A61B 18/1233 606/34 |
| 2015/0088124 A1* | 3/2015 | Wham ............... A61B 18/1445 606/40 |
| 2015/0133915 A1 | 5/2015 | Strobl et al. |
| 2015/0133929 A1 | 5/2015 | Evans et al. |
| 2015/0141981 A1 | 5/2015 | Price et al. |
| 2015/0190189 A1 | 7/2015 | Yates et al. |
| 2015/0196352 A1 | 7/2015 | Beckman et al. |
| 2015/0230853 A1 | 8/2015 | Johnson et al. |
| 2015/0230861 A1 | 8/2015 | Woloszko et al. |
| 2015/0265347 A1 | 9/2015 | Yates et al. |
| 2015/0272602 A1 | 10/2015 | Boudreaux et al. |
| 2015/0272657 A1 | 10/2015 | Yates et al. |
| 2015/0272659 A1 | 10/2015 | Boudreaux et al. |
| 2015/0272660 A1 | 10/2015 | Boudreaux et al. |
| 2015/0289925 A1 | 10/2015 | Voegele et al. |
| 2015/0297286 A1 | 10/2015 | Boudreaux et al. |

(56) References Cited

U.S. PATENT DOCUMENTS

| | | | |
|---|---|---|---|
| 2015/0320478 A1* | 11/2015 | Cosman, Jr. | A61B 18/1482 606/34 |
| 2015/0320479 A1* | 11/2015 | Cosman, Jr. | A61B 18/1482 606/35 |
| 2015/0320480 A1* | 11/2015 | Cosman, Jr. | A61B 18/1482 606/34 |
| 2015/0320481 A1* | 11/2015 | Cosman, Jr. | A61B 18/1482 606/35 |
| 2016/0045248 A1 | 2/2016 | Unger et al. | |
| 2016/0051315 A1 | 2/2016 | Boudreaux | |
| 2016/0051316 A1 | 2/2016 | Boudreaux | |
| 2016/0051317 A1 | 2/2016 | Boudreaux | |
| 2016/0058492 A1 | 3/2016 | Yates et al. | |
| 2016/0074108 A1 | 3/2016 | Woodruff et al. | |
| 2016/0128762 A1 | 5/2016 | Harris et al. | |
| 2016/0135875 A1 | 5/2016 | Strobl et al. | |
| 2016/0157927 A1 | 6/2016 | Corbett et al. | |
| 2016/0175024 A1 | 6/2016 | Yates et al. | |
| 2016/0175028 A1 | 6/2016 | Trees et al. | |
| 2016/0175029 A1 | 6/2016 | Witt et al. | |
| 2016/0175031 A1 | 6/2016 | Boudreaux | |
| 2016/0175032 A1 | 6/2016 | Yang | |
| 2016/0199123 A1 | 7/2016 | Thomas et al. | |
| 2016/0199125 A1 | 7/2016 | Jones | |
| 2016/0228171 A1 | 8/2016 | Boudreaux | |
| 2016/0270840 A1 | 9/2016 | Yates et al. | |
| 2016/0270841 A1 | 9/2016 | Strobl et al. | |
| 2016/0270842 A1 | 9/2016 | Strobl et al. | |
| 2016/0270843 A1 | 9/2016 | Boudreaux et al. | |
| 2016/0278848 A1 | 9/2016 | Boudreaux et al. | |
| 2016/0296268 A1 | 10/2016 | Gee et al. | |
| 2016/0296270 A1 | 10/2016 | Strobl et al. | |
| 2016/0296271 A1 | 10/2016 | Danziger et al. | |
| 2016/0302844 A1 | 10/2016 | Strobl et al. | |
| 2016/0317215 A1 | 11/2016 | Worrell et al. | |
| 2017/0105791 A1* | 4/2017 | Yates | A61B 18/1445 |

FOREIGN PATENT DOCUMENTS

| | | |
|---|---|---|
| DE | 4300307 A1 | 7/1994 |
| DE | 19608716 C1 | 4/1997 |
| DE | 29623113 U1 | 10/1997 |
| DE | 20004812 U1 | 9/2000 |
| DE | 10201569 A1 | 7/2003 |
| EP | 0340803 B1 | 8/1993 |
| EP | 0630612 A1 | 12/1994 |
| EP | 0705571 A1 | 4/1996 |
| EP | 0557806 B1 | 5/1998 |
| EP | 0640317 B1 | 9/1999 |
| EP | 0722696 B1 | 12/2002 |
| EP | 1293172 B1 | 4/2006 |
| EP | 0875209 B1 | 5/2006 |
| EP | 1704824 A1 | 9/2006 |
| EP | 1749479 A1 | 2/2007 |
| EP | 1767157 A1 | 3/2007 |
| EP | 1254637 B1 | 8/2007 |
| EP | 1878399 A1 | 1/2008 |
| EP | 1915953 A1 | 4/2008 |
| EP | 1532933 B1 | 5/2008 |
| EP | 1707143 B1 | 6/2008 |
| EP | 1943957 A2 | 7/2008 |
| EP | 1435852 B1 | 12/2008 |
| EP | 1849424 B1 | 4/2009 |
| EP | 2042117 A1 | 4/2009 |
| EP | 2060238 A1 | 5/2009 |
| EP | 1810625 B1 | 8/2009 |
| EP | 2090238 A1 | 8/2009 |
| EP | 2090256 A2 | 8/2009 |
| EP | 2092905 A1 | 8/2009 |
| EP | 2105104 A2 | 9/2009 |
| EP | 1747761 B1 | 10/2009 |
| EP | 1769766 B1 | 2/2010 |
| EP | 2151204 A1 | 2/2010 |
| EP | 2153791 A1 | 2/2010 |
| EP | 2243439 A1 | 10/2010 |
| EP | 1510178 B1 | 6/2011 |
| EP | 1728475 B1 | 8/2011 |
| EP | 2353518 A1 | 8/2011 |
| EP | 2436327 A1 | 4/2012 |
| EP | 2529681 A1 | 12/2012 |
| EP | 1767164 B1 | 1/2013 |
| EP | 2316359 B1 | 3/2013 |
| EP | 2578172 A2 | 4/2013 |
| EP | 2508143 B1 | 2/2014 |
| GB | 2472216 A | 2/2011 |
| JP | H 08-229050 A | 9/1996 |
| JP | 2008-018226 A | 1/2008 |
| JP | 5714508 B2 | 5/2015 |
| WO | WO 81/03272 A1 | 11/1981 |
| WO | WO 93/07817 A1 | 4/1993 |
| WO | WO 93/22973 A1 | 11/1993 |
| WO | WO 95/10978 A1 | 4/1995 |
| WO | WO 96/35382 A1 | 11/1996 |
| WO | WO 97/10764 A1 | 3/1997 |
| WO | WO 98/00069 A1 | 1/1998 |
| WO | WO 98/40020 A1 | 9/1998 |
| WO | WO 98/57588 A1 | 12/1998 |
| WO | WO 99/23960 A1 | 5/1999 |
| WO | WO 99/40857 A1 | 8/1999 |
| WO | WO 99/40861 A1 | 8/1999 |
| WO | WO 00/24330 A1 | 5/2000 |
| WO | WO 00/24331 A1 | 5/2000 |
| WO | WO 00/25691 A1 | 5/2000 |
| WO | WO 01/28444 A1 | 4/2001 |
| WO | WO 02/062241 A1 | 8/2002 |
| WO | WO 02/080797 A1 | 10/2002 |
| WO | WO 03/020339 A2 | 10/2002 |
| WO | WO 03/001986 A2 | 1/2003 |
| WO | WO 03/013374 A1 | 2/2003 |
| WO | WO 03/028541 A2 | 4/2003 |
| WO | WO 03/030708 A2 | 4/2003 |
| WO | WO 03/068046 A2 | 8/2003 |
| WO | WO 2004/011037 A2 | 2/2004 |
| WO | WO 2004/032754 A2 | 4/2004 |
| WO | WO 2004/032762 A1 | 4/2004 |
| WO | WO 2004/032763 A2 | 4/2004 |
| WO | WO 2004/078051 A2 | 9/2004 |
| WO | WO 2004/112618 A2 | 12/2004 |
| WO | WO 2005/052959 A2 | 6/2005 |
| WO | WO 2006/021269 A1 | 3/2006 |
| WO | WO 2006/036706 A1 | 4/2006 |
| WO | WO 2006/055166 A2 | 5/2006 |
| WO | WO 2006/119139 A2 | 11/2006 |
| WO | WO 2008/020964 A2 | 2/2008 |
| WO | WO 2008/045348 A2 | 4/2008 |
| WO | WO 2008/099529 A1 | 8/2008 |
| WO | WO 2008/101356 A1 | 8/2008 |
| WO | WO 2009/022614 A1 | 2/2009 |
| WO | WO 2009/036818 A1 | 3/2009 |
| WO | WO 2009/039179 A1 | 3/2009 |
| WO | WO 2009/059741 A1 | 5/2009 |
| WO | WO 2009/062477 A2 | 7/2009 |
| WO | WO 2009/149234 A1 | 12/2009 |
| WO | WO 2010/017266 A1 | 2/2010 |
| WO | WO 2010/104755 A1 | 9/2010 |
| WO | WO 2011/008672 A2 | 1/2011 |
| WO | WO 2011/044343 A2 | 4/2011 |
| WO | WO 2011/084768 A1 | 7/2011 |
| WO | WO 2011/089717 A1 | 7/2011 |
| WO | WO 2011/144911 A1 | 11/2011 |
| WO | WO 2012/044606 A2 | 4/2012 |
| WO | WO 2012/166510 A1 | 12/2012 |
| WO | WO 2013/034629 A1 | 3/2013 |
| WO | WO 2013/062978 A2 | 5/2013 |
| WO | WO 2013/102602 A2 | 7/2013 |
| WO | WO 2013/154157 A1 | 10/2013 |
| WO | WO 2015/197395 A8 | 12/2015 |

OTHER PUBLICATIONS

Weir, C.E., "Rate of shrinkage of tendon collagen—heat, entropy and free energy of activation of the shrinkage of untreated tendon.

(56) References Cited

OTHER PUBLICATIONS

Effect of acid salt, pickle, and tannage on the activation of tendon collagen." Journal of the American Leather Chemists Association, 44, pp. 108-140 (1949).
Hörmann et al., "Reversible and irreversible denaturation of collagen fibers." Biochemistry, 10, pp. 932-937 (1971).
Henriques. F.C., "Studies in thermal injury V. The predictability and the significance of thermally induced rate processes leading to irreversible epidermal injury." Archives of Pathology, 434, pp. 489-502 (1947).
Arnoczky et al., "Thermal Modification of Conective Tissues: Basic Science Considerations and Clinical Implications," J. Am Acad Orthop Surg, vol. 8, No. 5, pp. 305-313 (Sep./Oct. 2000).
Chen et al., "Heat-induced changes in the mechanics of a collagenous tissue: pseudoelastic behavior at 37° C.," Journal of Biomechanics, 31, pp. 211-216 (1998).
Chen et al., "Heat-Induced Changes in the Mechanics of a Collagenous Tissue: Isothermal Free Shrinkage," Transactions of the ASME, vol. 119, pp. 372-378 (Nov. 1997).
Chen et al., "Heat-Induced Changes in the Mechanics of a Collagenous Tissue: Isothermal, Isotonic Shrinkage," Transactions of the ASME, vol. 120, pp. 382-383 (Jun. 1993).
Chen et al., "Phenomenological Evolution Equations for Heat-Induced Shrinkage of a Collagenous Tissue," IEEE Transactions on Biomedical Engineering, vol. 45, No. 10, pp. 1234-1240 (Oct. 1998).
Harris et al., "Kinetics of Thermal Damage to a Collagenous Membrane Under Biaxial Isotonic Loading," IEEE Transactions on Biomedical Engineering, vol. 51, No. 2, pp. 371-379 (Feb. 2004).
Harris et al., "Altered Mechanical Behavior of Epicardium Due to Isothermal Heating Under Biaxial Isotonic Loads," Journal of Biomechanical Engineering, vol. 125, pp. 381-388 (Jun. 2003).
Hayashi et al., "The Effect of Thermal Heating on the Length and Histologic Properties of the Glenohumeral Joint Capsule," American Journal of Sports Medicine, vol. 25, Issue 1, 11 pages (Jan. 1997), URL: http://www.mdconsult.com/das/article/body/156183648-2/jorg=journal&source=MI&sp=1 . . . , accessed Aug. 25, 2009.
Lee et al., "A multi-sample denaturation temperature tester for collagenous biomaterials," Med. Eng. Phy., vol. 17, No. 2, pp. 115-121 (Mar. 1995).
Moran et al., "Thermally Induced Shrinkage of Joint Capsule," Clinical Orthopaedics and Related Research, No. 281, pp. 248-255 (Dec. 2000).
Wall et al., "Thermal modification of collagen," J Shoulder Elbow Surg, No. 8, pp. 339-344 (Jul./Aug. 1999).
Wells et al., "Altered Mechanical Behavior of Epicardium Under Isothermal Biaxial Loading," Transactions of the ASME, Journal of Biomechanical Engineering, vol. 126, pp. 492-497 (Aug. 2004).

Gibson, "Magnetic Refrigerator Successfully Tested," U.S. Department of Energy Research News, accessed online on Aug. 6, 2010 at http://www.eurekalert.org/features/doe/2001-11/dl-mrs062802.php (Nov. 1, 2001).
Humphrey, J.D., "Continuum Thermomechanics and the Clinical Treatment of Disease and Injury," Appl. Mech. Rev., vol. 56, No. 2 pp. 231-260 (Mar. 2003).
Kurt Gieck & Reiner Gieck, *Engineering Formulas* § Z.7 (7th ed. 1997).
National Semiconductors Temperature Sensor Handbook—http://www.national.com/appinfo/tempsensors/files/temphb.pdf; accessed online: Apr. 1, 2011.
Glaser and Subak-Sharpe, *Integrated Circuit Engineering*, Addison-Wesley Publishing, Reading, MA (1979).
Wright, et al., "Time-Temperature Equivalence of Heat-Induced Changes in Cells and Proteins," Feb. 1998. ASME Journal of Biomechanical Engineering, vol. 120, pp. 22-26.
Covidien Brochure, [Value Analysis Brief], LigaSure Advance™ Pistol Grip, dated Rev. Apr. 2010 (7 pages).
Covidien Brochure, LigaSure Impact™ Instrument LF4318, dated Feb. 2013 (3 pages).
Covidien Brochure, LigaSure Atlas™ Hand Switching Instruments, dated Dec. 2008 (2 pages).
Covidien Brochure, The LigaSure™ 5 mm Blunt Tip Sealer/Divider Family, dated Apr. 2013 (2 pages).
Covidien Brochure, The LigaSure Precise™ Instrument, dated Mar. 2011 (2 pages).
Erbe Electrosurgery Vio® 200 S, (2012), p. 7, 12 pages, accessed Mar. 31, 2014 at http://www.erbe-med.com/erbe/media/Marketingmaterialien/85140-170_ERBE_EN_VIO_200_S_D027541.
Jang, J. et al. "Neuro-fuzzy and Soft Computing." Prentice Hall, 1997, pp. 13-89, 199-293, 335-393,453-496, 535-549.
Douglas, S.C. "Introduction to Adaptive Filter". Digital Signal Processing Handbook. Ed. Vijay K. Madisetti and Douglas B. Williams. Boca Raton: CRC Press LLC, 1999.
Sullivan, "Cost-Constrained Selection of Strand Diameter and Number in a Litz-Wire Transformer Winding," IEEE Transactions on Power Electronics, vol. 16, No. 2, Mar. 2001, pp. 281-288.
Sullivan, "Optimal Choice for Number of Strands in a Litz-Wire Transformer Winding," IEEE Transactions on Power Electronics, vol. 14, No. 2, Mar. 1999, pp. 283-291.
https://www.kjmagnetics.com/fieldcalculator.asp, retrieved Jul. 11, 2016, backdated to Nov. 11, 2011 via https://web.archive.org/web/20111116164447/http://www.kjmagnetics.com/fieldcalculator.asp.
Leonard I. Malis, M.D., "The Value of Irrigation During Bipolar Coagulation," 1989.
Dean, D.A., "Electrical Impedance Spectroscopy Study of Biological Tissues," J. Electrostat 66(34), Mar. 2008, pp. 165-177. Accessed Apr. 10, 2018: https://www.ncbi.nlm.nih.gov/pmc/articles/PMC2597841/.

* cited by examiner

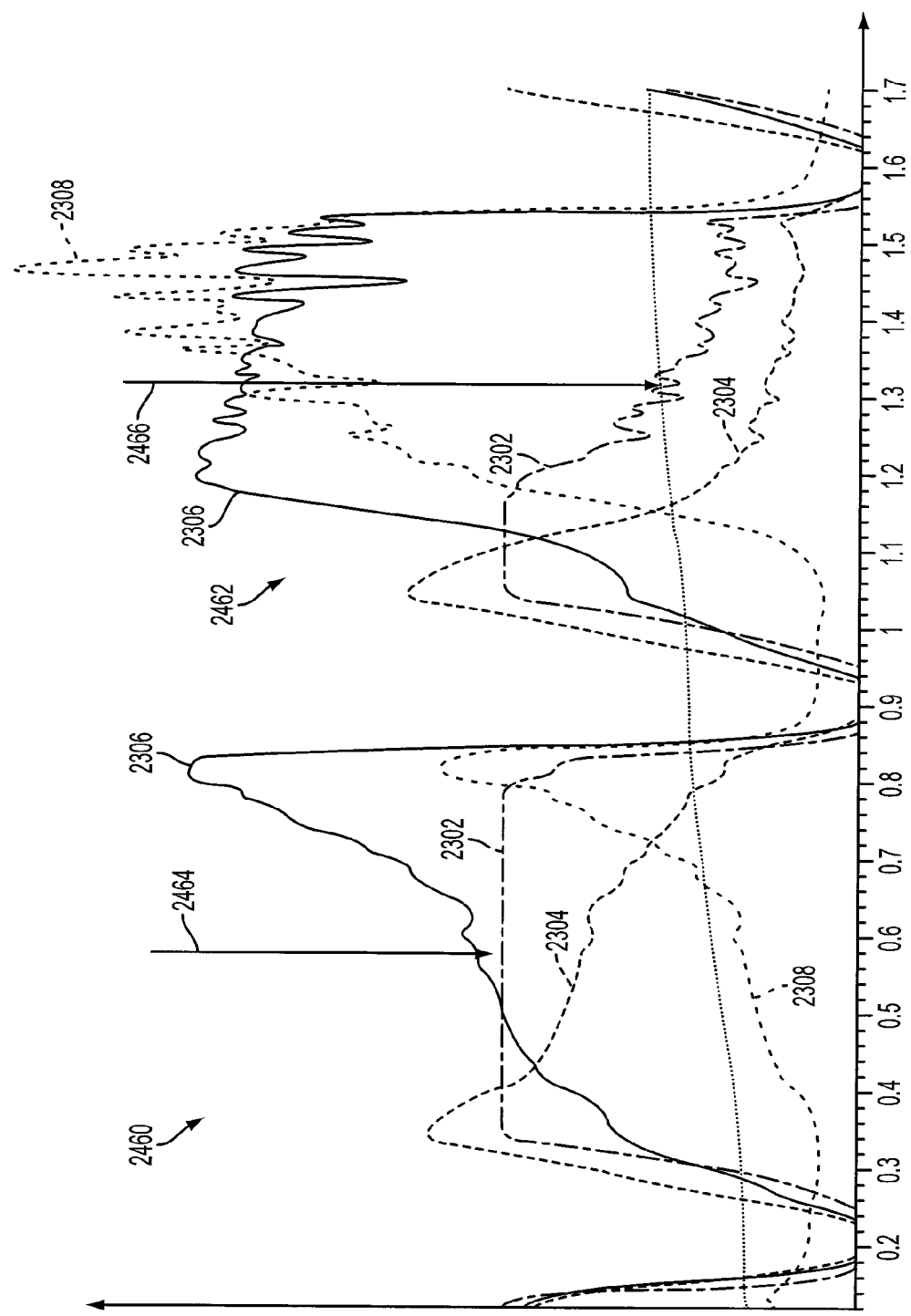

MANAGING TISSUE TREATMENT

BACKGROUND

Various embodiments are directed to surgical systems that may be utilized in electrosurgical and/or ultrasonic devices to manage the delivery of energy to tissue to optimize tissue treatment.

Electrosurgical devices for applying electrical energy to tissue in order to treat and/or destroy the tissue are commonly used in surgical procedures. An electrosurgical device may comprise a hand piece and an instrument having a distally-mounted end effector (e.g., one or more electrodes). The end effector can be positioned against the tissue such that electrical current is introduced into the tissue. Electrosurgical devices can be configured for bipolar or monopolar operation. During bipolar operation, current is introduced into and returned from the tissue by active and return electrodes, respectively, of the end effector. During monopolar operation, current is introduced into the tissue by an active electrode of the end effector and returned through a return electrode (e.g., a grounding pad) separately located on a patient's body. Heat generated by the current flow through the tissue may form hemostatic seals within the tissue and/or between tissues and thus may be particularly useful for sealing blood vessels, for example. The end effector of an electrosurgical device may also comprise a cutting member that is movable relative to the tissue and the electrodes to transect the tissue.

Electrical energy applied by an electrosurgical device can be transmitted to the instrument by a generator in communication with the hand piece. The electrical energy may be in the form of radio frequency ("RF") energy. RF energy is a form of electrical energy that may be in the frequency range of 300 kHz to 1 MHz. During its operation, an electrosurgical device can transmit low frequency RF energy through tissue, which causes ionic agitation, or friction, in effect resistive heating, thereby increasing the temperature of the tissue. Because a sharp boundary may be created between the affected tissue and the surrounding tissue, surgeons can operate with a high level of precision and control, without sacrificing un-targeted adjacent tissue. The low operating temperatures of RF energy may be useful for removing, shrinking, or sculpting soft tissue while simultaneously sealing blood vessels. RF energy may work particularly well on connective tissue, which is primarily comprised of collagen and shrinks when contacted by heat.

Ultrasonic surgical devices, such as ultrasonic scalpels, are another type of powered surgical devices used in surgical procedures. Depending upon specific device configurations and operational parameters, ultrasonic surgical devices can provide substantially simultaneous transection of tissue and homeostasis by coagulation, desirably minimizing patient trauma. An ultrasonic surgical device may comprise a hand piece containing an ultrasonic transducer, and an instrument coupled to the ultrasonic transducer having a distally-mounted end effector (e.g., a blade tip) to cut and seal tissue. In some cases, the instrument may be permanently affixed to the hand piece. In other cases, the instrument may be detachable from the hand piece, as in the case of a disposable instrument or an instrument that is interchangeable between different hand pieces. The end effector transmits ultrasonic energy to tissue brought into contact with the end effector to realize cutting and sealing action. Ultrasonic surgical devices of this nature can be configured for open surgical use, laparoscopic, or endoscopic surgical procedures including robotic-assisted procedures.

Ultrasonic energy cuts and coagulates tissue using frictional heating and can be transmitted to the end effector by an ultrasonic generator in communication with the hand piece. Vibrating at high frequencies (e.g., 55,500 times per second), the ultrasonic blade denatures protein in the tissue to form a sticky coagulum. Pressure exerted on tissue by the blade surface collapses blood vessels and allows the coagulum to form a hemostatic seal. A clinician can control the cutting speed and coagulation by the force applied to the tissue by the end effector, the time over which the force is applied and the selected excursion level of the end effector.

Electrosurgical and ultrasonic devices that operate in conjunction with an external generator typically do not carry an on-board power supply. This limits the functionality that can be provided by the devices themselves. For example, in generator-connected surgical devices it is not currently feasible to include components that consume high levels of power such as, for example, motors, powered sensors, microprocessors, etc.

SUMMARY

Various embodiments are directed to systems and methods for providing a drive signal to a surgical device for treating tissue. A surgical generator may deliver the drive signal according to a first composite load curve. The surgical generator may receive a first tissue measurement indicating a property of the tissue at a first time during the delivery of the drive signal, receive a second tissue measurement indicating the property of the tissue at a second time during the delivery of the drive signal after the first time, and based on the first and second tissue measurements, determine a difference in the property of the tissue between the first time and the second time. When the difference in the property of the tissue exceeds a difference threshold, the generator may deliver the drive signal according to a second composite load curve that is more aggressive than the first composite load curve.

Also, various embodiments are directed to systems and methods for providing a drive signal to a surgical device for treating tissue. A surgical generator may receive a first tissue measurement indicating a property of the tissue. Based on the first tissue measurement, the surgical generator may select a first power curve that defines a first level of power to be delivered to the tissue as a function of at least one measured property of the tissue.

FIGURES

The novel features of the various embodiments are set forth with particularity in the appended claims. The described embodiments, however, both as to organization and methods of operation, may be best understood by reference to the following description, taken in conjunction with the accompanying drawings in which:

FIG. 25B illustrates a plot showing various properties of one embodiment of a drive signal showing two pulses.

DESCRIPTION

Before explaining various embodiments of surgical devices and generators in detail, it should be noted that the illustrative embodiments are not limited in application or use to the details of construction and arrangement of parts illustrated in the accompanying drawings and description. The illustrative embodiments may be implemented or incorporated in other embodiments, variations and modifications, and may be practiced or carried out in various ways. Further, unless otherwise indicated, the terms and expressions employed herein have been chosen for the purpose of describing the illustrative embodiments for the convenience of the reader and are not for the purpose of limitation thereof. Also, it will be appreciated that one or more of the following-described embodiments, expressions of embodiments and/or examples, can be combined with any one or more of the other following-described embodiments, expressions of embodiments and/or examples.

Various embodiments are directed to surgical devices and/or associated surgical generators (e.g., surgical systems) for treating tissue. For example, generators described herein may be programmed to increment and/or decrement a power curve applied to tissue via a drive signal based on changes in tissue properties. For example, if tissue impedance changes by more than an impedance change threshold indicating that the drive signal is not having a sufficient effect on tissue, the generator may increment to apply a more aggressive power curve. If tissue impedance changes by more than a second impedance change threshold indicating that the drive signal is having too much of an effect on tissue, the generator may decrement the power curve to apply a less aggressive power curve. Changes in various other tissue properties, or proxies therefor, may be used to determine whether to increment or decrement an applied power curve including, for example, a power difference. Incrementing or decrementing power curves based on changes in tissue property may be implemented in parallel with other process flows for managing the application of power curves, including algorithms that increment power curves based on, for example, total energy applied, tissue impedance, the application of a defined set of pulses, etc. Also, in some embodiments, the generator 102, 220 may be programmed to determine an initial power curve, for example, based on a measured tissue property such as impedance, etc.

It will be appreciated that the terms "proximal" and "distal" are used herein with reference to a clinician gripping a hand piece. Thus, an end effector is distal with respect to the more proximal hand piece. It will be further appreciated that, for convenience and clarity, spatial terms such as "top" and "bottom" may also be used herein with respect to the clinician gripping the hand piece. However, surgical devices are used in many orientations and positions, and these terms are not intended to be limiting and absolute.

Figure 1:
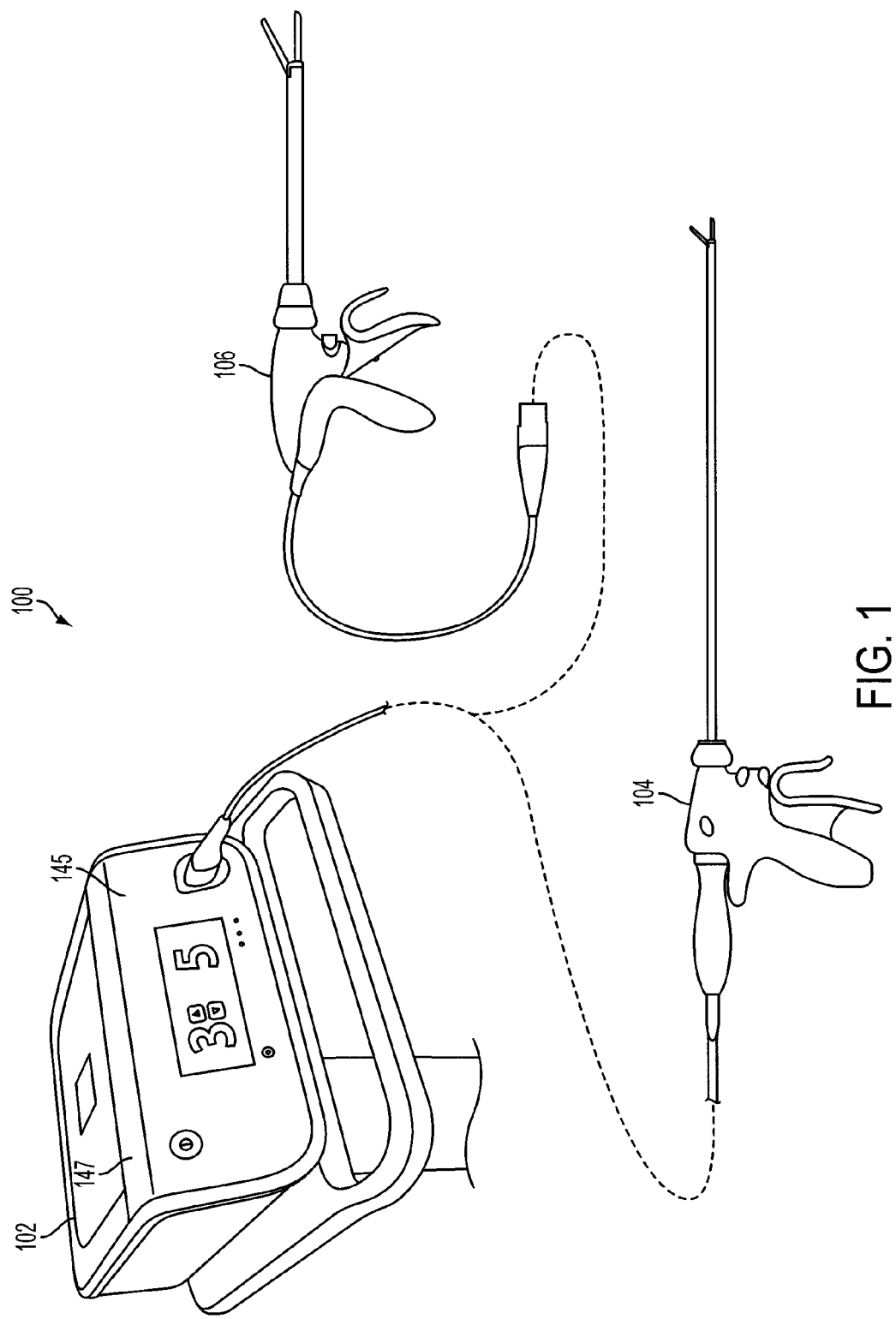
FIG. 1 illustrates one embodiment of a surgical system comprising a generator and various surgical devices usable therewith.

FIG. 1 illustrates one embodiment of a surgical system 100 comprising a generator 102 configurable for use with surgical devices. According to various embodiments, the generator 102 may be configurable for use with surgical devices of different types, including, for example, the ultrasonic surgical device 104 and electrosurgical or RF surgical device 106. Although in the embodiment of FIG. 1 the generator 102 is shown separate from the surgical devices 104, 106, in certain embodiments the generator 102 may be formed integrally with either of the surgical devices 104, 106 to form a unitary surgical system.

Figure 2:
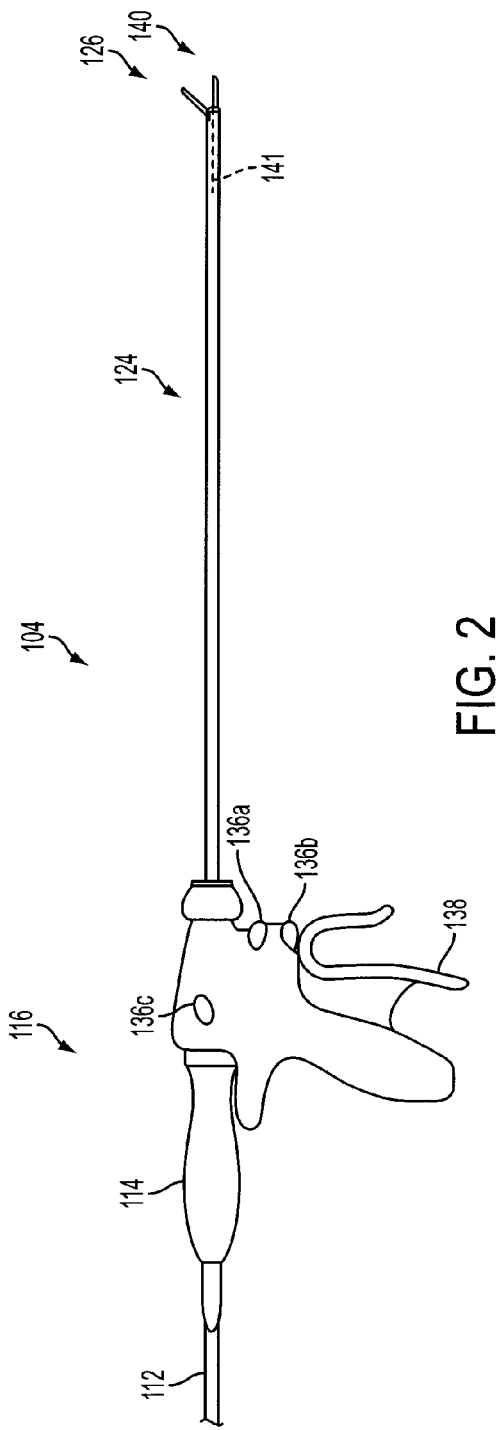
FIG. 2 illustrates one embodiment of an example ultrasonic device that may be used for transection and/or sealing.

FIG. 2 illustrates one embodiment of an example ultrasonic device 104 that may be used for transection and/or sealing. The device 104 may comprise a hand piece 116 which may, in turn, comprise an ultrasonic transducer 114. The transducer 114 may be in electrical communication with the generator 102, for example, via a cable 112 (e.g., a multi-conductor cable). The transducer 114 may comprise piezoceramic elements, or other elements or components suitable for converting the electrical energy of a drive signal into mechanical vibrations. When activated by the generator 102, the ultrasonic transducer 114 may cause longitudinal vibration. The vibration may be transmitted through an instrument portion 124 of the device 104 (e.g., via a waveguide embedded in an outer sheath) to an end effector 126 of the instrument portion 124.

Figure 3:
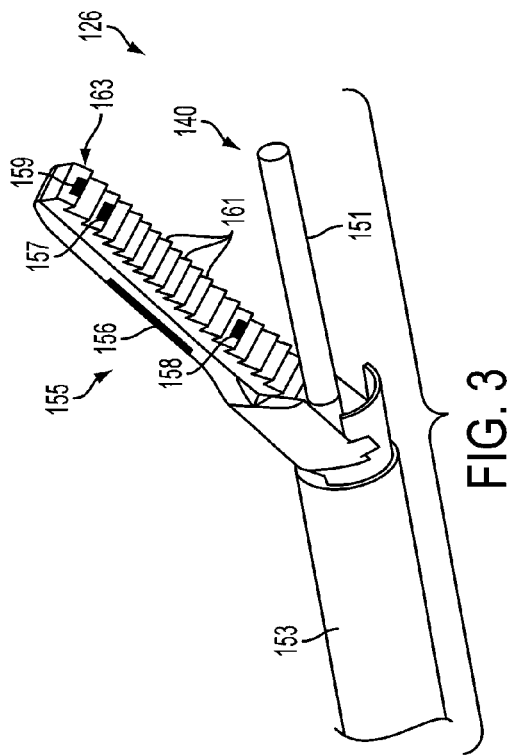
FIG. 3 illustrates one embodiment of the end effector of the example ultrasonic device of FIG. 2.

FIG. 3 illustrates one embodiment of the end effector 126 of the example ultrasonic device 104. The end effector 126 may comprise a blade 151 that may be coupled to the ultrasonic transducer 114 via the wave guide (not shown). When driven by the transducer 114, the blade 151 may vibrate and, when brought into contact with tissue, may cut and/or coagulate the tissue, as described herein. According to various embodiments, and as illustrated in FIG. 3, the end effector 126 may also comprise a clamp arm 155 that may be configured for cooperative action with the blade 151 of the end effector 126. With the blade 151, the clamp arm 155 may comprise a set of jaws 140. The clamp arm 155 may be pivotally connected at a distal end of a shaft 153 of the instrument portion 124. The clamp arm 155 may include a clamp arm tissue pad 163, which may be formed from TEFLON® or other suitable low-friction material. The pad 163 may be mounted for cooperation with the blade 151, with pivotal movement of the clamp arm 155 positioning the clamp pad 163 in substantially parallel relationship to, and in contact with, the blade 151. By this construction, a tissue bite to be clamped may be grasped between the tissue pad 163 and the blade 151. In some embodiments, a strain gauge 156 or other pressure sensor may be positioned on the clamp arm 155, for example, between the clamp pad 163 and clamp arm 155, to measure the pressure exerted on tissue held between the clamp arm 155 and the blade 151. Also, in some embodiments, the clamp arm 155 may comprise a temperature sensor 158 for sensing a temperature of tissue between the clamp arm 155 and the blade 151. The temperature sensor 158 may be, for example, a thermocouple, a resistive temperature device, an infrared sensor, a bimetallic device, etc.

The tissue pad 163 may be provided with a sawtooth-like configuration including a plurality of axially spaced, proximally extending gripping teeth 161 to enhance the gripping of tissue in cooperation with the blade 151. The clamp arm 155 may transition from the open position shown in FIG. 3 to a closed position (with the clamp arm 155 in contact with or proximity to the blade 151) in any suitable manner. For example, the hand piece 116 may comprise a jaw closure trigger 138. When actuated by a clinician, the jaw closure trigger 138 may pivot the clamp arm 155 in any suitable manner. For example, the jaw closure trigger 138 may be coupled to a jaw closure member 141 extending through the shaft 124 to the clamp arm 155. Proximal motion of the jaw closure trigger 138 may cause corresponding proximal motion of the jaw closure member 141, which may pull the clamp arm 155 towards the blade.

Figure 8:
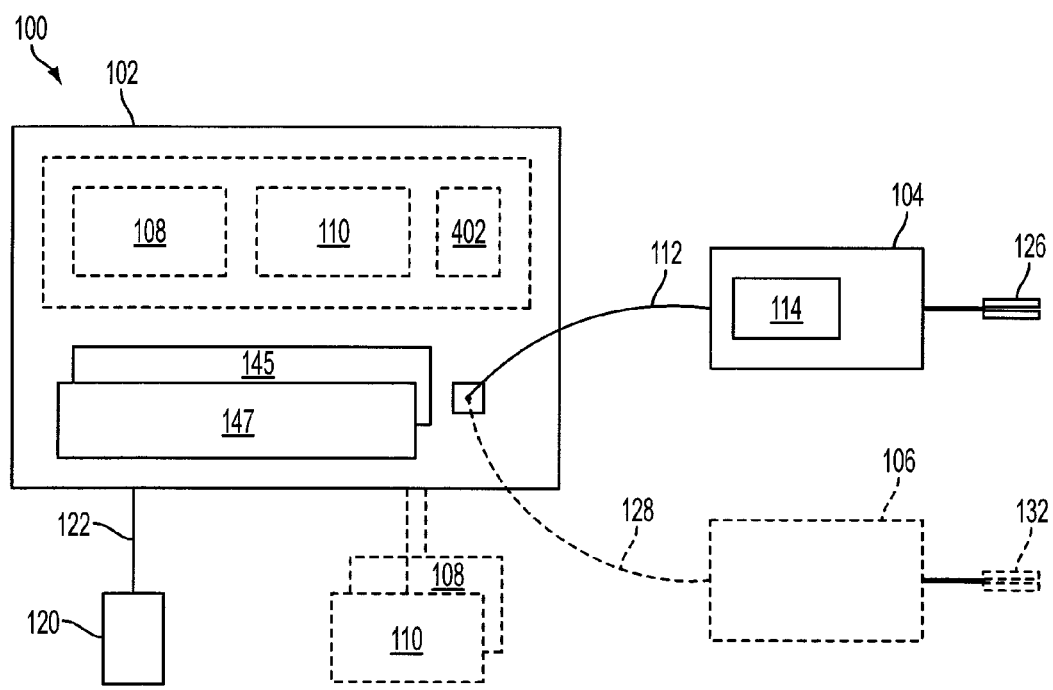
FIG. 8 illustrates one embodiment of the surgical system of FIG. 1.

The generator 102 may be activated to provide the drive signal to the transducer 114 in any suitable manner. For example, the generator 102 may comprise a foot switch 120 coupled to the generator 102 via a footswitch cable 122 (FIGS. 1, 8). A clinician may activate the transducer 114, and thereby the blade 151, by depressing the foot switch 120. In addition, or instead of the foot switch 120 some embodiments of the device 104 may utilize one or more switches or buttons positioned on the hand piece 116 that, when activated, may cause the generator 102 to activate the transducer 114. In some embodiments, the hand piece 116 may comprise a pair of buttons 136a, 136b positioned relative to the closure trigger 138 to allow the clinician to operate the buttons 136a, 136b with an index finger, for example, while gripping the closure trigger 138. In other embodiments, the buttons 136a, 136b may be replaced with a single similarly located button. Also, for example, one or more additional buttons, such as 136c, may be positioned on an upper portion of the hand piece 116. For example, the button 136c may be configured to, when depressed, cause the generator 102 to provide a pulsed output. The pulses may be provided at any suitable frequency and grouping, for example. In certain embodiments, the power level of the pulses may be the power levels set utilizing buttons 136a, 136b, as described above. Also, in some embodiments, the generator 102 may be activated based on the position of the jaw closure trigger 138, (e.g., as the clinician depresses the jaw closure trigger 138 to close the jaws 140, ultrasonic energy may be applied).

The various buttons 136a, 136b, 136c may be hardwired and/or programmable to, when depressed, bring about various effects on the drive signal provided to the transducer 114. For example, in some embodiments, the state of the buttons 136a, 136b may be communicated to the generator 102. In response to the state of the buttons, the generator 102 may determine an operating mode of the device 104, expressed as the form of the drive signal provided by the generator 102. When the button 136a is depressed, for example, the ultrasonic generator 102 may provide a maximum drive signal to the transducer 114, causing it to produce maximum ultrasonic energy output. Depressing button 136b may cause the generator 102 to provide a user-selectable drive signal to the transducer 114, causing it to produce less than the maximum ultrasonic energy output.

It will be appreciated that the ultrasonic device 104 may comprise any combination of the buttons 136a, 136b, 136c. For example, the device 104 could be configured to have only two buttons: a button 136a for producing maximum ultrasonic energy output and a button 136c for producing a pulsed output at either the maximum or less than maximum power level per. In this way, the drive signal output configuration of the generator 102 could be 5 continuous signals and 5 or 4 or 3 or 2 or 1 pulsed signals. In certain embodiments, the specific drive signal configuration may be controlled based upon, for example, EEPROM settings in the generator 102 and/or user power level selection(s).

In certain embodiments, a two-position switch may be provided as an alternative to a button 136c. For example, a device 104 may include a button 136a for producing a continuous output at a maximum power level and a two-position button 136b. In a first detented position, button 136b may produce a continuous output at a less than maximum power level, and in a second detented position the button 136b may produce a pulsed output (e.g., at either a maximum or less than maximum power level, depending upon the EEPROM settings).

In some embodiments, the end effector 126 may also comprise a pair of electrodes 159, 157. The electrodes 159, 157 may be in communication with the generator 102, for example, via the cable 128. The electrodes 159, 157 may be used, for example, to measure an impedance of a tissue bite present between the clamp arm 155 and the blade 151. The generator 102 may provide a signal (e.g., a non-therapeutic signal) to the electrodes 159, 157. The impedance of the tissue bite may be found, for example, by monitoring the current, voltage, etc. of the signal. In some embodiments, the non-therapeutic signal provided to the electrodes 159, 157 may be provided by the surgical device 106 itself.

Figure 3A:
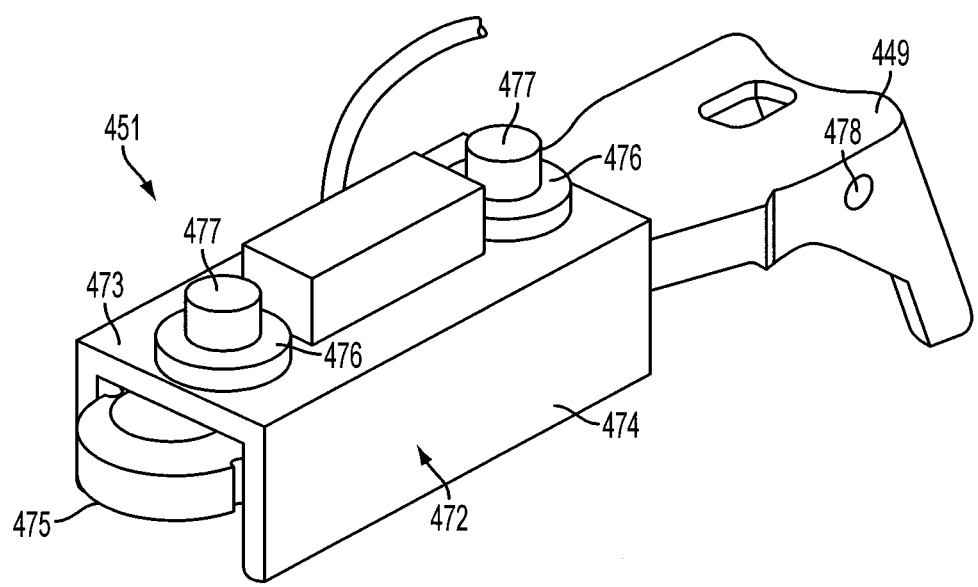
FIG. 3A illustrates one embodiment of a clamp arm assembly that may be employed with the ultrasonic device of FIG. 2.

FIG. 3A illustrates one embodiment of the clamp arm assembly 451 that may be employed with the ultrasonic device 104. In the illustrated embodiment, the clamp arm assembly 451 comprises a conductive jacket 472 mounted to a base 449. The conductive jacket 472 is the electrically conductive portion of the clamp arm assembly 451 that forms the second, e.g., return, electrode. In one implementation, the clamp arm 155 (FIG. 3) may form the base 449 on which the conductive jacket 472 is mounted. In various embodiments, the conductive jacket 472 may comprise a center portion 473 and at least one downwardly-extending sidewall 474 which can extend below the bottom surface 475 of the base 449. In the illustrated embodiment, the conductive jacket 472 has two sidewalls 474 extending downwardly on opposite sides of the base 449. In other embodiments, the center portion 473 may comprise at least one aperture 476 which can be configured to receive a projection 477 extending from the base 449. In such embodiments, the projections 477 can be press-fit within the apertures 476 in order to secure the conductive jacket 472 to the base 449. In other embodiments, the projections 477 can be deformed after they are inserted into the apertures 476. In various embodiments, fasteners can be used to secure the conductive jacket 472 to the base 449.

In various embodiments, the clamp arm assembly 451 comprises a non-electrically conductive or insulating material, such as plastic and/or rubber, for example, positioned intermediate the conductive jacket 472 and the base 449. The electrically insulating material can prevent current from flowing, or shorting, between the conductive jacket 472 and the base 449. In various embodiments, the base 449 may comprise at least one aperture 478, which can be configured to receive a pivot pin (not illustrated). The pivot pin can be configured to pivotably mount the base 449 to the shaft 153 (FIG. 3), for example, such that the clamp arm assembly 451 can be rotated between open and closed positions relative to the shaft 153. In the illustrated embodiment, the base 449 includes two apertures 478 positioned on opposite sides of the base 449. In one embodiment, a pivot pin may be formed of or may comprise a non-electrically conductive or insulating material, such as plastic and/or rubber, for example, which can be configured to prevent current from flowing into the shaft 153 even if the base 449 is in electrical contact with the conductive jacket 472, for example. Additional clamp arm assemblies comprising various embodiments of electrodes may be employed. Examples of such clamp arm assemblies are described in commonly-owned and contemporaneously-filed U.S. patent application Ser. Nos. 12/503,769, 12/503,770, and 12/503,766, each of which is incorporated herein by reference in its entirety.

Figure 3B:
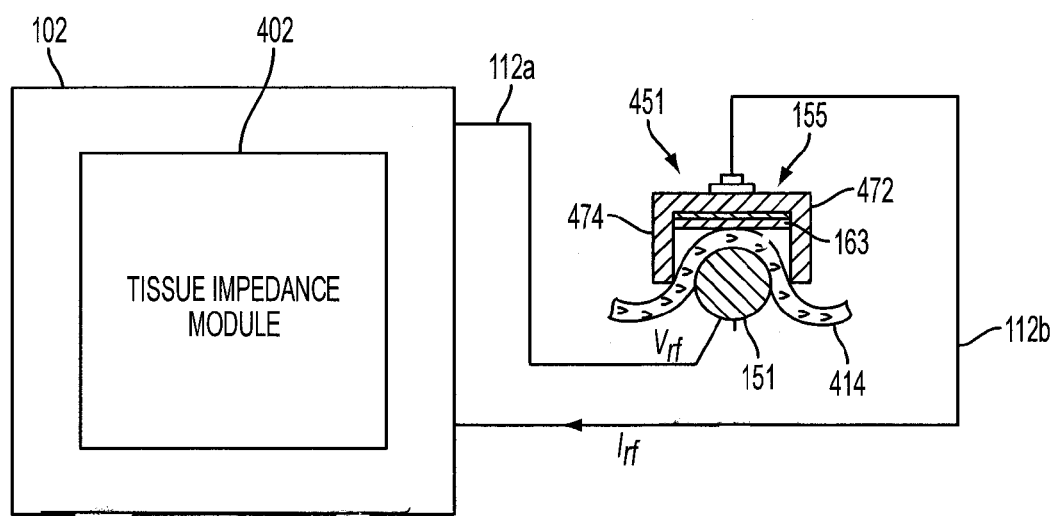
FIG. 3B is a schematic diagram of a tissue impedance module of the generator of FIG. 1 coupled to the blade and the clamp arm assembly of FIGS. 3 and 3A with tissue located therebetween.

FIG. 3B is a schematic diagram of the tissue impedance module 402 coupled to the blade 151 and the clamp arm assembly 451 with tissue 414 located therebetween. With reference now to FIGS. 1-3, the generator 102 may comprise a tissue impedance module 402 configured for monitoring the impedance of the tissue 414 (Z) located between the blade 151 and the clamp arm assembly 451 during the tissue transection process. The tissue impedance module 402 is coupled to the ultrasonic device 104 by way of the cable 112. The cable 112 includes a first "energizing" conductor 112a connected to the blade 151 (e.g., positive [+] electrode) and a second "return" conductor 112b connected to the conductive jacket 472 (e.g., negative [−] electrode) of the clamp arm assembly 451. In some embodiments, the generator 102 may provide a drive signal to the transducer on the conductors 112a, 112b and/or over additional conductors included in the cable 112. In one embodiment, RF voltage $v_{rf}$ is applied to the blade 151 to cause RF current $i_{rf}$ to flow through the tissue 414. The second conductor 112b provides the return path for the current $i_{rf}$ back to the tissue impedance module 402. The distal end of the return conductor 112b is connected to the conductive jacket 472 such that the current $i_{rf}$ can flow from the blade 151, through the tissue 414 positioned intermediate the conductive jacket 472 and the blade 151 and the conductive jacket 472 to the return conductor 112b. The impedance module 402 connects in circuit, by way of the first and second conductors 112a, b. In one embodiment, the RF energy may be applied to the blade 151 through the ultrasonic transducer 114 and the waveguide (not shown). In some embodiments, the RF energy applied to the tissue 414 for purposes of measuring the tissue impedance $Z_t$ is a low level subtherapeutic signal that does not contribute in a significant manner, or at all, to the treatment of the tissue 414.

Figure 4:
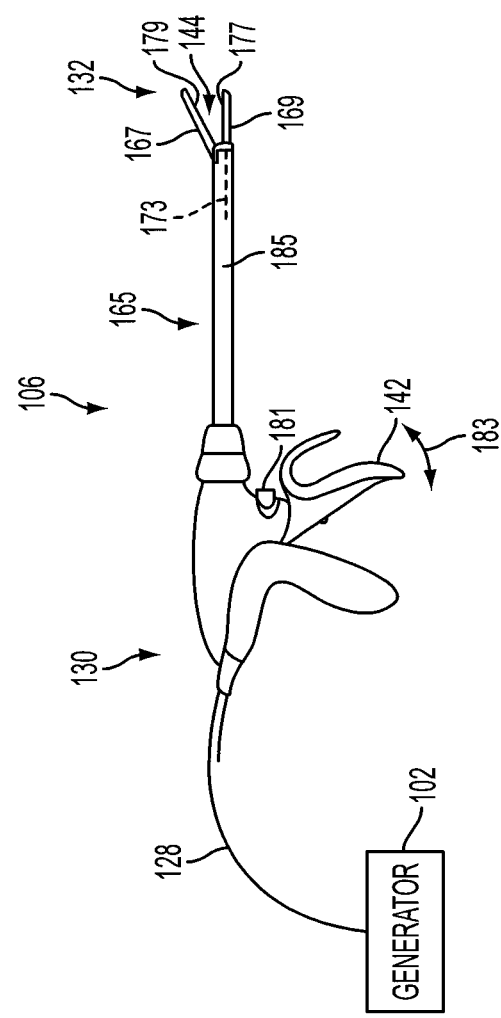
FIG. 4 illustrates one embodiment of an example electrosurgical device that may also be used for transection and sealing.

FIG. 4 illustrates one embodiment of an example electrosurgical device 106 that may also be used for transection and sealing. According to various embodiments, the transection and sealing device 106 may comprise a hand piece assembly 130, an elongated shaft 165 and an end effector 132. The shaft 165 may be rigid, as shown, (e.g., for laparoscopic and/or open surgical application) or flexible, (e.g., for endoscopic application). In various embodiments, the shaft 165 may comprise one or more articulation points. The end effector 132 may comprise jaws 144 having a first jaw member 167 and a second jaw member 169. A translating member 173 may extend within the shaft 165 from the end effector 132 to the hand piece 130. At the hand piece 130, the shaft 165 may be directly or indirectly coupled to a jaw closure trigger 142 (FIG. 4).

The jaw members 167, 169 of the end effector 132 may comprise respective electrodes 177, 179. The electrodes 177, 179 may be connected to the generator 102 via electrical leads 187a, 187b (FIG. 5) extending from the end effector 132 through the shaft 165 and hand piece 130 and ultimately to the generator 102 (e.g., by a multi-conductor cable 128). The generator 102 may provide a drive signal to the electrodes 177, 179 to bring about a therapeutic effect to tissue present within the jaw members 167, 169. The electrodes 177, 179 may comprise an active electrode and a return electrode, wherein the active electrode and the return electrode can be positioned against, or adjacent to, the tissue to be treated such that current can flow from the active electrode to the return electrode through the tissue. As illustrated in FIG. 4, the end effector 132 is shown with the jaw members 167, 169 in an open position.

Figure 5:
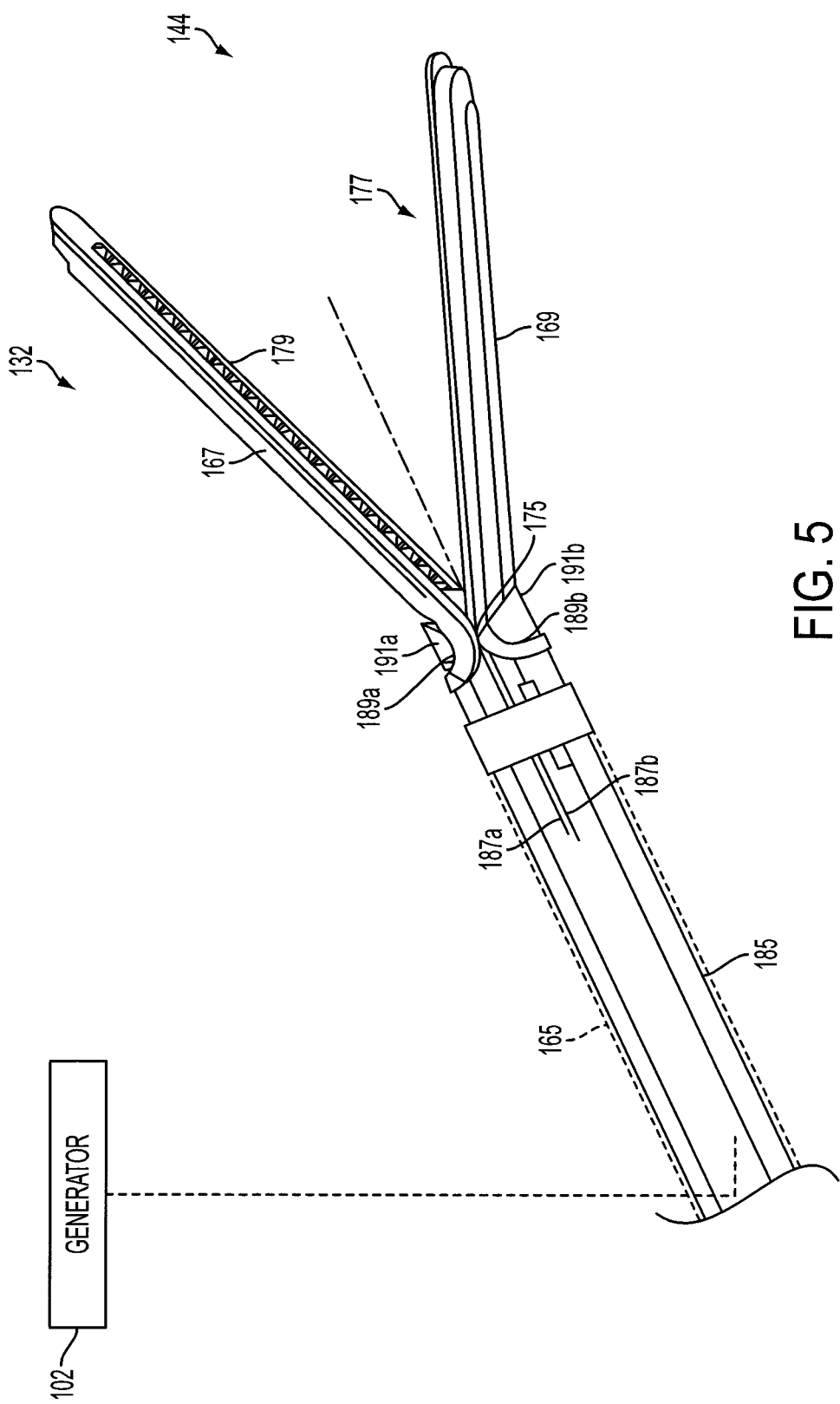
FIGS. 5, 6 and 7 illustrate one embodiment of the end effector shown in FIG. 4.
Figure 6:
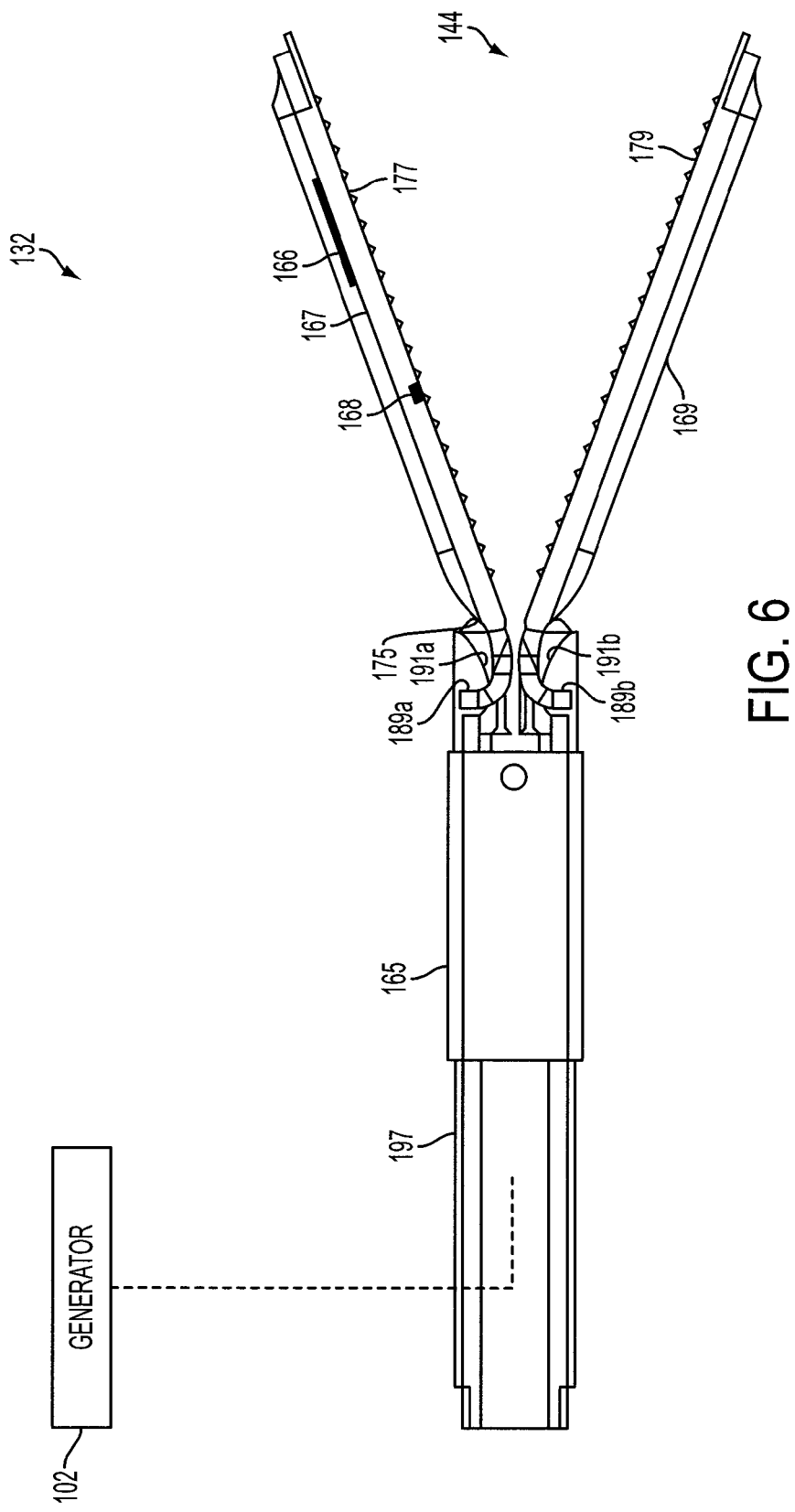
Figure 7:
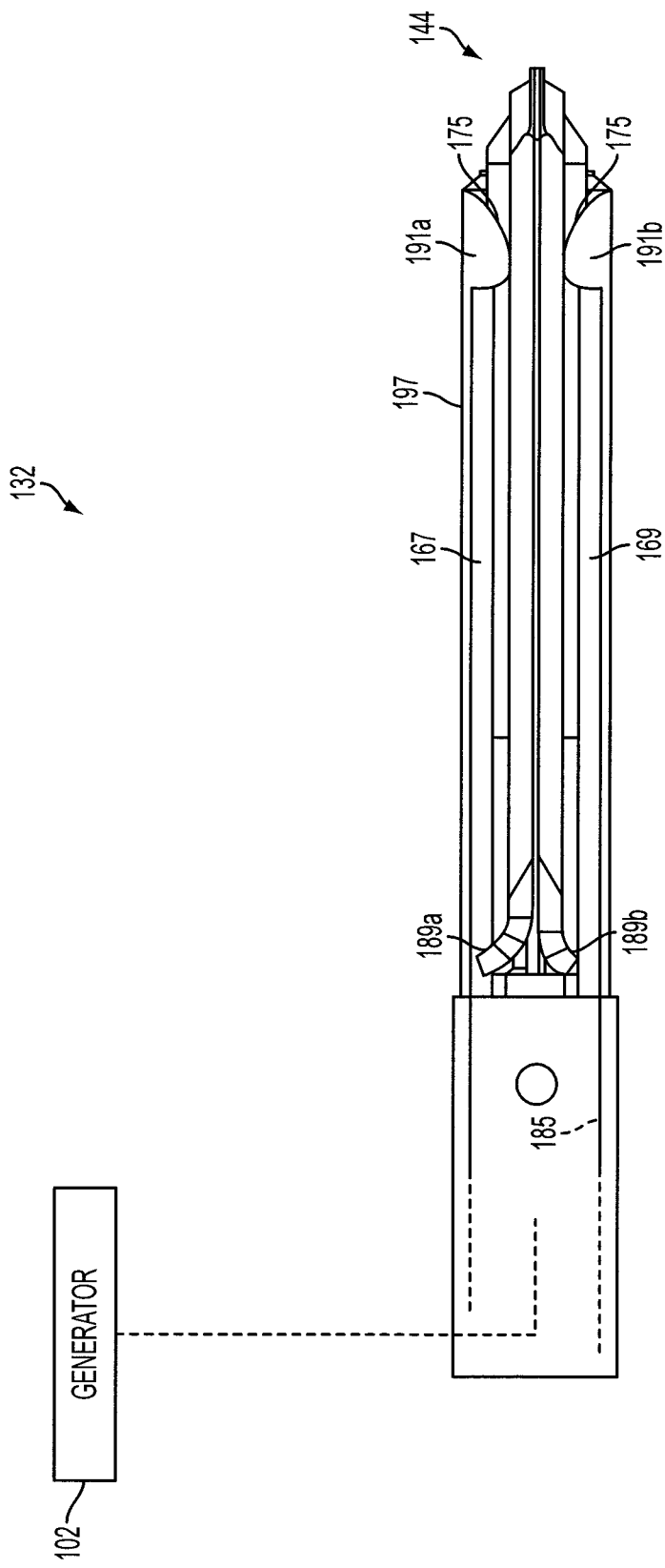

FIGS. 5, 6 and 7 illustrate one embodiment of the end effector 132 shown in FIG. 4. To close the jaws 144 of the end effector 132, a clinician may cause the jaw closure trigger 142 to pivot along arrow 183 (FIG. 4) from a first position to a second position. This may cause the jaws 144 to open and close according to any suitable method. For example, motion of the jaw closure trigger 142 may, in turn, cause the translating member 173 to translate within a bore 185 of the shaft 165. A distal portion of the translating member 173 may be coupled to a reciprocating member 197 such that distal and proximal motion of the translating member 173 causes corresponding distal and proximal motion of the reciprocating member. The reciprocating member 197 may have shoulder portions 191a, 191b, while the jaw members 167, 169 may have corresponding cam surfaces 189a, 189b. As the reciprocating member 197 is translated distally from the position shown in FIG. 6 to the position shown in FIG. 7, the shoulder portions 191a, 191b may contact the cam surfaces 189a, 189b, causing the jaw members 167, 169 to transition to the closed position. Also, in various embodiments, the blade 175 may be positioned at a distal end of the reciprocating member 197. As the reciprocating member 197 extends to the fully distal position shown in FIG. 7, the blade 175 may be pushed through any tissue present between the jaw members 167, 169, in the process, severing it. In some embodiments, a strain gauge 166 or any other suitable pressure sensor may be placed on the jaw member 167 and/or the jaw member 169 to measure the pressure placed on tissue by the respective jaw members 167, 169 during tissue treatment (FIG. 6). Also, in some embodiments, one or both of the jaw members 167, 169 may comprise a temperature sensor 168 for sensing a temperature of tissue between the jaw members 167, 169 (FIG. 6). The temperature sensor 168 may be, for example, a thermocouple, a resistive temperature device, an infrared sensor, a bimetallic device, etc.

In use, a clinician may place the end effector 132 and close the jaws 144 around a tissue bite to be acted upon, for example, by pivoting the jaw closure trigger 142 along arrow 183 as described. Once the tissue bite is secure between the jaws 144, the clinician may initiate the provision of RF or other electro-surgical energy by the generator 102 and through the electrodes 177, 179. The provision of RF energy may be accomplished in any suitable way. For example, the clinician may activate the foot switch 120 (FIG. 8) of the generator 102 to initiate the provision of RF energy. Also, for example, the hand piece 130 may comprise one or more switches 181 that may be actuated by the clinician to cause the generator 102 to begin providing RF energy. Additionally, in some embodiments, RF energy may be provided based on the position of the jaw closure trigger 142. For example, when the trigger 142 is fully depressed (indicating that the jaws 144 are closed), RF energy may be provided. Also, according to various embodiments, the blade 175 may be advanced during closure of the jaws 144 or may be separately advanced by the clinician after closure of the jaws 144 (e.g., after a RF energy has been applied to the tissue).

FIG. 8 is a diagram of the surgical system 100 of FIG. 1. In various embodiments, the generator 102 may comprise several separate functional elements, such as modules and/or blocks. Different functional elements or modules may be configured for driving the different kinds of surgical devices 104, 106. For example an ultrasonic generator module 108 may drive an ultrasonic device, such as the ultrasonic device 104. An electrosurgery/RF generator module 110 may drive the electrosurgical device 106. For example, the respective modules 108, 110 may generate respective drive signals for driving the surgical devices 104, 106. In various embodiments, the ultrasonic generator module 108 and/or the electrosurgery/RF generator module 110 each may be formed integrally with the generator 102. Alternatively, one or more of the modules 108, 110 may be provided as a separate circuit module electrically coupled to the generator 102. (The modules 108 and 110 are shown in phantom to illustrate this option.) Also, in some embodiments, the electrosurgery/RF generator module 110 may be formed integrally with the ultrasonic generator module 108, or vice versa.

In accordance with the described embodiments, the ultrasonic generator module 108 may produce a drive signal or signals of particular voltages, currents, and frequencies, e.g. 55,500 cycles per second (Hz). The drive signal or signals may be provided to the ultrasonic device 104, and specifically to the transducer 114, which may operate, for example, as described above. In some embodiments, the generator 102 may be configured to produce a drive signal of a particular voltage, current, and/or frequency output signal that can be stepped with high resolution, accuracy, and repeatability. Optionally, the tissue impedance module 402 may be included separately or formed integrally with the ultrasonic generator module 108 to measure tissue impedance when utilizing an ultrasonic device 104, for example, as described herein above.

In accordance with the described embodiments, the electrosurgery/RF generator module 110 may generate a drive signal or signals with output power sufficient to perform bipolar electrosurgery using radio frequency (RF) energy. In bipolar electrosurgery applications, the drive signal may be provided, for example, to the electrodes 177, 179 of the electrosurgical device 106, for example, as described above. Accordingly, the generator 102 may be configured for therapeutic purposes by applying electrical energy to the tissue sufficient for treating the tissue (e.g., coagulation, cauterization, tissue welding, etc.).

The generator 102 may comprise an input device 145 located, for example, on a front panel of the generator 102 console. The input device 145 may comprise any suitable device that generates signals suitable for programming the operation of the generator 102. In operation, the user can program or otherwise control operation of the generator 102 using the input device 145. The input device 145 may comprise any suitable device that generates signals that can be used by the generator (e.g., by one or more processors contained in the generator) to control the operation of the generator 102 (e.g., operation of the ultrasonic generator module 108 and/or electrosurgery/RF generator module 110). In various embodiments, the input device 145 includes one or more of buttons, switches, thumbwheels, keyboard, keypad, touch screen monitor, pointing device, remote connection to a general purpose or dedicated computer. In other embodiments, the input device 145 may comprise a suitable user interface, such as one or more user interface screens displayed on a touch screen monitor, for example. Accordingly, by way of the input device 145, the user can set or program various operating parameters of the generator, such as, for example, current (I), voltage (V), frequency (f), and/or period (T) of a drive signal or signals generated by the ultrasonic generator module 108 and/or electrosurgery/RF generator module 110.

The generator 102 may also comprise an output device 147 (FIG. 1) located, for example, on a front panel of the generator 102 console. The output device 147 includes one or more devices for providing a sensory feedback to a user. Such devices may comprise, for example, visual feedback devices (e.g., an LCD display screen, LED indicators), audio feedback devices (e.g., a speaker, a buzzer) or tactile feedback devices (e.g., haptic actuators). Although certain modules and/or blocks of the generator 102 may be described by way of example, it can be appreciated that a greater or lesser number of modules and/or blocks may be used and still fall within the scope of the embodiments. Further, although various embodiments may be described in terms of modules and/or blocks to facilitate description, such modules and/or blocks may be implemented by one or more hardware components, e.g., processors, Digital Signal Processors (DSPs), Programmable Logic Devices (PLDs), Application Specific Integrated Circuits (ASICs), circuits, registers and/or software components, e.g., programs, subroutines, logic and/or combinations of hardware and software components.

In some embodiments, the ultrasonic generator drive module 108 and electrosurgery/RF drive module 110 may comprise one or more embedded applications implemented as firmware, software, hardware, or any combination thereof. The modules 108, 110 may comprise various executable modules such as software, programs, data, drivers, application program interfaces (APIs), and so forth. The firmware may be stored in nonvolatile memory (NVM), such as in bit-masked read-only memory (ROM) or flash memory. In various implementations, storing the firmware in ROM may preserve flash memory. The NVM may comprise other types of memory including, for example, programmable ROM (PROM), erasable programmable ROM (EPROM), electrically erasable programmable ROM (EEPROM), or battery backed random-access memory (RAM) such as dynamic RAM (DRAM), Double-Data-Rate DRAM (DDRAM), and/or synchronous DRAM (SDRAM).

In some embodiments, the modules 108, 110 comprise a hardware component implemented as a processor for executing program instructions for monitoring various measurable characteristics of the devices 104, 106 and generating a corresponding output drive signal or signals for operating the devices 104, 106. In embodiments in which the generator 102 is used in conjunction with the ultrasonic device 104, the drive signal may drive the ultrasonic transducer 114 in cutting and/or coagulation operating modes. Electrical characteristics of the device 104 and/or tissue may be measured and used to control operational aspects of the generator 102 and/or provided as feedback to the user. In embodiments in which the generator 102 is used in conjunction with the electrosurgical device 106, the drive signal may supply electrical energy (e.g., RF energy) to the end effector 132 in cutting, coagulation and/or desiccation modes. Electrical characteristics of the device 106 and/or tissue may be measured and used to control operational aspects of the generator 102 and/or provided as feedback to the user. In various embodiments, as previously discussed, the hardware components may be implemented as DSP, PLD, ASIC, circuits, and/or registers. In some embodiments, the processor may be configured to store and execute computer software program instructions to generate the step function output signals for driving various components of the devices 104, 106, such as the ultrasonic transducer 114 and the end effectors 126, 132.

Figure 9:
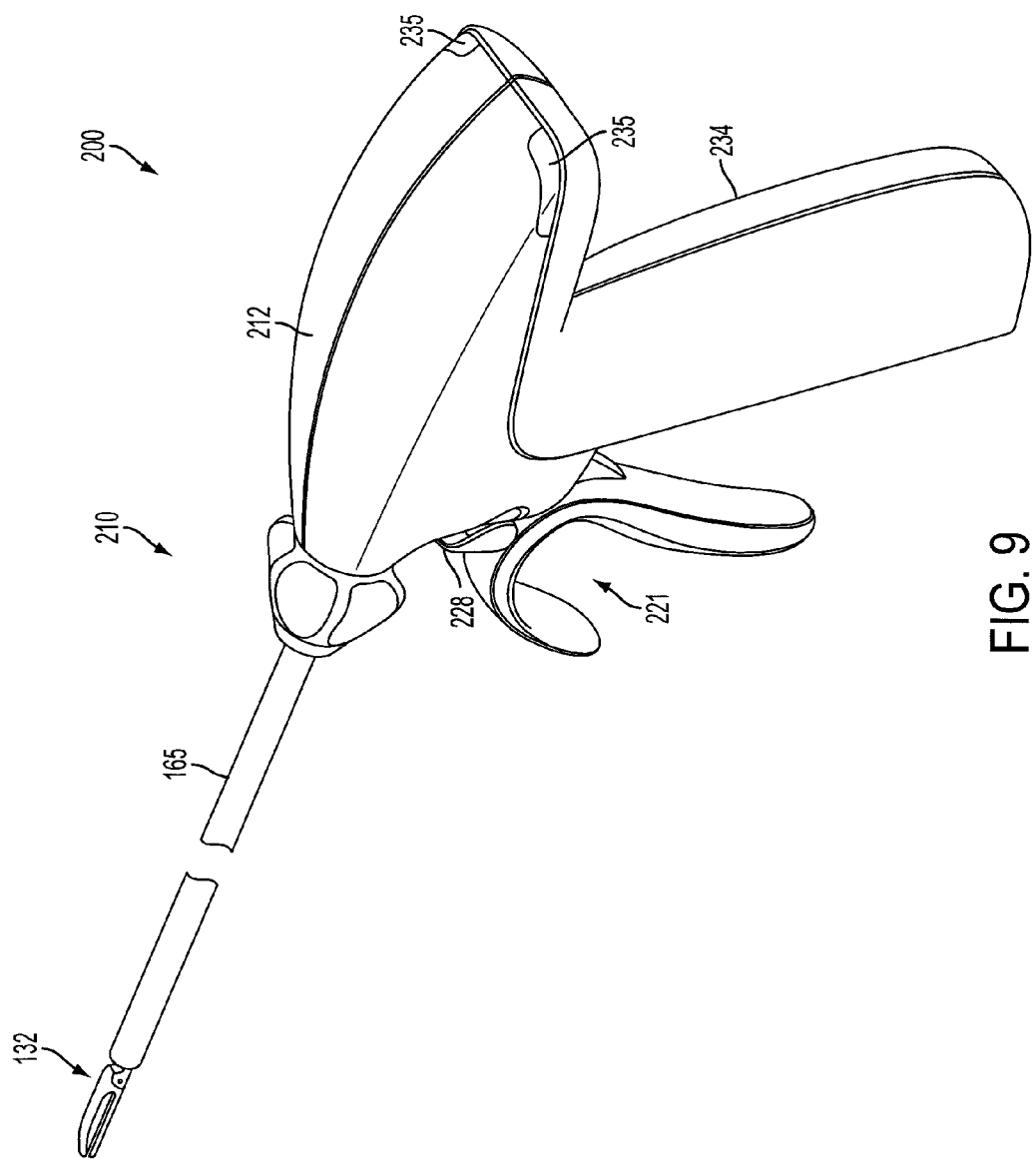
FIG. 9 shows a perspective view of one example embodiment of a surgical system comprising a cordless electrical energy surgical instrument with an integral generator.

As described herein above, the surgical devices 104, 106 described herein may be incorporated into unitary surgical systems comprising both a surgical device, such as 104 and 106, and an integral generator. FIGS. 9-12 show various embodiments of a surgical system 200 comprising an example unitary electrosurgical system 200. FIG. 9 shows a perspective view of one example embodiment of a surgical system 200 comprising a cordless electrical energy surgical instrument 210 with an integral generator (not shown in FIG. 9). The electrosurgical system 200 is similar to the surgical system 100 (e.g., utilized with the electrosurgical device 106). The electrosurgical system 200 can be configured to supply energy, such as electrical energy, ultrasonic energy, heat energy, or any combination thereof, to the tissue of a patient either independently or simultaneously as described in connection with FIGS. 1-8, for example. The electrosurgical instrument 210 may utilize the end effector 132 and elongated shaft 165 described herein with respect to FIGS. 4-7 in conjunction with a cordless proximal handle 212. In one example embodiment, the handle 212 includes the integral generator circuit 220 (see FIG. 10). The generator circuit 220, sometimes referred to herein as a generator 220, performs a function substantially similar to that of generator 102. In one example embodiment, the generator circuit 220 is coupled to a controller or control circuit (e.g., 281 in FIG. 11). In the illustrated embodiment, the control circuit is integrated into the generator circuit 220. In other embodiments, the control circuit may be separate from the generator circuit 220.

In one example embodiment, various electrodes in the end effector 126 (e.g., 177, 179) may be coupled to the generator circuit 220. The control circuit 281 may be used to activate the generator 220, which may serve as an electrical source. In various embodiments, the generator 220 may comprise an RF source, an ultrasonic source, a direct current source, a microwave source, and/or any other suitable type of thermogenic energy source, for example. For example, a direct current source may be utilized to power a heating element that could treat tissue. In one example embodiment, a button 228 may be provided to activate the generator circuit 220 to provide energy to the end effector 126.

Figure 10:
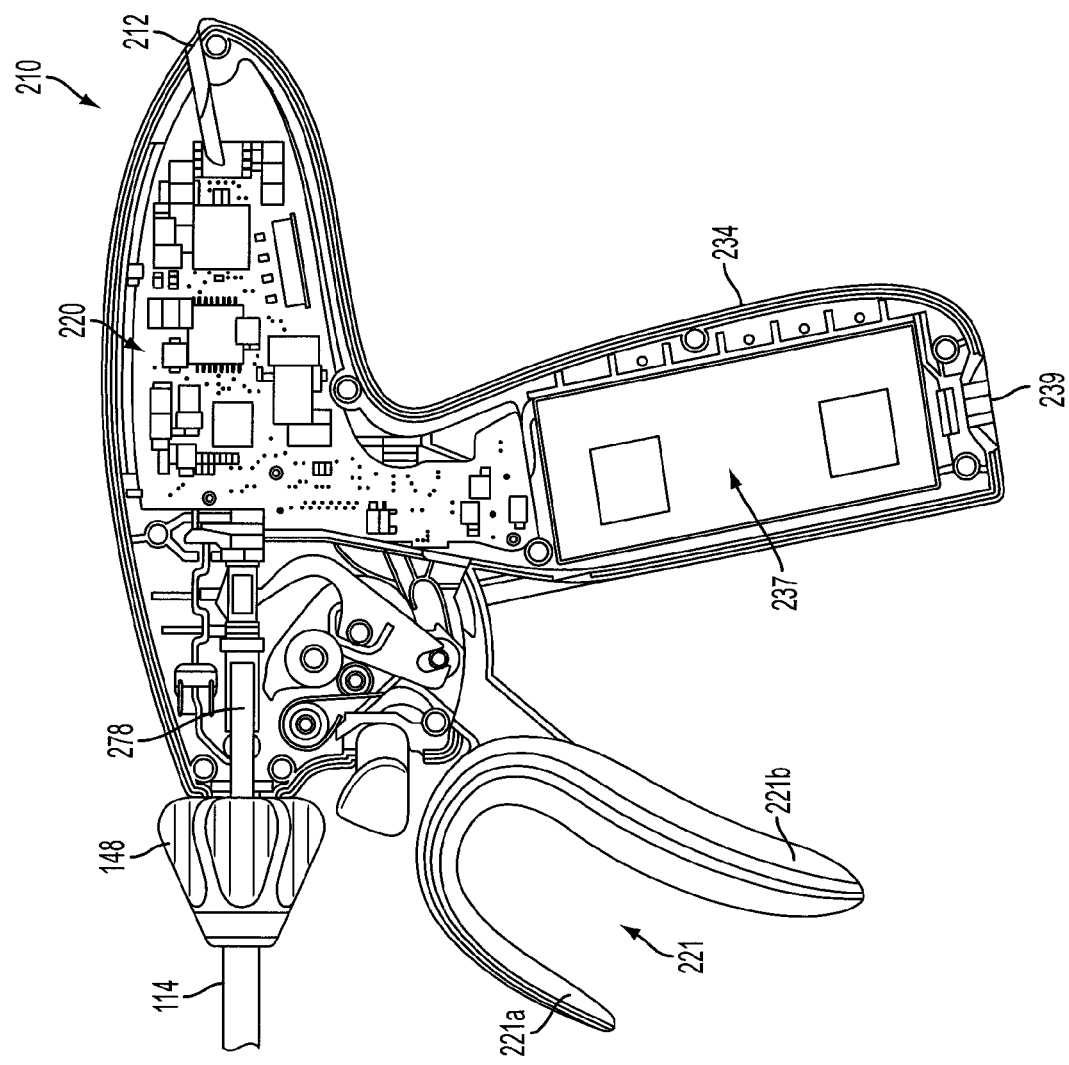
FIG. 10 shows a side view of a handle of one embodiment of the surgical instrument of FIG. 7 with half of the handle body removed to illustrate various components therein.

FIG. 10 shows a side view of one example embodiment of the handle 212 of the cordless surgical instrument 210 with half of a first handle body removed to illustrate various components within the second handle body 234. The handle 212 may comprise a lever arm 221 (e.g., a trigger) which may be pulled along a path (similar to 183) around a pivot point. The lever arm 221 may be coupled to an axially moveable member 278 disposed within the shaft 165 by a shuttle operably engaged to an extension of lever arm 221. In one example embodiment, the lever arm 221 defines a shepherd's hook shape comprising a distal trigger hook 221a and a proximal trigger portion 221b. As illustrated, the distal trigger hook 221a may have a first length while the proximal trigger portion 221b may have a second length with the second length greater than the first length.

In one example embodiment, the cordless electrosurgical instrument comprises a battery 237. The battery 237 provides electrical energy to the generator circuit 220. The battery 237 may be any battery suitable for driving the generator circuit 220 at the desired energy levels. In one example embodiment, the battery 237 is a 1030 mAhr, triple-cell Lithium Ion Polymer battery. The battery may be fully charged prior to use in a surgical procedure, and may hold a voltage of about 12.6V. The battery 237 may have two fuses fitted to the cordless electrosurgical instrument 210, arranged in line with each battery terminal. In one example embodiment, a charging port 239 is provided to connect the battery 237 to a DC current source (not shown).

Figure 11:
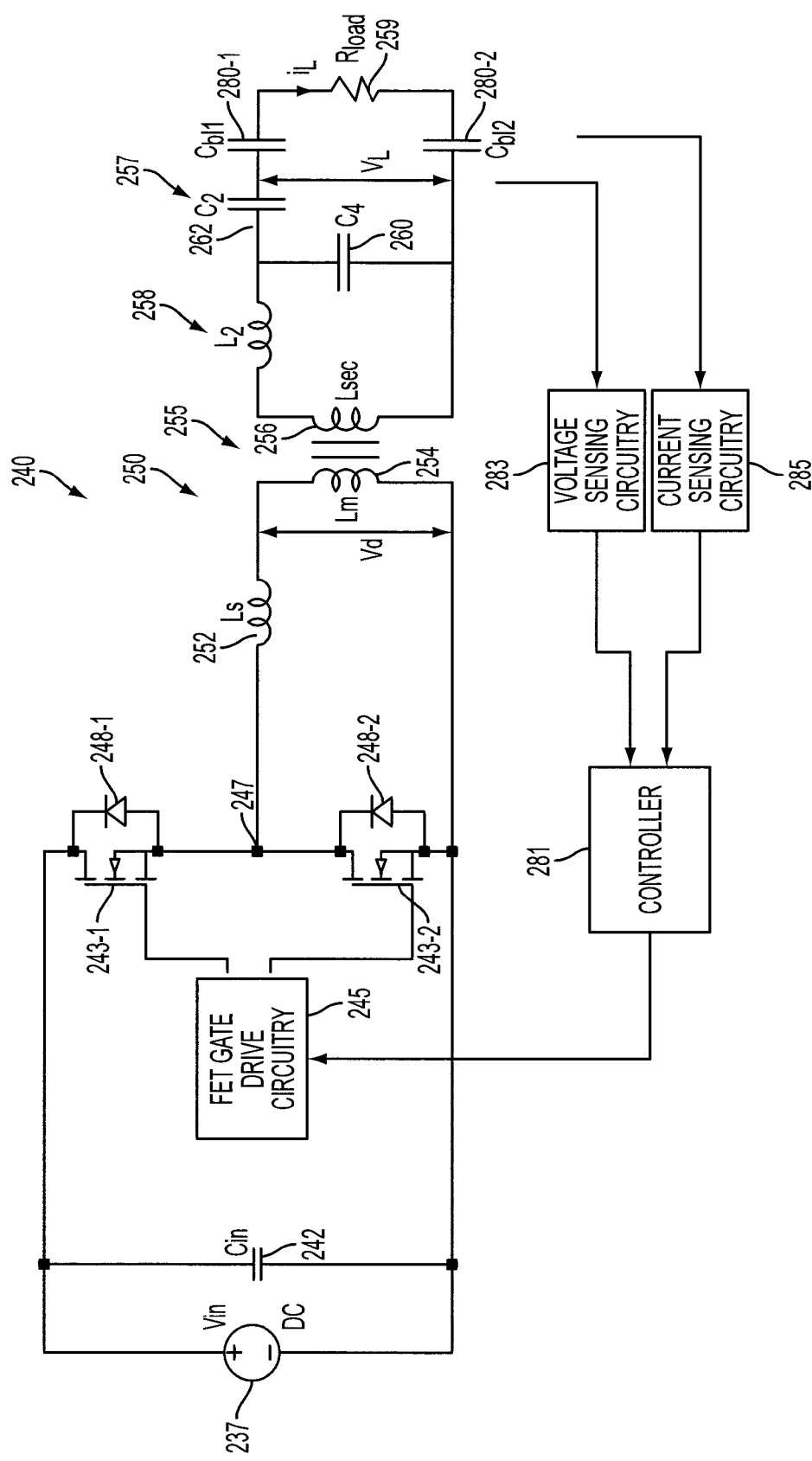
FIG. 11 shows one embodiment of an RF drive and control circuit.

The generator circuit 220 may be configured in any suitable manner. In some embodiments, the generator circuit comprises an RF drive and control circuit 240 and a controller circuit 282. FIG. 11 shows one embodiment of an RF drive and control circuit 240. FIG. 11 is a part schematic part block diagram showing the RF drive and control circuitry 240 used in this embodiment to generate and control the RF electrical energy supplied to the end effector 126. In this embodiment, the drive circuitry 240 is a resonant mode RF amplifier comprising a parallel resonant network on the RF amplifier output and the control circuitry operates to control the operating frequency of the electrosurgical drive signal so that it is maintained at the resonant frequency of the drive circuit, which in turn controls the amount of power supplied to the end effector 126. The way that this is achieved will become apparent from the following description.

As shown in FIG. 11, the RF drive and control circuit 240 comprises the above described battery 237 are arranged to supply, in this example, about 0V and about 12V rails. An input capacitor ($C_{in}$) 242 is connected between the 0V and the 12V for providing a low source impedance. A pair of FET switches 243-1 and 243-2 (both of which are N-channel in this embodiment to reduce power losses) is connected in series between the 0V rail and the 12V rail. FET gate drive circuitry 245 is provided that generates two drive signals - one for driving each of the two FET's 243. The FET gate drive circuitry 245 generates drive signals that causes the upper FET (243-1) to be on when the lower FET (243-2) is off and vice versa. This causes the node 247 to be alternately connected to the 12V rail (when the FET 243-1 is switched on) and the 0V rail (when the FET 243-2 is switched on). FIG. 8B also shows the internal parasitic diodes 248-1 and 248-2 of the corresponding FET's 243, which conduct during any periods that the FET's 243 are open.

As shown in FIG. 11, the node 247 is connected to an inductor-inductor resonant circuit 250 formed by inductor $L_s$252 and inductor $L_m$254. The FET gate driving circuitry 245 is arranged to generate drive signals at a drive frequency ($f_d$) that opens and crosses the FET switches 243 at the resonant frequency of the parallel resonant circuit 250. As a result of the resonant characteristic of the resonant circuit 250, the square wave voltage at node 247 will cause a substantially sinusoidal current at the drive frequency ($f_d$) to flow within the resonant circuit 250. As illustrated in FIG. 11, the inductor $L_m$254 is the primary of a transformer 255, the secondary of which is formed by inductor $L_{sec}$256. The inductor $L_{sec}$256 of the transformer 255 secondary is connected to an inductor-capacitor-capacitor parallel resonant circuit 257 formed by inductor $L_2$258, capacitor $C_4$260, and capacitor $C_2$262. The transformer 255 up-converts the drive voltage ($V_d$) across the inductor $L_m$254 to the voltage that is applied to the output parallel resonant circuit 257. The load voltage ($V_L$) is output by the parallel resonant circuit 257 and is applied to the load (represented by the load resistance $R_{load}$259 in FIG. 8B) corresponding to the impedance of the forceps' jaws and any tissue or vessel gripped by the end effector 126. As shown in FIG. 8B, a pair of DC blocking capacitors $C_{b11}$280-1 and $C_{b12}$280-2 is provided to prevent any DC signal being applied to the load 259.

In one embodiment, the transformer 255 may be implemented with a Core Diameter (mm), Wire Diameter (mm), and Gap between secondary windings in accordance with the following specifications:

Core Diameter, D (mm)
D=19.9×10−3
Wire diameter, W (mm) for 22 AWG wire
W=7.366×10−4
Gap between secondary windings, in gap=0.125
G=gap/25.4

In this embodiment, the amount of electrical power supplied to the end effector 126 is controlled by varying the frequency of the switching signals used to switch the FET's 243. This works because the resonant circuit 250 acts as a frequency dependent (loss less) attenuator. The closer the drive signal is to the resonant frequency of the resonant circuit 250, the less the drive signal is attenuated. Similarly, as the frequency of the drive signal is moved away from the resonant frequency of the circuit 250, the more the drive signal is attenuated and so the power supplied to the load reduces. In this embodiment, the frequency of the switching signals generated by the FET gate drive circuitry 245 is controlled by a controller 281 based on a desired power to be delivered to the load 259 and measurements of the load voltage ($V_L$) and of the load current ($I_L$) obtained by conventional voltage sensing circuitry 283 and current sensing circuitry 285. The way that the controller 281 operates will be described in more detail below.

In one embodiment, the voltage sensing circuitry 283 and the current sensing circuitry 285 may be implemented with high bandwidth, high speed rail-to-rail amplifiers (e.g., LMH6643 by National Semiconductor). Such amplifiers, however, consume a relatively high current when they are operational. Accordingly, a power save circuit may be provided to reduce the supply voltage of the amplifiers when they are not being used in the voltage sensing circuitry 283 and the current sensing circuitry 285. In one-embodiment, a step-down regulator (e.g., LT1502 by Linear Technologies) may be employed by the power save circuit to reduce the supply voltage of the rail-to-rail amplifiers and thus extend the life of the battery 237.

Figure 12:
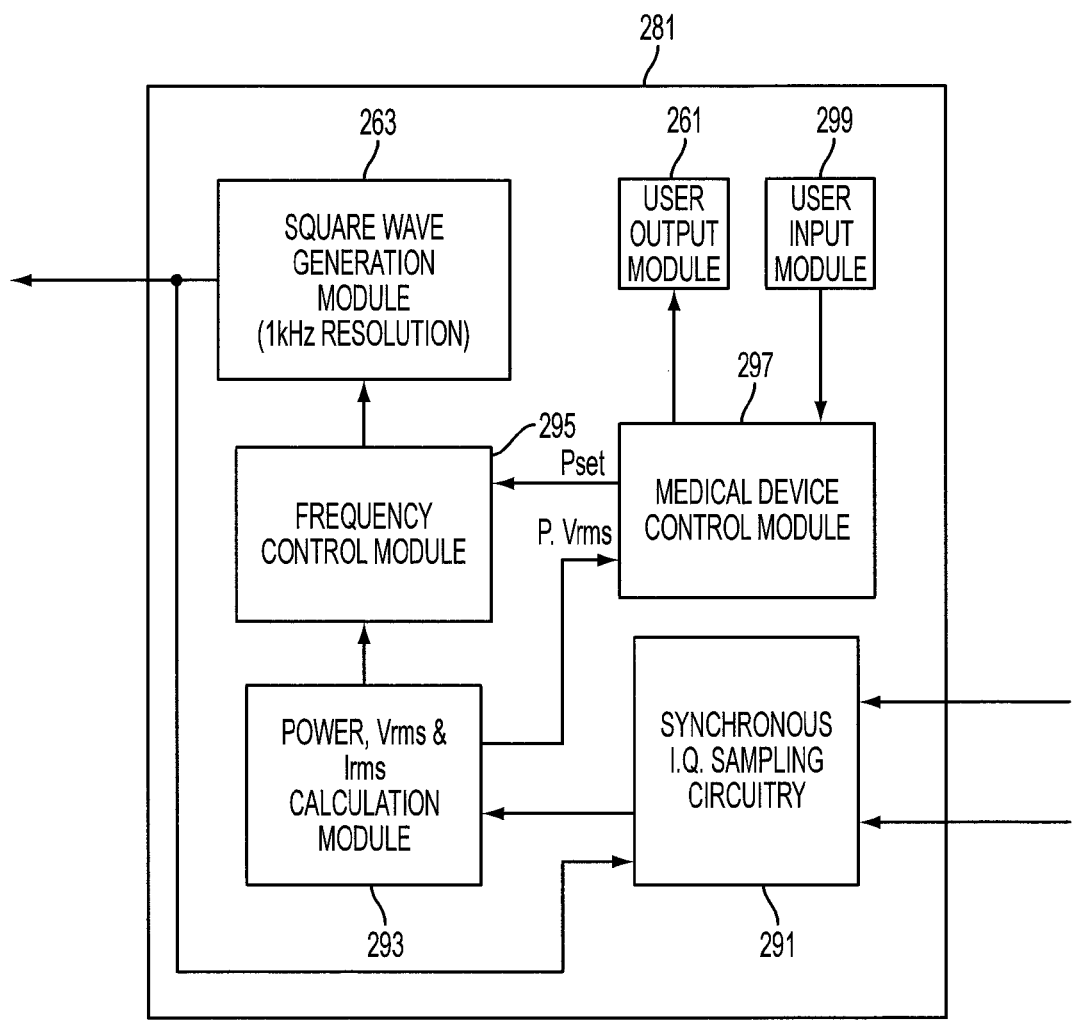
FIG. 12 shows one embodiment of the main components of a control circuit.

FIG. 12 shows the main components of the controller 281, according to one embodiment. In the embodiment illustrated in FIG. 12, the controller 281 is a microprocessor based controller and so most of the components illustrated in FIG. 8c are software based components. Nevertheless, a hardware based controller 281 may be used instead. As shown, the controller 281 includes synchronous I,Q sampling circuitry 291 that receives the sensed voltage and current signals from the sensing circuitry 283 and 285 and obtains corresponding samples which are passed to a power, $V_{rms}$ and $I_{rms}$ calculation module 293. The calculation module 293 uses the received samples to calculate the RMS voltage and RMS current applied to the load 259 (FIG. 8B; end effector 126 and tissue/vessel gripped thereby) and from them the power that is presently being supplied to the load 259. The determined values are then passed to a frequency control module 295 and a medical device control module 297. The medical device control module 297 uses the values to determine the present impedance of the load 259 and based on this determined impedance and a pre-defined algorithm, determines what set point power($P_{set}$) should be applied to the frequency control module 295. The medical device control module 297 is in turn controlled by signals received from a user input module 299 that receives inputs from the user (for example pressing buttons 228 or activating the control levers 221 on the handle 212) and also controls output devices (lights, a display, speaker or the like) on the handle 212 via a user output module 261.

The frequency control module 295 uses the values obtained from the calculation module 293 and the power set point ($P_{set}$) obtained from the medical device control module 297 and predefined system limits (to be explained below), to determine whether or not to increase or decrease the applied frequency. The result of this decision is then passed to a square wave generation module 263 which, in this embodiment, increments or decrements the frequency of a square wave signal that it generates by 1 kHz, depending on the received decision. As those skilled in the art will appreciate, in an alternative embodiment, the frequency control module 295 may determine not only whether to increase or decrease the frequency, but also the amount of frequency change required. In this case, the square wave generation module 263 would generate the corresponding square wave signal with the desired frequency shift. In this embodiment, the square wave signal generated by the square wave generation module 263 is output to the FET gate drive circuitry 245, which amplifies the signal and then applies it to the FET 243-1. The FET gate drive circuitry 245 also inverts the signal applied to the FET 243-1 and applies the inverted signal to the FET 243-2.

According to various embodiments, the generator 102, 220 may provide power to a tissue bite according to one or more power curves. A power curve may define a relationship between power delivered to the tissue and the impedance of the tissue. For example as the impedance of the tissue changes (e.g., increases) during coagulation, the power provided by the generator 102, 220 may also change (e.g., decrease) according to the applied power curve.

Different power curves may be particularly suited, or ill-suited, to different types and/or sizes of tissue bites. Aggressive power curves (e.g., power curves calling for high power levels) may be suited for large tissue bites. When applied to smaller tissue bites, such as small vessels, more aggressive power curves may lead to exterior searing. Exterior searing may reduce the coagulation/weld quality at the exterior and can also prevent complete coagulation of interior portions of the tissue. Similarly, less aggressive power curves may fail to achieve hemostasis when applied to larger tissue bites (e.g., larger bundles).

Figure 13:
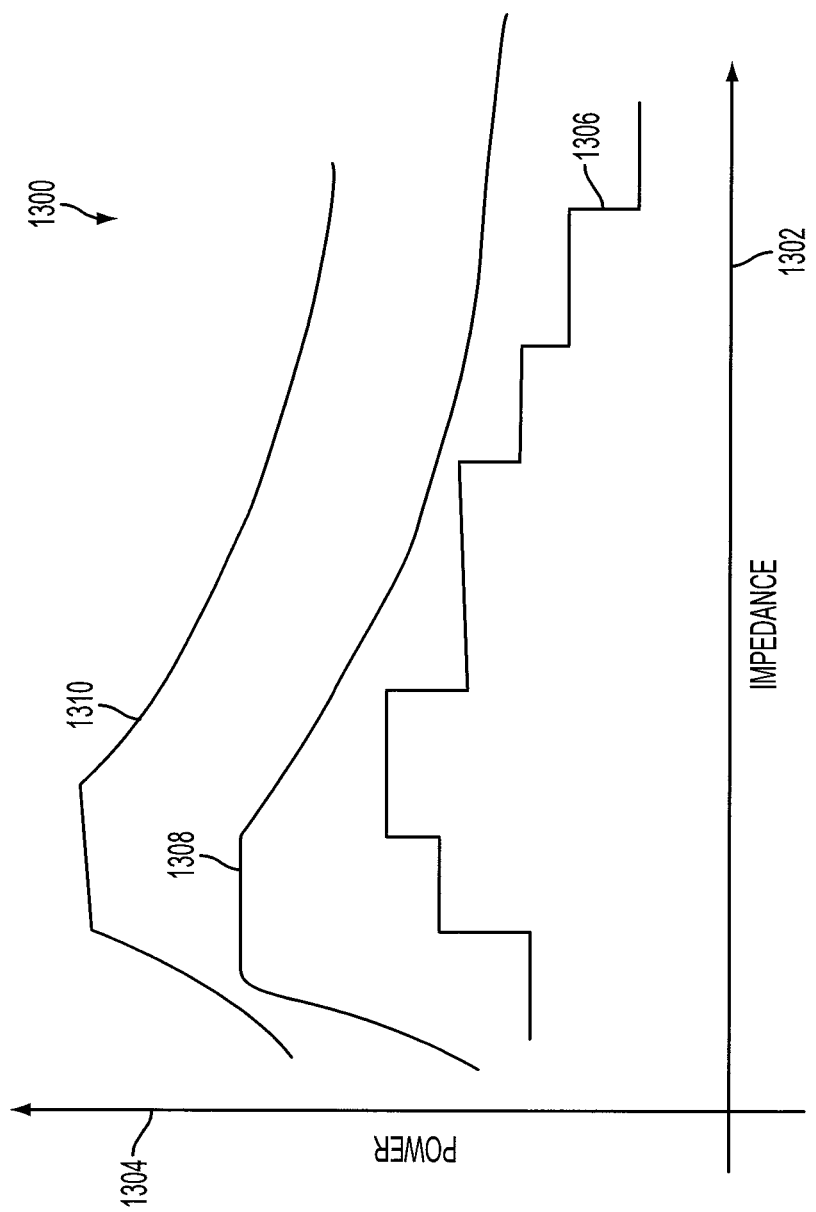
FIG. 13 illustrates one embodiment of a chart showing example power curves.

FIG. 13 illustrates one embodiment of a chart 1300 showing example power curves 1306, 1308, 1310. The chart 1300 comprises an impedance axis 1302 illustrating increasing potential tissue impedances from left to right. A power axis 1304 illustrates increasing power from down to up. Each of the power curves 1306, 1308, 1310 may define a set of power levels, on the power axis 1304, corresponding to a plurality of potential sensed tissue impedances, in the impedance axis 1302. In general, power curves may take different shapes, and this is illustrated in FIG. 13. Power curve 1306 is shown with a step-wise shape, while power curves 1308, 1310 are shown with curved shapes. It will be appreciated that power curves utilized by various embodiments may take any usable continuous or non-continuous shape. The rate of power delivery or aggressiveness of a power curve may be indicated by its position on the chart 1300. For example, power curves that deliver higher power for a given tissue impedance may be considered more aggressive. Accordingly, between two power curves, the curve positioned highest on the power axis 1304 may be the more aggressive. It will be appreciated that some power curves may overlap.

The aggressiveness of two power curves may be compared according to any suitable method. For example, a first power curve may be considered more aggressive than a second power curve over a given range of potential tissue impedances if the first power curve has a higher delivered power over the range. Delivered power over the range of potential tissue impedances may be measured in any suitable manner. For example, the delivered power over the range may be represented by an area under the power curve over the range or, when a power curve is expressed discretely, a sum of the power values for the power curve over the set of potential tissue impedances.

According to various embodiments, the power curve shifting algorithms described herein may be used with any kind of surgical device (e.g., ultrasonic device 104, electrosurgical device 106). In embodiments utilizing a ultrasonic device 104, tissue impedance readings may be taken utilizing electrodes 157, 159 and/or utilizing the clamp arm assembly 451 described herein with respect to FIGS. 3A and 3B. With an electrosurgical device, such as 106, tissue impedance readings may be taken utilizing first and second electrodes 177, 179.

In some embodiments, an electrosurgical device 104 may comprise a positive temperature coefficient (PTC) material positioned between one or both of the electrodes 177, 179 and the tissue bite. The PTC material may have an impedance profile that remains relatively low and relatively constant until it reaches a threshold or trigger temperature, at which point the impedance of the PTC material may increase. In use, the PTC material may be placed in contact with the tissue while power is applied. The trigger temperature of the PTC material may be selected such that it corresponds to a tissue temperature indicating the completion of welding or coagulation. Accordingly, as a welding or coagulation process is completed, the impedance of the PTC material may increase, bringing about a corresponding decrease in power actually provided to the tissue.

It will be appreciated that during the coagulation or welding process, tissue impedance may generally increase. In some embodiments, tissue impedance may display a sudden impedance increase indicating successful coagulation. The increase may be due to physiological changes in the tissue, a PTC material reaching its trigger threshold, etc., and may occur at any point in the coagulation process. The amount of energy that may be required to bring about the sudden impedance increase may be related to the thermal mass of the tissue being acted upon. The thermal mass of any given tissue bite, in turn, may be related to the type and amount of tissue in the bite.

Various embodiments may utilize this sudden increase in tissue impedance to select an appropriate power curve for a given tissue bite. For example, the generator 102 may select and apply successively more aggressive power curves until the tissue impedance reaches an impedance threshold indicating that the sudden increase has occurred. For example, reaching the impedance threshold may indicate that coagulation is progressing appropriately with the currently applied power curve. The impedance threshold may be a tissue impedance value, a rate of change of tissue impedance, and/or a combination of impedance and rate of change. For example, the impedance threshold may be met when a certain impedance value and/or rate of change are observed. According to various embodiments, different power curves may have different impedance thresholds, as described herein.

Figure 14:
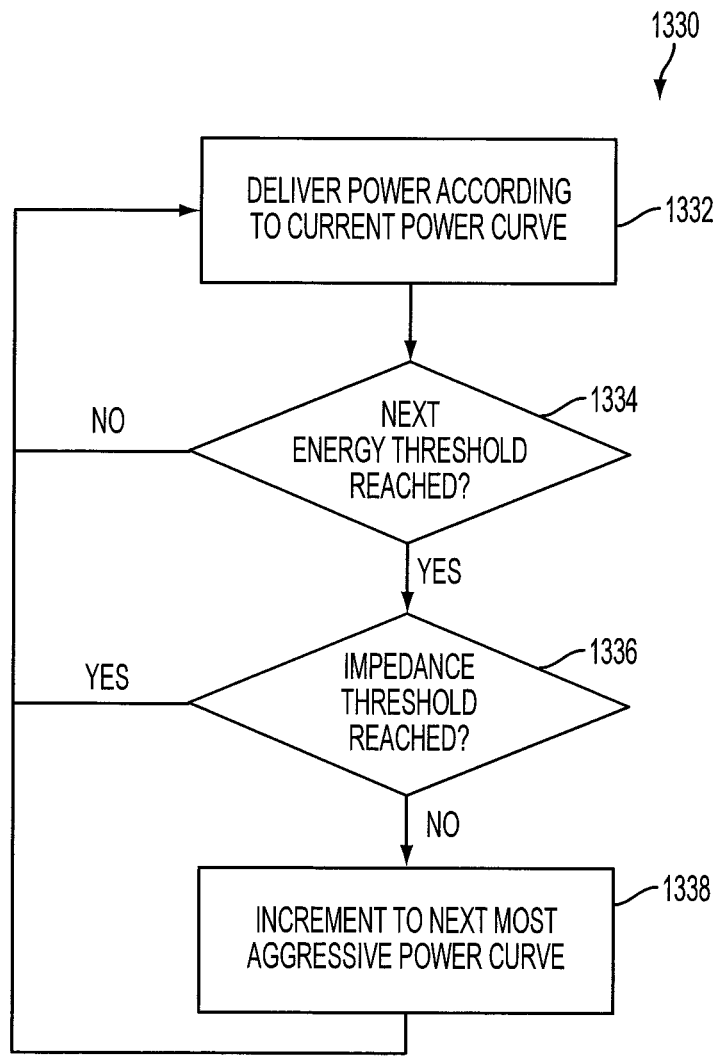
FIG. 14 illustrates one embodiment of a process flow for applying one or more power curves to a tissue bite.

FIG. 14 illustrates one embodiment of a process flow 1330 for applying one or more power curves to a tissue bite. Any suitable number of power curves may be used. The power curves may be successively applied in order of aggressiveness until one of the power curves drives the tissue to the impedance threshold. At 1332, the generator 102, 220 may apply a first power curve. According to various embodiments, the first power curve may be selected to deliver power at a relatively low rate. For example, the first power curve may be selected to avoid tissue searing with the smallest and most vulnerable expected tissue bites.

The first power curve may be applied to the tissue in any suitable manner. For example, the generator 102, 220 may generate a drive signal implementing the first power curve. The power curve may be implemented by modulating the power of the drive signal. The power of the drive signal may be modulated in any suitable manner. For example, the voltage and/or current of the signal may be modulated. Also, in various embodiments, the drive signal may be pulsed. For example, the generator 102, 220 may modulate the average power by changing the pulse width, duty cycle, etc. of the drive signal. The drive signal may be provided to the first and second electrodes 177, 179 of the electrosurgical device 106. In some embodiments the drive signal implementing the first power curve may be provided to an ultrasonic generator 114 of the ultrasonic device 104 described above.

While applying the first power curve, the generator 102, 220 may monitor the total energy provided to the tissue. The impedance of the tissue may be compared to the impedance threshold at one or more energy thresholds. There may be any suitable number of energy thresholds, which may be selected according to any suitable methodology. For example, the energy thresholds may be selected to correspond to known points where different tissue types achieve the impedance threshold. At 1334, the generator 102, 220 may determine whether the total energy delivered to the tissue has met or exceeded a first energy threshold. If the total energy has not yet reached the first energy threshold, the generator 102, 220 may continue to apply the first power curve at 1332.

If the total energy has reached the first energy threshold, the generator 102, 220 may determine whether the impedance threshold has been reached (1336). As described above, the impedance threshold may be a predetermined rate of impedance change (e.g., increase) a predetermined impedance, or combination of the two. If the impedance threshold is reached, the generator 102, 220 may continue to apply the first power curve at 1332. For example, reaching the impedance threshold in the first power curve may indicate that the aggressiveness of the first power curve is sufficient to bring about suitable coagulation or welding.

In the event that the impedance threshold is not reached at 1336, the generator 102, 220 may increment to the next most aggressive power curve at 1338 and apply the power curve as the current power curve at 1332. When the next energy threshold is reached at 1334, the generator 102, 220 again may determine whether the impedance threshold is reached at 1336. If it is not reached, the generator 102, 220 may again increment to the next most aggressive power curve at 1338 and deliver that power curve at 1332.

The process flow 1330 may continue until terminated. For example, the process flow 1330 may be terminated when the impedance threshold is reached at 1336. Upon reaching the impedance threshold, the generator 102, 220 may apply the then-current power curve until coagulation or welding is complete. Also, for example, the process flow 1330 may terminate upon the exhaustion of all available power curves. Any suitable number of power curves may be used. If the most aggressive power curve fails to drive the tissue to the impedance threshold, the generator 102, 220 may continue to apply the most aggressive power curve until the process is otherwise terminated (e.g., by a clinician or upon reaching a final energy threshold).

According to various embodiments, the process flow 1330 may continue until the occurrence of a termination threshold. The termination threshold may indicate that coagulation and/or welding is complete. For example, the termination threshold may be based on one or more of tissue impedance, tissue temperature, tissue capacitance, tissue inductance, elapsed time, etc. These may be a single termination threshold or, in various embodiments, different power curves may have different termination thresholds. According to various embodiments, different power curves may utilize different impedance thresholds. For example, the process flow 1330 may transition from a first to a second power curve if the first power curve has failed to drive the tissue to a first tissue impedance threshold and may, subsequently, shift from the second to a third power curve if the second power curve has failed to drive the tissue to a second impedance threshold.

Figure 15:
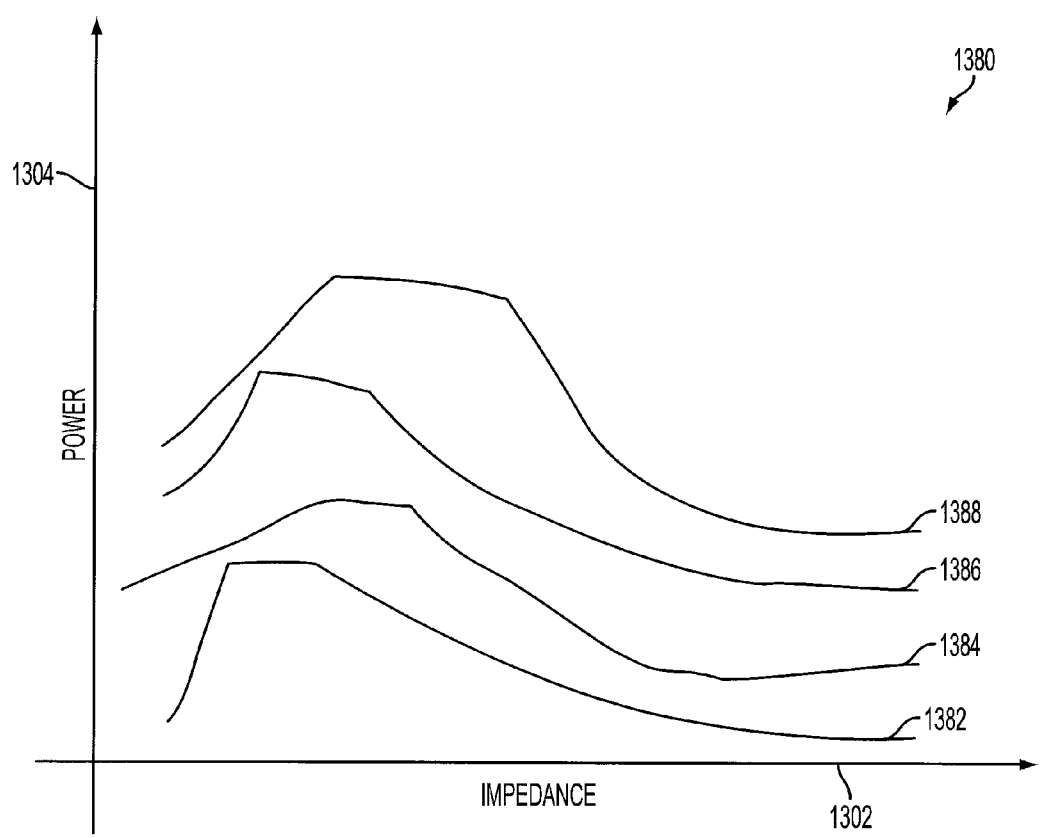
FIG. 15 illustrates one embodiment of a chart showing example power curves that may be used in conjunction with the process flow of FIG. 14.

FIG. 15 illustrates one embodiment of a chart 1380 showing example power curves 1382, 1384, 1386, 1388 that may be used in conjunction with the process flow 1330. Although four power curves 1382, 1384, 1386, 1388 are shown, it will be appreciated that any suitable number of power curves may be utilized. Power curve 1382 may represent the least aggressive power curve and may be applied first. If the impedance threshold is not reached at the first energy threshold, then the generator 102, 220 may provide the second power curve 1384. The other power curves 1386, 1388 may be utilized, as needed, for example in the manner described above.

Figure 16:
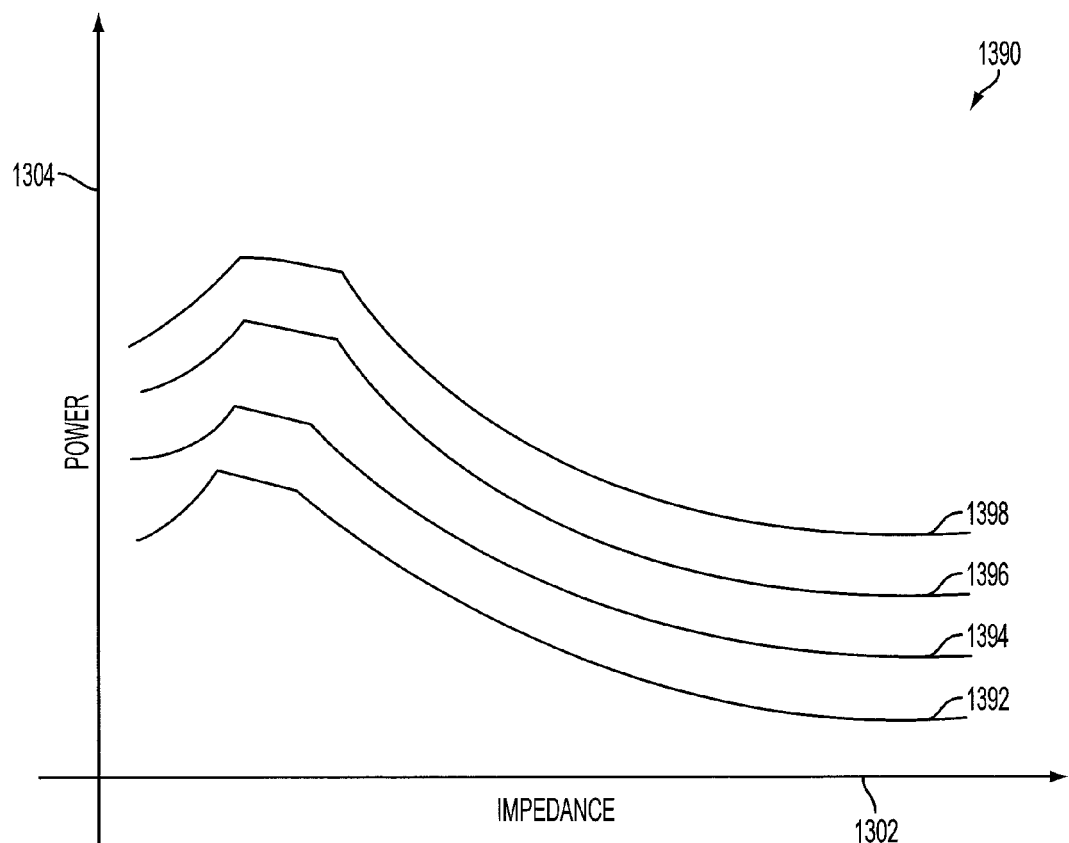
FIG. 16 illustrates one embodiment of a chart showing example common shape power curves that may be used in conjunction with the process flow of FIG. 14.

As illustrated in FIG. 15, the power curves 1382, 1384, 1386, 1388 are of different shapes. It will be appreciated, however, that some or all of a set of power curves implemented by the process flow 1330 may be of the same shape. FIG. 16 illustrates one embodiment of a chart showing example common shape power curves 1392, 1394, 1396, 1398 that may be used in conjunction with the process flow 1330. According to various embodiments, common shape power curves, such as 1392, 1394, 1396, 1398 may be constant multiples of one another. Accordingly, the generator 102, 220 may implement the common shape power curves 1392, 1394, 1396, 1398 by applying different multiples to a single power curve. For example, the curve 1394 may be implemented by multiplying the curve 1392 by a first constant multiplier. The curve 1396 may be generated by multiplying the curve 1392 by a second constant multiplier. Likewise, the curve 1398 may be generated by multiplying the curve 1392 by a third constant multiplier. Accordingly, in various embodiments, the generator 102, 220 may increment to a next most aggressive power curve at 1338 by changing the constant multiplier.

Figure 17B:
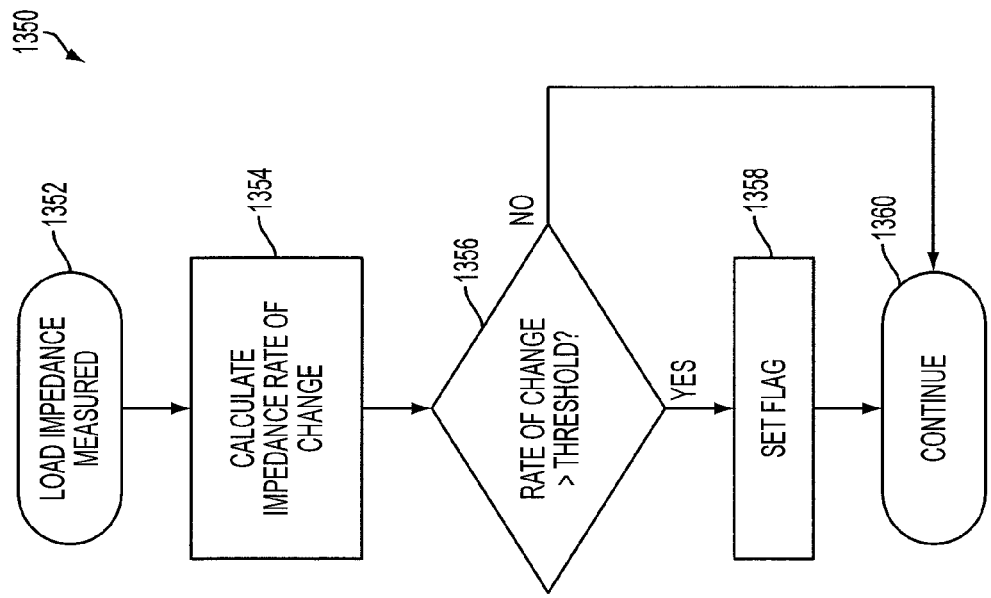
FIGS. 17A-17C illustrate process flows describing routines that may be executed by a digital device of the generator to generally implement the process flow of FIG. 14 described above.
Figure 17A:
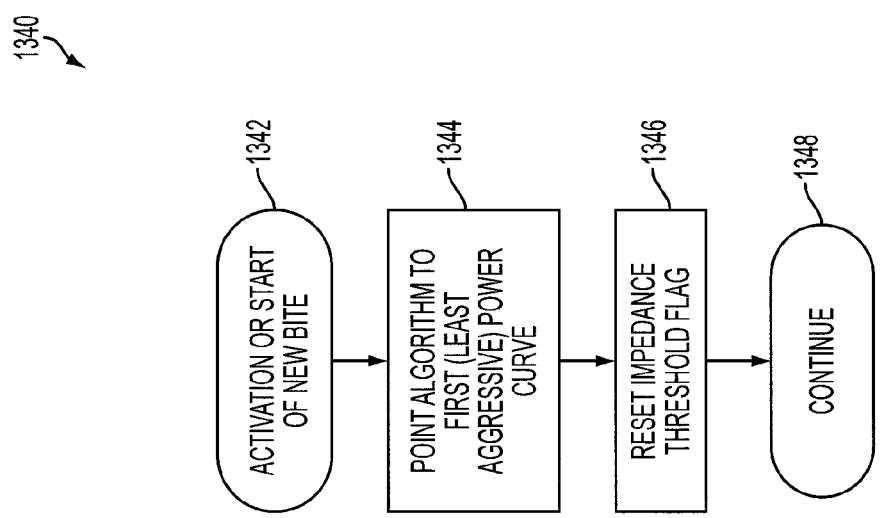
Figure 17C:
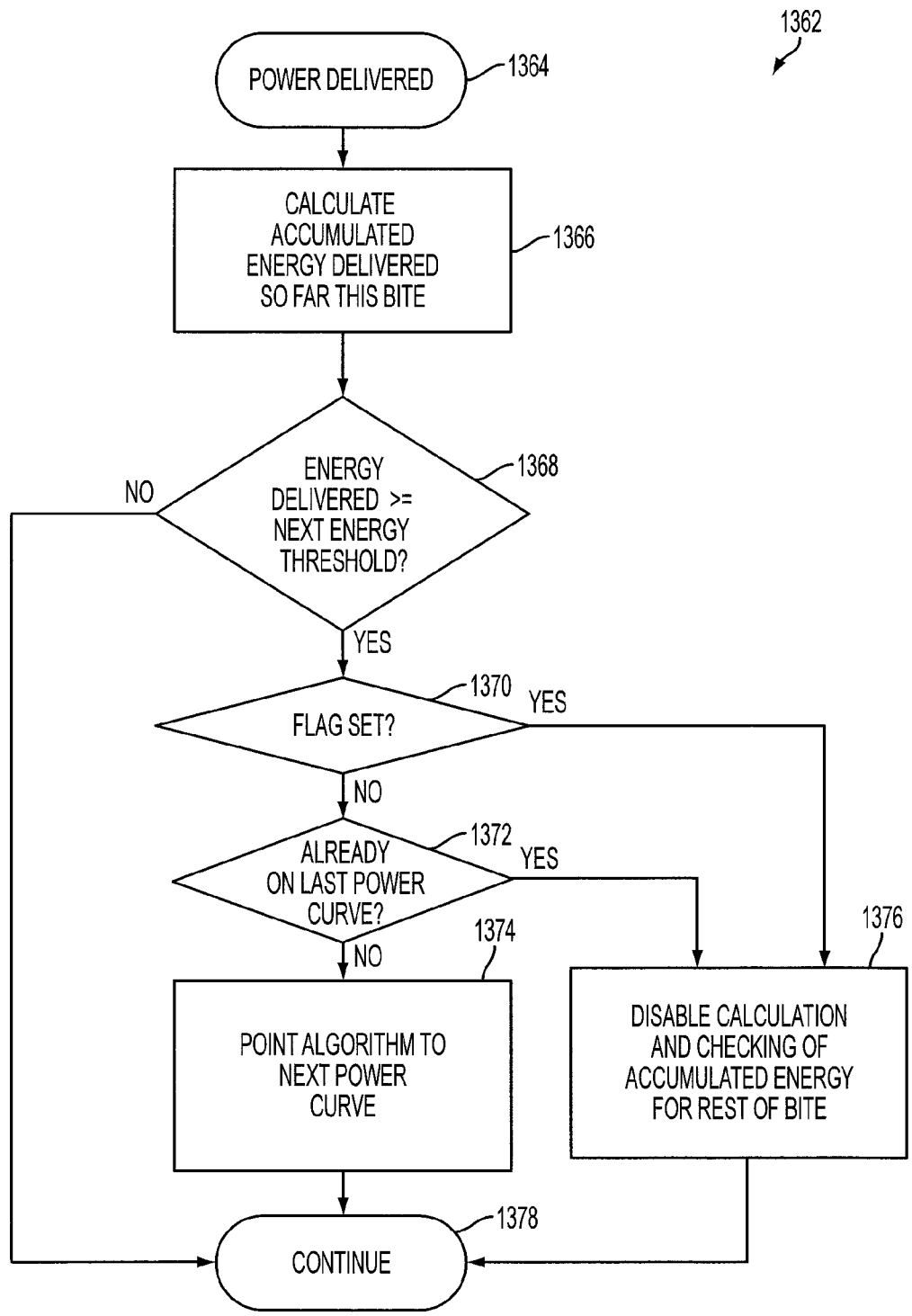

According to various embodiments, the process flow 1330 may be implemented by a digital device (e.g., a processor, digital signal processor, field programmable gate array (FPGA), etc.) of the generator 102, 220. FIGS. 17A-17C illustrate process flows describing routines that may be executed by a digital device of the generator 102, 220 to generally implement the process flow 1330 described above. FIG. 17A illustrates one embodiment of a routine 1340 for preparing the generator 102, 220 to act upon a new tissue bite. The activation or start of the new tissue bite may be initiated at 1342. At 1344, the digital device may point to a first power curve. The first power curve, as described above, may be the least aggressive power curve to be implemented as a part of the process flow 1330. Pointing to the first power curve may comprise pointing to a deterministic formula indicating the first power curve, pointing to a look-up table representing the first power curve, pointing to a first power curve multiplier, etc.

At 1346, the digital device may reset an impedance threshold flag. As described below, setting the impedance threshold flag may indicate that the impedance threshold has been met. Accordingly, resetting the flag may indicate that the impedance threshold has not been met, as may be appropriate at the outset of the process flow 1330. At 1348, the digital device may continue to the next routine 1350.

FIG. 17B illustrates one embodiment of a routine 1350 that may be performed by the digital device to monitor tissue impedance. At 1352, load or tissue impedance may be measured. Tissue impedance may be measured according to any suitable method and utilizing any suitable hardware. For example, according to various embodiments, tissue impedance may be calculated according to Ohm's law utilizing the current and voltage provided to the tissue. At 1354, the digital device may calculate a rate of change of the impedance. The impedance rate of change may likewise be calculated according to any suitable manner. For example, the digital device may maintain prior values of tissue impedance and calculate a rate of change by comparing a current tissue impedance value or values with the prior values. Also, it will be appreciated that the routine 1350 assumes that the impedance threshold is a rate of change. In embodiments where the impedance threshold is not a rate of change, 1354 may be omitted. If the tissue impedance rate of change (or impedance itself) is greater than the threshold (1356), then the impedance threshold flag may be set. The digital device may continue to the next routing at 1360.

FIG. 17C illustrates one embodiment of a routine 1362 that may be performed by the digital device to provide one or more power curves to a tissue bite. At 1364, power may be delivered to the tissue, for example, as described above with respect to 1334 of FIG. 70. The digital device may direct the delivery of the power curve, for example, by applying the power curve to find a corresponding power for each sensed tissue impedance, modulating the corresponding power onto a drive signal provided to the first and second electrodes 177, 179, the transducer 114, etc.

At 1366, the digital device may calculate the total accumulated energy delivered to the tissue. For example, the digital device may monitor the total time of power curve delivery and the power delivered at each time. Total energy may be calculated from these values. At 1368, the digital device may determine whether the total energy is greater than or equal to a next energy threshold, for example, similar to the manner described above with respect to 1334 of FIG. 14. If the next energy threshold is not met, the current power curve may continue to be applied at 1378 and 1364.

If the next energy threshold is met at 1368, then at 1370, the digital device may determine whether the impedance threshold flag is set. The state of the impedance threshold flag may indicate whether the impedance threshold has been met. For example, the impedance threshold flag may have been set by the routine 1350 if the impedance threshold has been met. If the impedance flag is not set (e.g., the impedance threshold is not met), then the digital device may determine, at 1372, whether any more aggressive power curves remain to be implemented. If so, the digital device may point the routine 1362 to the next, more aggressive power curve at 1374. The routine 1362 may continue (1378) to deliver power according to the new power curve at 1364. If all available power curves have been applied, then the digital device may disable calculating and checking of accumulated energy for the remainder of the tissue operation at 1376.

If the impedance flag is set at 1370 (e.g., the impedance threshold has been met), then the digital device may disable calculating and checking of accumulated energy for the remainder of the tissue operation at 1376. It will be appreciated that, in some embodiments, accumulated energy calculation may be continued, while 1370, 1372, 1374, and 1376 may be discontinued. For example, the generator 102, 220 and/or digital device may implement an automated shut-off when accumulated energy reaches a predetermined value.

Figure 18:
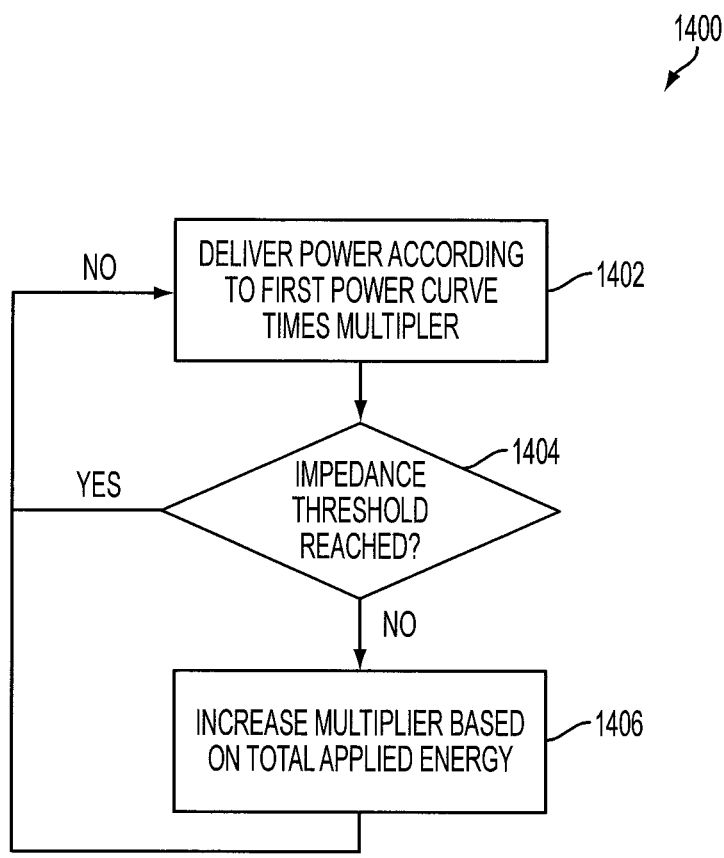
FIG. 18 illustrates one embodiment of a process flow for applying one or more power curves to a tissue bite.

FIG. 18 illustrates one embodiment of a process flow 1400 for applying one or more power curves to a tissue bite. For example, the process flow 1400 may be implemented by the generator 102, 220 (e.g., the digital device of the generator 102, 220). At 1402, the generator 102, 220 may deliver a power curve to the tissue. The power curve may be derived by applying a multiplier to a first power curve. At 1404, the generator 102, 220 may determine if the impedance threshold has been met. If the impedance threshold has not been met, the generator 102, 220 may increase the multiplier as a function of the total applied energy. This may have the effect of increasing the aggressiveness of the applied power curve. It will be appreciated that the multiplier may be increased periodically or continuously. For example, the generator 102, 220 may check the impedance threshold (1404) and increase the multiplier (1406) at a predetermined periodic interval. In various embodiments, the generator 102, 220 may continuously check the impedance threshold (1404) and increase the multiplier (1406). Increasing the multiplier as a function of total applied energy may be accomplished in any suitable manner. For example, the generator 102, 220 may apply a deterministic equation that receives total received energy as input and provides a corresponding multiplier value as output. Also, for example, the generator 102, 220 may store a look-up table that comprises a list of potential values for total applied energy and corresponding multiplier values. According to various embodiments, the generator 102, 220 may provide a pulsed drive signal to tissue (e.g., via one of the surgical devices 104, 106). According to various embodiments, when the impedance threshold is met, the multiplier may be held constant. The generator 102, 220 may continue to apply power, for example, until a termination threshold is reached. The termination threshold may be constant, or may depend on the final value of the multiplier.

In some embodiments utilizing a pulsed drive signal, the generator 102, 220 may apply one or more composite load curves to the drive signal, and ultimately to the tissue. Composite load curves, like other power curves described herein, may define a level of power to be delivered to the tissue as a function of a measured tissue property or properties (e.g., impedance). Composite load curves may, additionally, define a series of pulses that may be delivered to the tissue. In some embodiments, the number, pulse width and/or other characteristics of the pulses may be predetermined and/or determined based on measured tissue properties.

Figure 19:
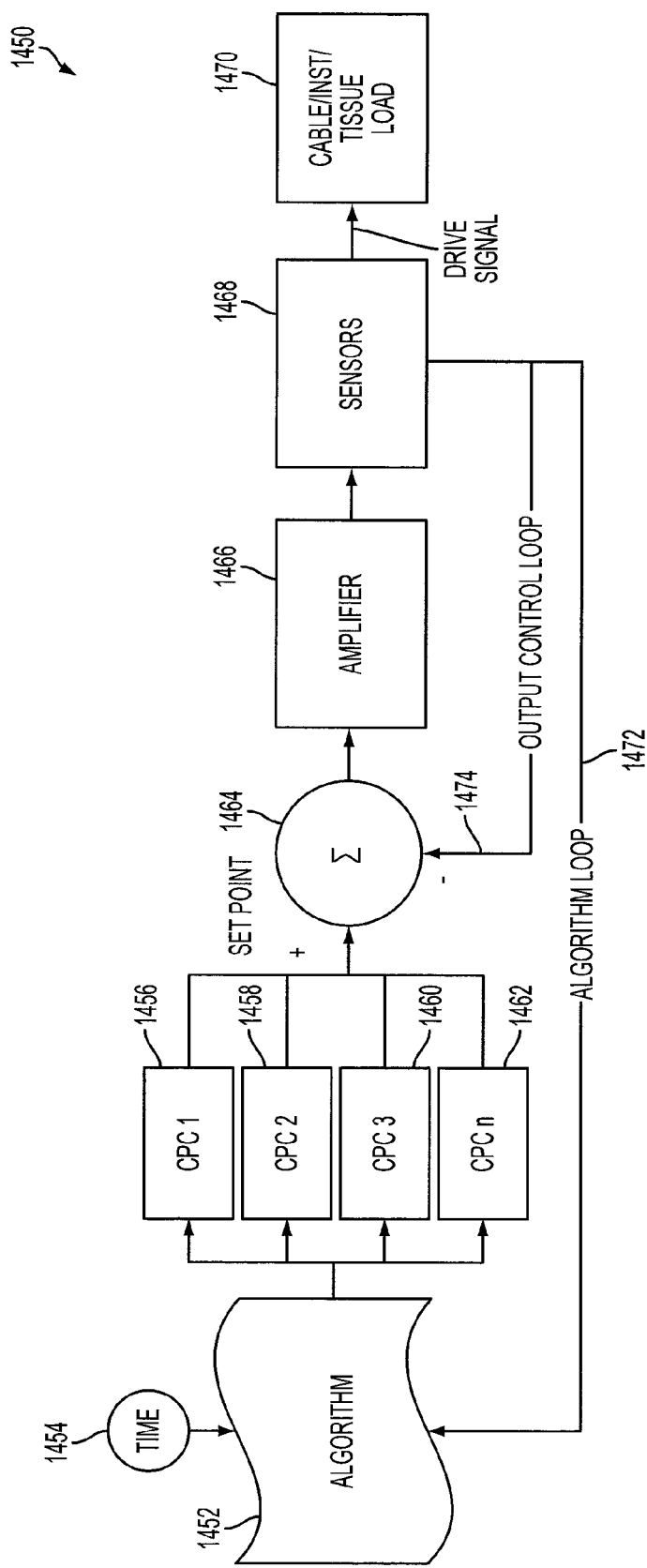
FIG. 19 illustrates one embodiment of a block diagram describing the selection and application of composite load curves by the generator.

FIG. 19 illustrates one embodiment of a block diagram 1450 describing the selection and application of composite load curves by the generator 102, 220. It will be appreciated that the block diagram 1450 may be implemented with any suitable type of generator or surgical device. According to various embodiments, the block diagram 1450 may be implemented utilizing an electrosurgical device, such as the device 106 described above with respect to FIGS. 4-7 and 9-12. Also, in various embodiments, the block diagram 1450 may be implemented with an ultrasonic surgical device, such as the surgical device 104 described above with respect to FIGS. 2-3, 3A and 3B. In some embodiments, the block diagram 1450 may be utilized with a surgical device having cutting as well as coagulating capabilities. For example, an RF surgical device, such as the device 106, may comprise a cutting edge, such as the blade 175 for severing tissue either before or during coagulation.

Referring back to FIG. 19, an algorithm 1452 may be executed, for example by a digital device of the generator 102, 220 to select and apply composite load curves 1456, 1458, 1460, 1462. The algorithm 1452 may receive a time input from a clock 1454 and may also receive loop input 1472 from sensors 1468. The loop input 1472 may represent properties or characteristics of the tissue that may be utilized in the algorithm 1452 to select and/or apply a composite load curve. Examples of such characteristics may comprise, for example, current, voltage, temperature, reflectivity, force applied to the tissue, resonant frequency, rate of change of resonant frequency, etc. The sensors 1468 may be dedicated sensors (e.g., thermometers, pressure sensors, etc.) or may be software implemented sensors for deriving tissue characteristics based on other system values (e.g., for observing and/or calculating voltage, current, tissue temperature, etc., based on the drive signal). The algorithm 1452 may select one of the composite load curves 1456, 1458, 1460, 1462 to apply, for example based on the loop input 1472 and/or the time input from the clock 1454. Although four composite load curves are shown, it will be appreciated that any suitable number of composite load curves may be used.

The algorithm 1452 may apply a selected composite load curve in any suitable manner. For example, the algorithm 1452 may use the selected composite load curve to calculate a power level and one or more pulse characteristics based on tissue impedance (e.g., currently measured tissue impedance may be a part of, or may be derived from, the loop input) or resonant frequency characteristics of a ultrasonic device 104. Examples of pulse characteristics that may be determined based on tissue impedance according to a composite load curve may include pulse width, ramp time, and off time.

At set point 1464, the derived power and pulse characteristics may be applied to the drive signal. In various embodiments, a feedback loop 1474 may be implemented to allow for more accurate modulation of the drive signal. At the output of the set point 1464, the drive signal may be provided to an amplifier 1466, which may provide suitable amplification. The amplified drive signal may be provided to a load 1470 (e.g., via sensors 1468). The load 1470 may comprise the tissue, the surgical device 104, 106, and/or any cable electrically coupling the generator 102, 220 with the surgical device 104, 106 (e.g., cables 112, 128).

Figure 20:
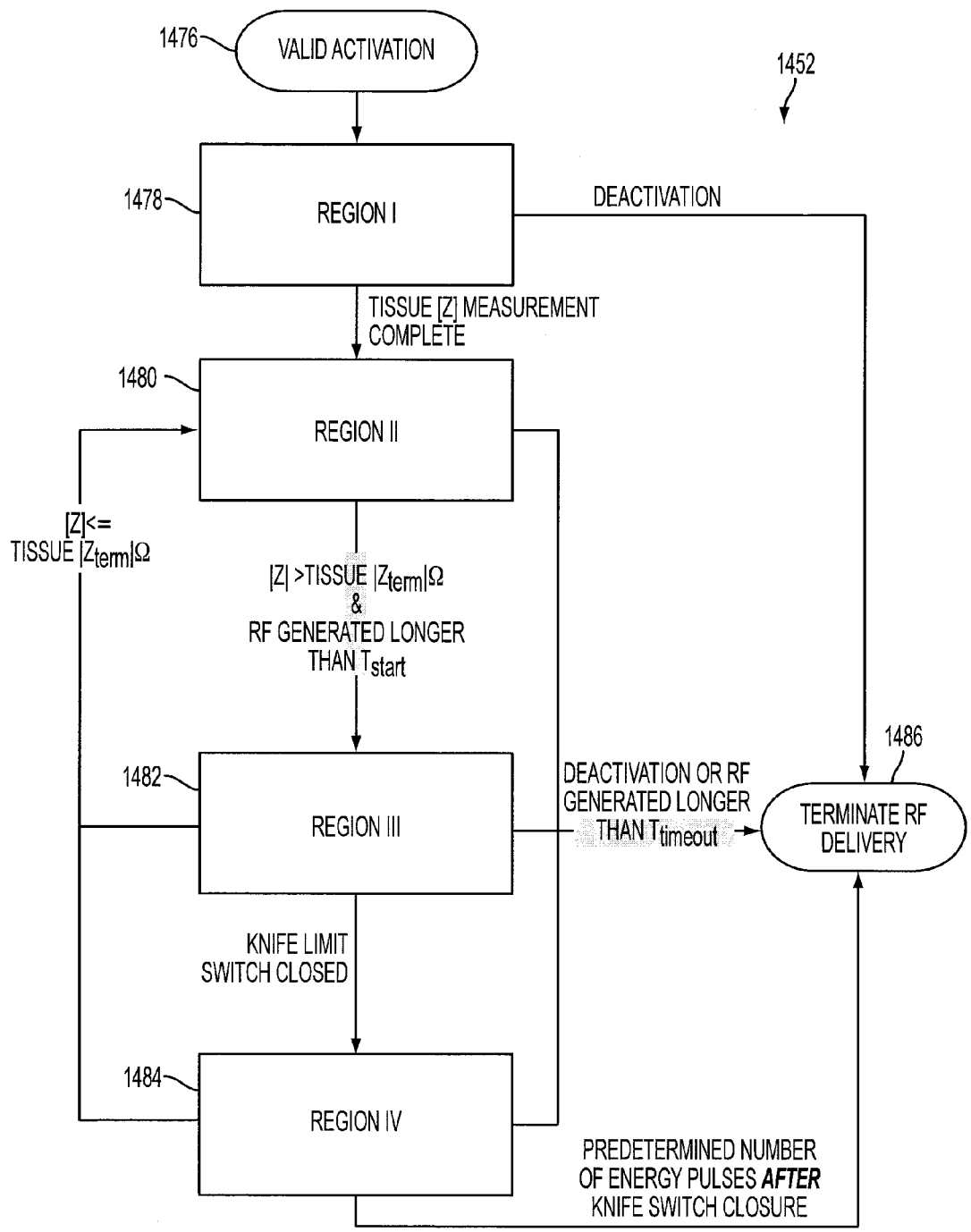
FIG. 20 shows a process flow illustrating one embodiment of the algorithm of FIG. 19.

FIG. 20 illustrates shows a process flow illustrating one embodiment of the algorithm 1452, as implemented by the generator 102, 220 (e.g., by a digital device of the generator 102, 220). The algorithm 1452 may be activated at 1476. It will be appreciated that the algorithm 1452 may be activated in any suitable manner. For example, the algorithm 1452 may be activated by a clinician upon actuation of the surgical device 104, 106 (e.g., by pulling or otherwise actuating a jaw closure trigger 138, 142, switch, handle, etc.).

According to various embodiments, the algorithm 1452 may comprise a plurality of regions 1478, 1480, 1482, 1484. Each region may represent a different stage of the cutting and coagulation of a tissue bite. For example, in the first region 1478, the generator 102, 220 may perform an analysis of initial tissue conditions (e.g., impedance). In the second region 1480, the generator 102, 220 may apply energy to the tissue in order to prepare the tissue for cutting. In the third or cut region 1482, the generator 102, 220 may continue to apply energy while the surgical device 104, 106 cuts the tissue (e.g., with the electrosurgical device 106, cutting may be performed by advancing the blade A18). In the fourth or completion region 1484, the generator 102, 220 may apply energy post-cut to complete coagulation.

Referring now to the first region 1478, the generator 102, 220 may measure any suitable tissue condition or conditions including, for example, current, voltage, temperature, reflectivity, force applied to the tissue, etc. In various embodiments, an initial impedance of the tissue may be measured according to any suitable manner. For example, the generator 102, 220 may modulate the drive signal to provide a known voltage or currency to the tissue. Impedance may be derived from the known voltage and the measured current or vice versa. It will be appreciated that tissue impedance may alternately or additionally be measured in any other suitable manner. According to the algorithm 1452, the generator 102, 220 may proceed from the first region 1478 to the second region 1480. In various embodiments, the clinician may end the algorithm 1452 in the first region 1478, for example, by deactivating the generator 102, 220 and/or the surgical device 104, 106. If the clinician terminates the algorithm 1542, RF (and/or ultrasonic) delivery may also be terminated at 1486.

In the second region 1480, the generator 102, 220 may begin to apply energy to the tissue via the drive signal to prepare the tissue for cutting. Energy may be applied according to the composite load curves 1456, 1458, 1460, 1462, as described below. Applying energy according to the second region 1480 may comprise modulating pulses onto the drive signal according to some or all of the composite load curves 1456, 1458, 1460, 1462. In various embodiments, the composite load curves 1456, 1458, 1460, 1462 may be successively applied in order of aggressiveness (e.g., to accommodate various types of tissue-volume clamped in the instrument jaws).

The first composite load curve 1456 may be applied first. The generator 102, 220 may apply the first composite load curve 1456 by modulating one or more first composite load curve pulses onto the drive signal. Each first composite load curve pulse may have a power and pulse characteristics determined according to the first composite load curve and considering measured tissue impedance. Measured tissue impedance for the first pulse may be the impedance measured at the first region 1478. In various embodiments, the generator 102, 220 may utilize all or a portion of the first composite load curve pulses to take additional measurements of tissue impedance or resonant frequency. The additional measurements may be used to determine the power and other pulse characteristics of a subsequent pulse or pulses.

Figure 21:
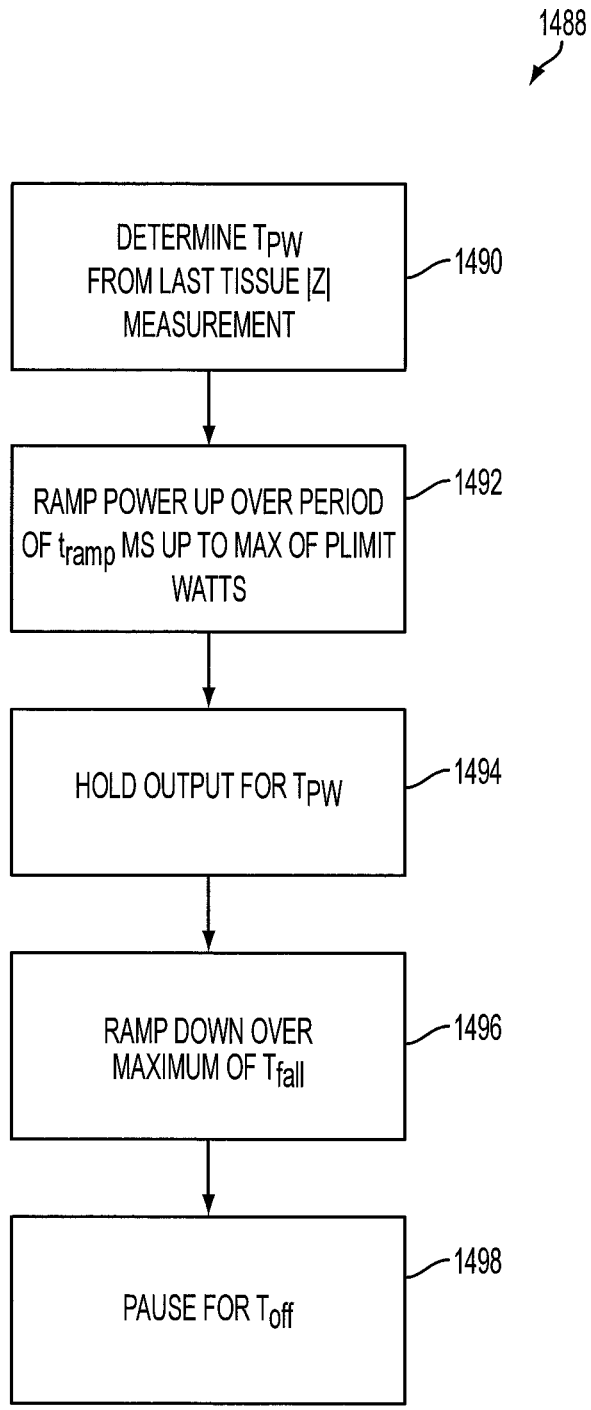
FIG. 21 illustrates one embodiment of a process flow for generating a first composite load curve pulse.

FIG. 21 illustrates one embodiment of a process flow 1488 for generating a first composite load curve pulse. The process flow 1488 may be executed by the generator 102, 220 (e.g., by a digital device of the generator 102, 220), for example, as a part of the algorithm 1452. At 1490, the generator 102, 220 may calculate a pulse width ($T_{pw}$). The pulse width may be determined considering the most recent measured tissue impedance (Z) and according to the first composite load curve 1456.

At 1492, the generator 102, 220 may ramp the power of the drive signal up to a pulse power (PLimit) over a ramp time ($t_{ramp}$), thereby applying the pulse to the tissue. The pulse power may be determined, again, considering the most recent measured tissue impedance (Z) and according to the first composite load curve 1456. The ramp time may be determined according to the composite load curve considering tissue impedance or may be constant (e.g., constant for all first composite load curve pulses, constant for all pulses, etc.). The generator 102, 220 may apply the pulse power to the drive signal in any suitable manner including, for example, modulating a current and/or voltage provided by the drive signal. According to various embodiments, the drive signal may be an alternating current (A/C) signal, and therefore the pulse itself may comprise multiple cycles of the drive signal.

The drive signal may be held at the pulse power for the pulse width at 1494. At the conclusion of the pulse, the drive signal may be ramped down, at 1496, over a fall time ($T_{fall}$). The fall time may be determined according to the first composite load curve considering tissue impedance, or may be constant (e.g., constant for all first composite load curve pulses, constant for all pulses, etc.). It will be appreciated that, depending on the embodiment, the ramp time and fall time may or may not be considered part of the pulse width.

At 1498, the generator 102, 220 may pause for an off time ($T_{off}$). Like the ramp time and fall time, the off time may be determined according to the first composite load curve considering tissue impedance, or may be constant (e.g., constant for all first composite load curve pulses, constant for all pulses, etc.).

At the completion of the off time, the generator 102, 220 may repeat the process flow 1488 as long as the first composite load curve 1456 is applied. According to various embodiments, the generator 102, 220 may apply the first composite load curve 1456 for a predetermined amount of time. Accordingly, the process flow 1488 may be repeated until the predetermined amount of time has elapsed (e.g., as determined based on the time input received from the clock 1454). Also, in various embodiments, the first composite load curve may be applied for a predetermined number of pulses. Because the applied pulse width varies according to measured tissue impedance, the total time that the first composite load curve is applied may also vary with measured tissue impedance. According to various embodiments, the first composite load curve 1456 (as well as the other composite load curves 1458, 1460, 1462) may specify decreasing pulse widths as tissue impedance increases. Therefore, a higher initial tissue impedance may lead to less time spent in the first composite load curve.

Upon completion of the first composite load curve 1456, the generator 102, 220 may successively apply the remaining consolidated load curves 1458, 1460, 1462 throughout the application of the second region 1480. Each load curve 1458, 1460, 1462 may be applied in a manner similar to that of the load curve 1456 described above. For example, pulses according to a current load curve may be generated until the completion of that load curve (e.g., the expiration of a predetermined amount of time or a predetermined number of pulses). The predetermined number of pulses may be the same for each composite load curve 1456, 1458, 1460, 1462 or may be different. According to various embodiments, pulses according to the load curves 1458, 1460, 1462 may be generated in a manner similar to process flow 1488, except that pulse power, pulse width and, in some embodiments, ramp time, fall time, and off time, may be derived according to the current composite load curve.

The second region 1480 may be terminated upon the occurrence of various events. For example, if the total RF application time has exceeded a timeout time, then the generator 102, 220 may end the tissue operation by terminating RF (and/or ultrasonic) delivery at 1486. Also, various events may cause the generator 102, 220 to transition from the second region 1480 to the third region 1482. For example, the generator 102, 220 may transition to the third region 1482 when the tissue impedance (Z) exceeds a threshold tissue impedance ($Z_{term}$) and RF energy has been delivered for at least more than a minimum time ($T_{start}$). The threshold tissue impedance may be an impedance and/or an impedance rate of change indicating that the tissue bite is adequately prepared for cutting by the blade 175.

According to various embodiments, if the final load curve 1462 is completed in the second region 1480 before completion of the second region 1480, then the final power curve 1462 may be continuously applied, for example, until the tissue impedance threshold is met, the maximum second region time is reached and/or the timeout time is reached. Also, it will be appreciated that, with some tissue cuts, the second region 1480 may be completed before all available consolidated load curves 1456, 1458, 1460, 1462 are executed.

At the third region 1482, the generator 102, 220 may continue to modulate pulses onto the drive signal. Generally, third region pulses may be modulated onto the drive signal according to any suitable manner including, for example, that described above with reference to the process flow 1488. The power and pulse characteristics of the third region pulses may be determined according to any suitable method and, in various embodiments, may be determined based on the composite load curve that was being executed at the completion of the second region 1480 (the current load curve). According to various embodiments, the current load curve may be utilized to determine the pulse power of third region pulses, while the pulse characteristics (e.g., pulse width, ramp time, fall time, off time, etc.) may be constant regardless of composite load curve. In some embodiments, the third region 1482 may utilize a third-region-specific composite load curve that may be one of the load curves 1456, 1458, 1460, 1462 utilized in the second region 1480, or may be a different composite load curve (not shown).

The generator 102, 220 may continue to execute the third region 1482 until receiving an indication that the tissue cut is complete. In embodiments utilizing surgical implements having a blade, such as 175, the indication may be received when the blade 175 reaches its distal-most position, as shown in FIG. 6. This may trip a knife limit sensor (not shown) indicating that the blade 175 has reached the end of its throw. Upon receiving the indication that the tissue cut is complete, the generator 102, 220 may continue to the fourth region 1484. It will also be appreciated that, in some embodiments, the generator 102, 220 may transition from the third region 1482 directly to RF (and/or ultrasonic) termination at 1486, for example, if the timeout time has been reached.

In the fourth region 1484, the generator 102, 220 may provide an energy profile designed to complete coagulation of the now-cut tissue. For example, according to various embodiments, the generator 102, 220 may provide a predetermined number of pulses. The pulses may be provided in a manner similar to that described above with respect to the process flow 1488. The power and pulse characteristics of the pulses may be determined according to any suitable manner. For example, power and pulse characteristics of the fourth region pulses may be determined based on the current composite load curve, the third-region-specific load curve, or a fourth-region-specific composite load curve. In some embodiments, power may be determined based on the current composite load curve, while pulse characteristics may be fourth region-specific. Also, according to various embodiments, the power and pulse characteristics of fourth region pulses may be determined independent of the current composite load curve.

According to various embodiments, the generator 102, 220 may be programmed to modify the application of power curves based on tissue response. In various embodiments, the generator 102, 220 may apply a first power curve until a predetermined condition or set of conditions is met. When the condition or set of conditions is met, the generator 102, 220 applies a more aggressive power curve. For example, with respect to process flows 1330, 1340, 1350 and 1362, the generator 102, 220 increments from one power curve to a next most aggressive power curve when the total energy delivered during the first power curve exceeds a threshold energy level and an impedance threshold is reached. With respect to the process flow 1400, the generator 102, 220 increments from one power curve to a next most aggressive power curve when an impedance threshold is met. With respect to 1450, 1452 and 1488, the generator 102, 220 increments from one composite load curve to a next composite load curve when the number of pulses called for by the first composite load curve have been delivered (e.g., provided on the drive signal). In some embodiments, such as those utilizing larger end effectors to treat larger tissue bites, applying power curves in this manner needlessly increases the time required to treat tissue. For example, when an initial applied composite load curve of process flows 1450, 1452 and 1488 is not aggressive enough to treat tissue in a timely manner, the surgical generator 102, 220 may, in some embodiments, continue to apply the initial composite load curve until the set of conditions are otherwise met (e.g., the total number of pulses called for by the load curve is delivered).

Figure 22:
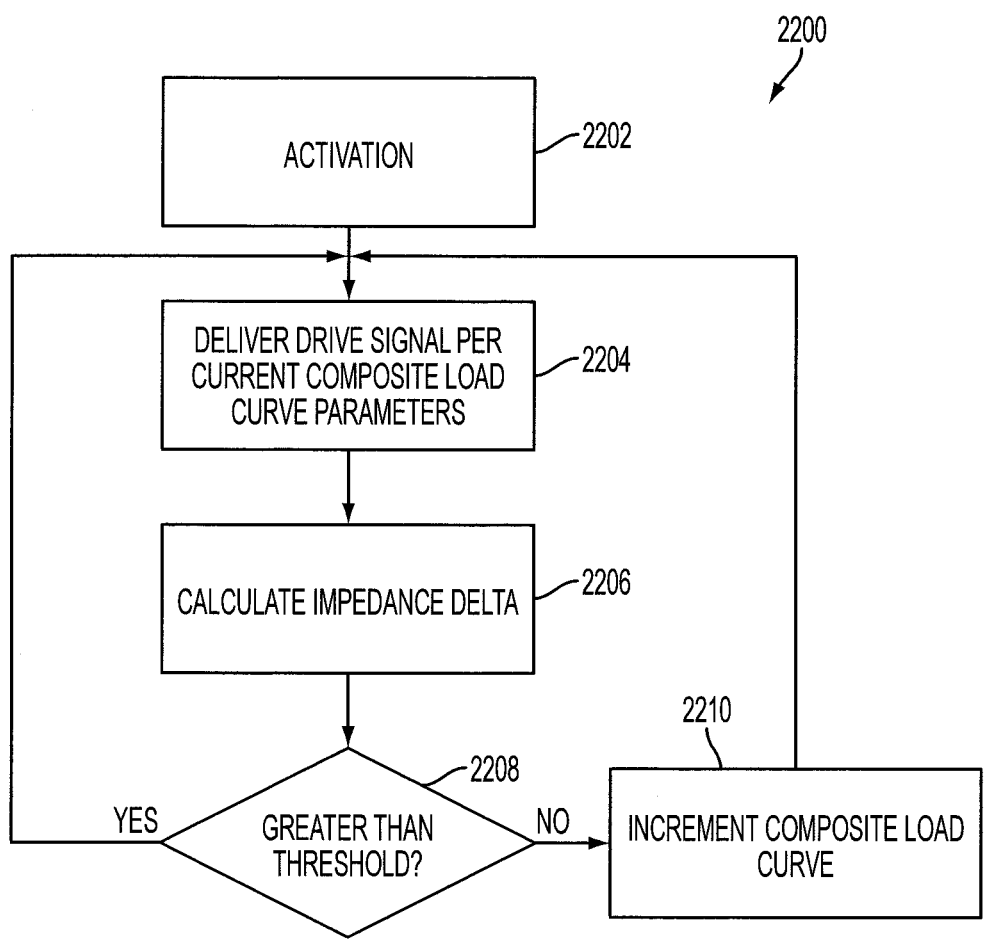
FIG. 22 illustrates one embodiment of a process flow that may be executed by the generator to switch between power curves during tissue treatment.

FIG. 22 illustrates one embodiment of a process flow 2200 that may be executed by the generator 102, 220 to switch between composite load curves during tissue treatment. For example, the process flow 2200 may be executed in parallel to another process flow for incrementing through composite load curves, such as the one or more of the process flows 1450, 1452 and 1488. In this way, the process flow 2200 may cause the generator to increment from one composite load curve to another before the completion of the first composite load curve. At 2202, the generator 102, 220 may activate to initiate a tissue bite. At 2204, the generator 102, 220 may deliver a drive signal according to parameters of a composite load curve. The composite load curve may be determined, for example, as described herein with respect to the process flows 1450, 1452 and 1488. For example, the first composite load curve applied after activation may be the composite load curve 1456 described, for example, at FIG. 19. At 2206, the generator 102, 220 may calculate an impedance difference. The impedance difference may describe a difference in the impedance of the tissue between a first time during the delivery of the drive signal and a second time during the delivery of the drive signal. The impedance difference may be measured directly by electrosurgical electrodes 177, 179, electrodes 159, 157, the blade 151 and conductive jacket 472, etc. In some embodiments utilizing an ultrasonic device, the impedance difference may be measured indirectly by monitoring a difference in impedance of the transducer 114.

If, at 2208, the impedance difference is greater than a threshold impedance difference, it may indicate that the first composite load curve is having a sufficient effect on the tissue. Accordingly, the generator 102, 220 may continue to deliver the drive signal according to the first composite load curve, at 2204, for example, until the composite load curve is otherwise completed, as described herein above. If the impedance difference, however, is less than the threshold impedance difference, it may indicate that the composite load curve is not having a sufficient effect on the tissue. Accordingly, the generator 102, 220 may increment to the next composite load curve at 2210, and then provide the drive signal, at 2204, according to the parameters of the next power curve. The impedance threshold may be any suitable threshold. In some embodiments, the impedance threshold is an absolute threshold (e.g., an increase of 5 Ω). Also, in some embodiments, the impedance threshold is based on the measured impedance. For example, the impedance threshold may be a percentage change, a percentage of the impedance as measured at the first time, etc. In some embodiments, different thresholds are used based on the composite load curve being applied.

Figure 23A:
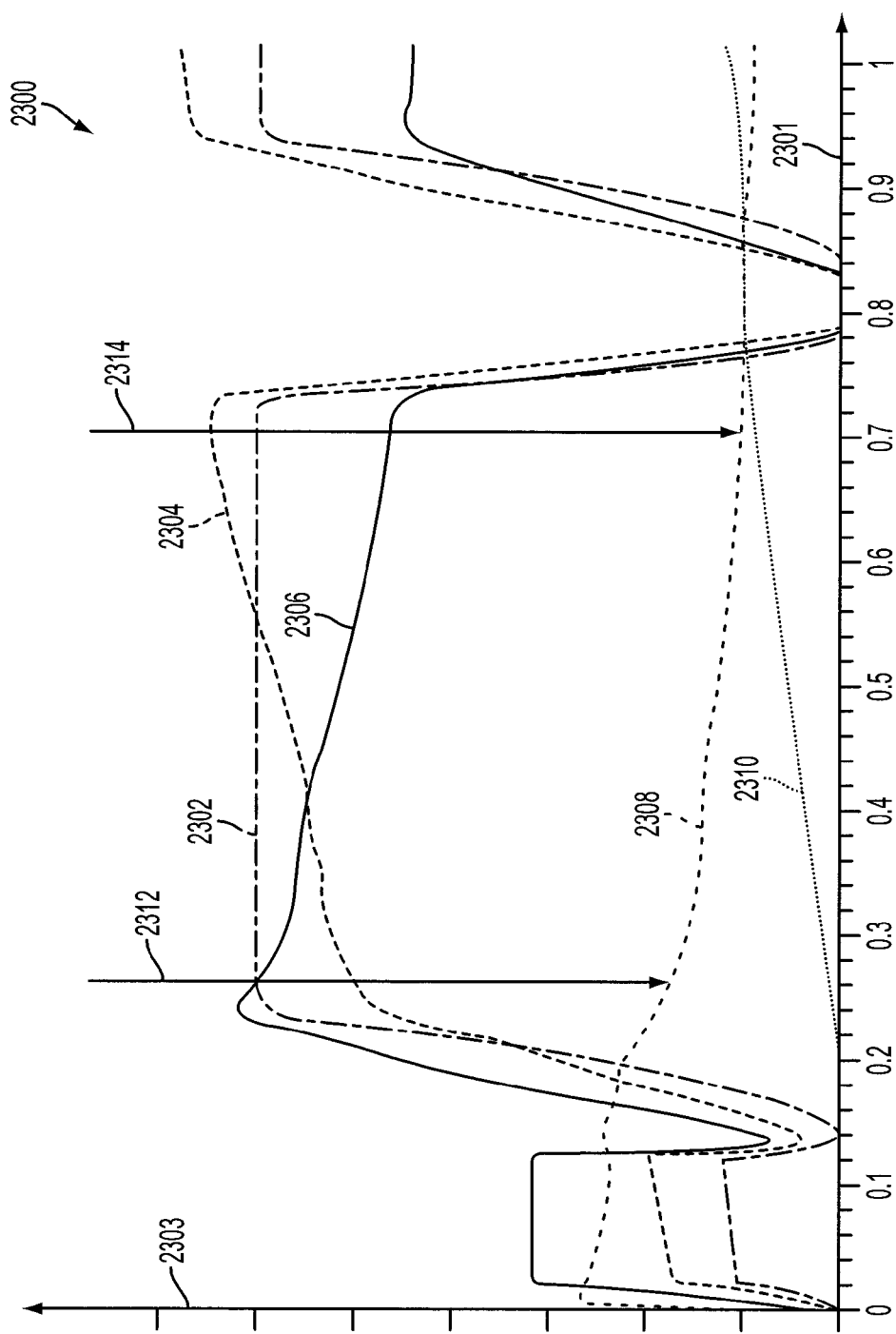
FIG. 23A illustrates a plot showing various properties of one embodiment of a drive signal showing a pulse.

In various embodiments, the impedance difference may be taken across a single pulse of the drive signal. For example, and as described herein, properties of drive signal pulses may be determined based on the composite load curve. FIG. 23A illustrates a plot showing various properties of one embodiment of a drive signal showing a pulse 2300. In FIG. 23A, a horizontal axis 2301 illustrates time and a vertical axis 2303 illustrates magnitude. The drive signal, including the pulse 2300, may be provided to electrosurgical electrodes 177, 179 and/or an ultrasonic transducer 114. The pulse 2300 may be a pulse of a composite load curve, for example, as described herein. The plot of FIG. 23A shows the power 2302, current 2304, voltage 2306, and impedance 2308 occurring when the drive signal is provided to a load (e.g., electrosurgical electrodes 177, 179 and/or the ultrasonic transducer 114). A sum of energy 2310 indicates the total energy provided to tissue since activation. As illustrated in FIG. 23A, the pulse 2300 has a pulse width of approximately 5.5 seconds, though it will be appreciated that pulses of any suitable pulse width may be used.

Figure 23B:
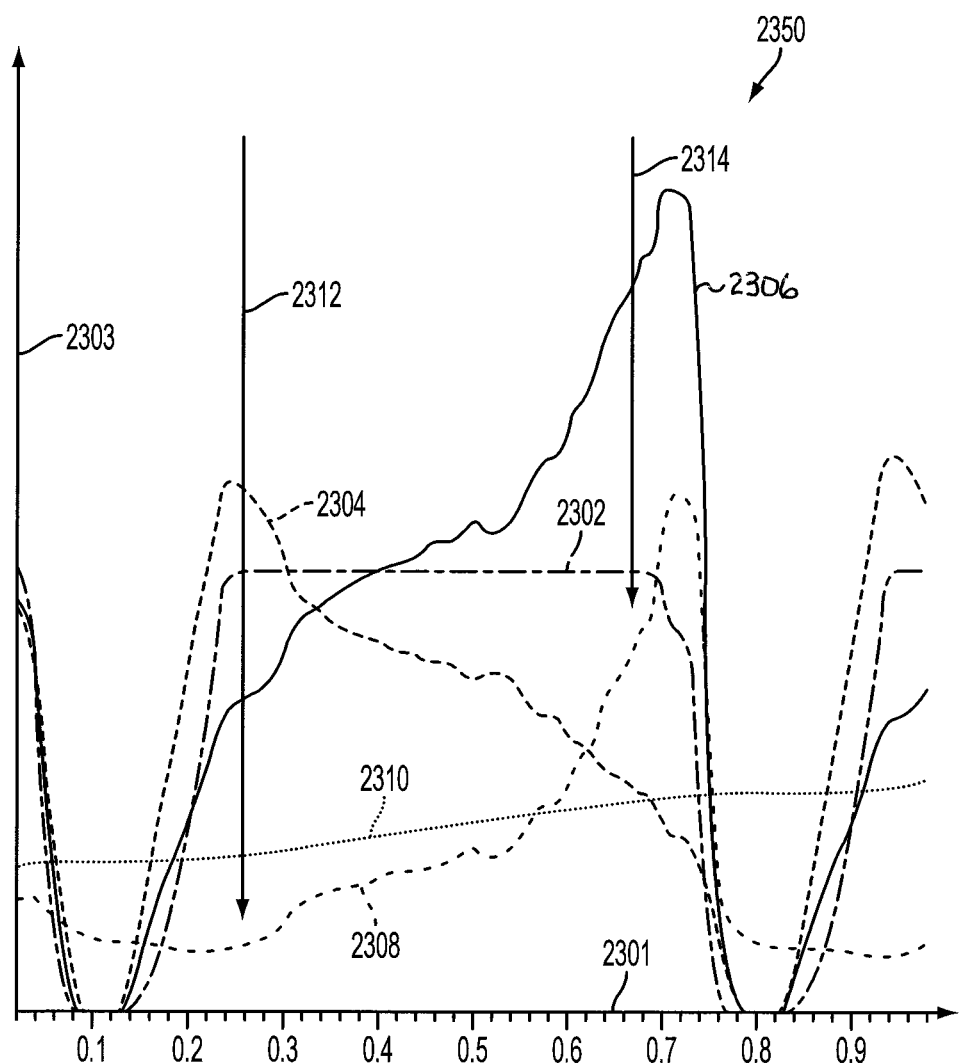
FIG. 23B illustrates a plot showing various properties of one embodiment of a drive signal showing another pulse.

The plot of FIG. 23A illustrates an example placement of first and second sample times 2312, 2314 at which the impedance 2308 may be measured to determine the impedance difference. As illustrated, the first sample time 2312 is at a leading edge of the pulse 2300 and the second sample time 2314 is prior to the trailing edge of the pulse 2300. For example, the generator 102, 220 may be programmed to determine the total pulse width and may take an impedance measurement before the pulse is completed. In the example illustrated in FIG. 23A, the impedance 2308 experienced by the drive signal is lower at the second time 2314 than at the first time 2312. This may indicate that the drive signal is not having a sufficient effect on the tissue, which may cause the generator 102, 220 to jump to a more aggressive composite load curve (e.g., a next most aggressive composite load curve), as illustrated at 2210. FIG. 23B illustrates a plot showing various properties of one embodiment of a drive signal showing another pulse 2350. For the pulse 2350, the impedance experienced by the drive signal increased between the first sample time 2312 and the second sample time 2314. This may indicate that the drive signal is having a sufficient effect on the treated tissue and the generator 102, 220 may continue in the current composite load curve, for example, as shown at 2204. In some embodiments, instead of being taken between sample times in a single pulse, the impedance difference may be taken between any two points or regions in the drive signal. For example, the impedance difference may be taken between the average impedances for two pulses (e.g. consecutive pulses). In a non-pulsed setting, the impedance difference may be taken between two points in time that are, for example, a predetermined time apart.

Figure 24:
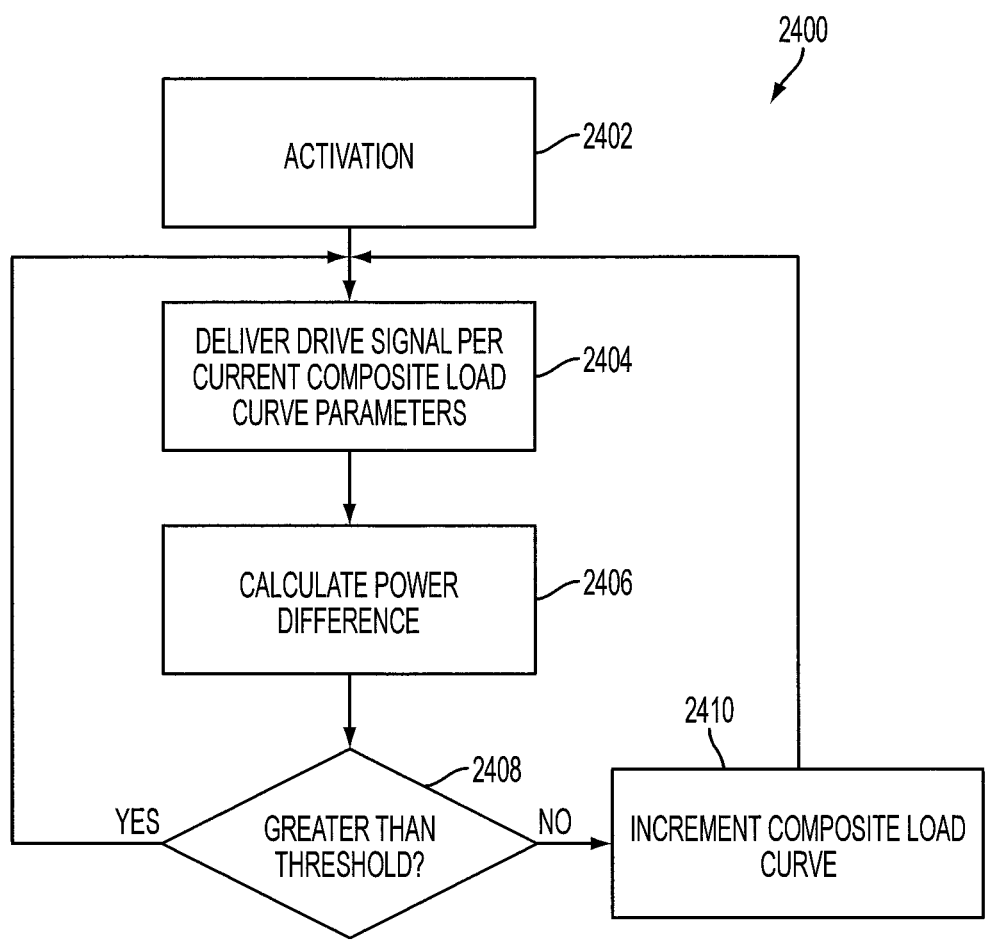
FIG. 24 illustrates another embodiment of a process flow that may be executed by the generator to switch between composite load curves during tissue treatment.

FIG. 24 illustrates another embodiment of a process flow 2400 that may be executed by the generator 102, 220 to switch between composite load curves during tissue treatment based on a difference in delivered power. For example, a drop in the power delivered to tissue may indicate that the drive signal is having a sufficient effect on the tissue. The process flow 2400 may be executed in parallel to another process flow for incrementing through composite load curves, such as the one or more of the process flows 1450, 1452 and 1488. At 2402, the surgical system may be activated on a tissue bite. At 2404, the generator 102, 220 may deliver a drive signal according to a currently applied composite load curve. At 2406, the generator 102, 220 may calculate a power difference. The power difference may indicate whether the power provided to the tissue by the drive signal is increasing or decreasing. The power difference may be taken, for example, between two points and/or two regions of the drive signal. For example, the power difference may be measured between two points and/or regions of the drive signal offset by a predetermined amount of time. Also, for example, the power difference may be measured between two pulses (e.g., consecutive pulses). The power at a pulse may be taken at points on the pulses (e.g., equivalent points on consecutive pulses) or as an average or other aggregation over all or a portion of the pulses.

At 2408, the generator 102, 220 may determine whether the power difference greater than a power threshold. If the power difference is greater than the power threshold, it may indicate that the drive signal is having a sufficient effect on the tissue, so the generator 102, 220 may continue to apply the drive signal according to the current power curve at 2404, for example, until application of the composite load curve is otherwise complete as described herein above. If the power difference is less than the power threshold, it may indicate that the drive signal is not having a sufficient effect on the tissue, the generator 102, 220 may increment, at 2416, to a more aggressive composite load curve (e.g., the next most aggressive composite load curve) and proceed to 2404 as described.

Figure 25A:
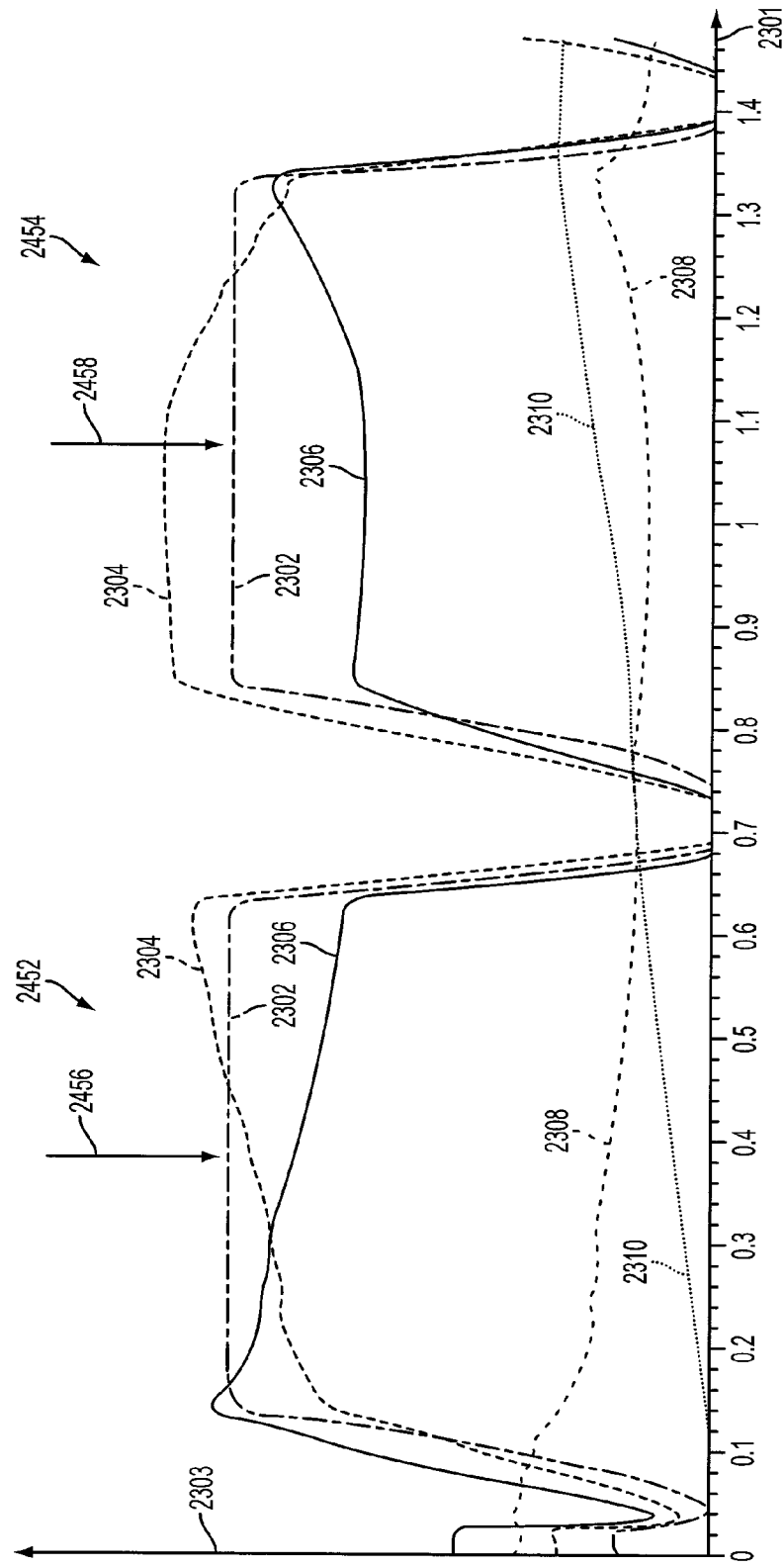
FIG. 25A illustrates a plot showing various properties of one embodiment of a drive signal showing two pulses.

FIG. 25A illustrates a plot showing various properties of one embodiment of a drive signal showing two pulses 2452, 2454. For example, FIG. 25A illustrates a sample time 2456 during the first pulse 2452 and a sample time 2458 during the second pulse 2454. The power 2302 of each pulse, for purposes of determining the power difference, may be taken, for example, at the sample times 2456, 2458. In some embodiments, however, the power 2302 of each pulse may be averaged over the respective pulses 2452, 2454. In the example of FIG. 25A, the power 2302 is consistent and similar over both pulses 2452, 2454 and may be less than the power threshold. This may indicate that the drive signal is not having a sufficient effect on tissue, causing the composite load curve to be incremented at 2416. FIG. 25B illustrates a plot showing various properties of one embodiment of a drive signal showing two pulses 2460, 2462. Sample times 2464 and 2466 are also illustrated. As shown, the power delivered to the tissue drops between the pulse 2460 and the pulse 2462 measured either as a difference between the average power of each pulse 2460, 2462 or a difference between the instantaneous power at the sample points 2464, 2466. As illustrated in FIG. 25B, the difference is larger than the power difference threshold, indicating that the drive signal is having a sufficient effect on tissue. Accordingly, the generator 102, 220 may continue with the current composite load curve.

Although the process flows 2200, 2400 are described as incrementing composite load curves based on an impedance difference (2200) and a power difference (2400), any suitable tissue property difference may be used. Suitable tissue property differences may relate to tissue changes indicating that the drive signal is having an effect on the tissue, or proxies therefor. Examples of tissue property differences that may be used include, for example, current, voltage, tissue temperature, reflectivity, force applied to the tissue (e.g., pressure between jaw members 167, 169 or between blade 151 and clamp arm 155), resonant frequency, rate of change of resonant frequency, etc. The nature of different tissue properties may lead to differences in tissue property difference thresholds. For example, when impedance difference is used, an impedance increase may indicate increasing tissue effect. When power difference is used, a drop in power may indicate increasing tissue effect.

Figure 26:
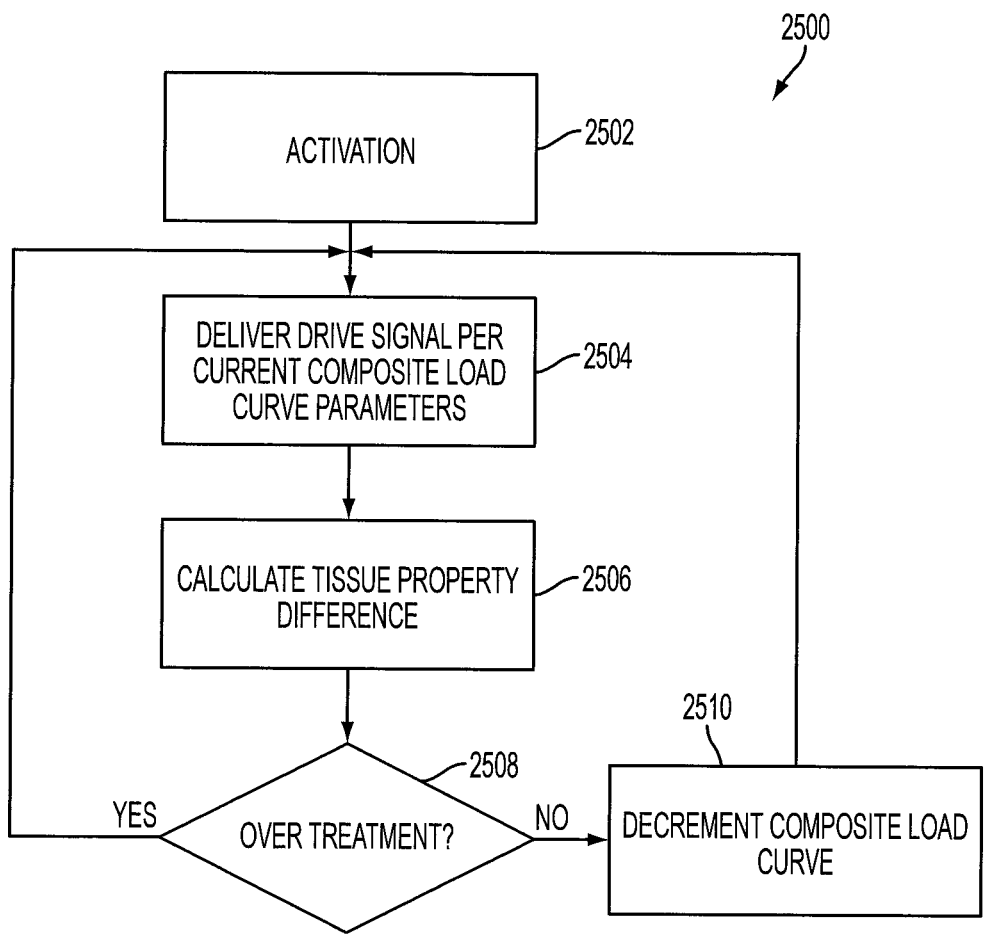
FIG. 26 illustrates a process flow that may be executed by the generator to decrement composite load curves during tissue treatment.

In some embodiments, the generator 102, 220 may also be programmed to decrement from a more aggressive composite load curve to a less aggressive composite load curve. For example, if a load curve that is too aggressive is applied to the drive signal, tissue may be damaged and may form a less ideal seal. FIG. 26 illustrates a process flow 2500 that may be executed by the generator to decrement composite load curves during tissue treatment. The process flow 2500 may be executed in parallel to another process flow for incrementing through composite load curves, such as the one or more of the process flows 1450, 1452 and 1488 and/or may be executed not in parallel with another such process flow. At 2502, the surgical system may be activated on a tissue bite. At 2504, the generator 102, 220 may deliver a drive signal according to a current composite load curve. At 2506, the generator 102, 220 may calculate a tissue property difference. Any suitable tissue property may be used. If the tissue property difference indicates over-treatment of the tissue, at 2508 the generator 102, 220 may decrement at 2510 to a less aggressive composite load curve (e.g., the next less aggressive composite load curve). Overtreatment may be determined, for example, by comparing the tissue property difference to a difference threshold. Different tissue properties and difference thresholds may have different relationships to one another. For example, when an impedance difference is used, the generator 102, 220 may decrement the composite load curve 2510 when the impedance difference is too positive. When a power difference is used, the generator 102, 220 may decrement the composite load curve when the power difference drops too much. In various embodiments, at 2508, the generator 102, 220 may compare the tissue property to two thresholds, an increment threshold and a decrement threshold. If the tissue property meets the increment threshold, then generator 102, 220 may increment the composite load curve. If the tissue property meets the decrement threshold, the generator 102, 220 may decrement the composite load curve at 2510. If neither threshold is met, the generator 102, 220 may continue in the current composite load curve, for example, until application of the composite load curve is otherwise completed, for example, as described herein above.

Although the process flows 2200, 2400, 2500 are described in the context of composite load curves, it will be appreciated that they may be executed with respect to other types of power curves as well. For example, with reference to the process flows 1330, 1340, 1350 and 1362, the generator 102, 220 may increment (or decrement) the power curve when the impedance, power or other difference threshold is exceeded, regardless of whether the energy threshold has been reached. Also for example, with reference to the process flow 1400, the generator 102, 220 may increment (or decrement) the power curve when the power, impedance or other difference threshold is exceeded, regardless of whether the instantaneous impedance exceeds the impedance threshold.

Figure 27:
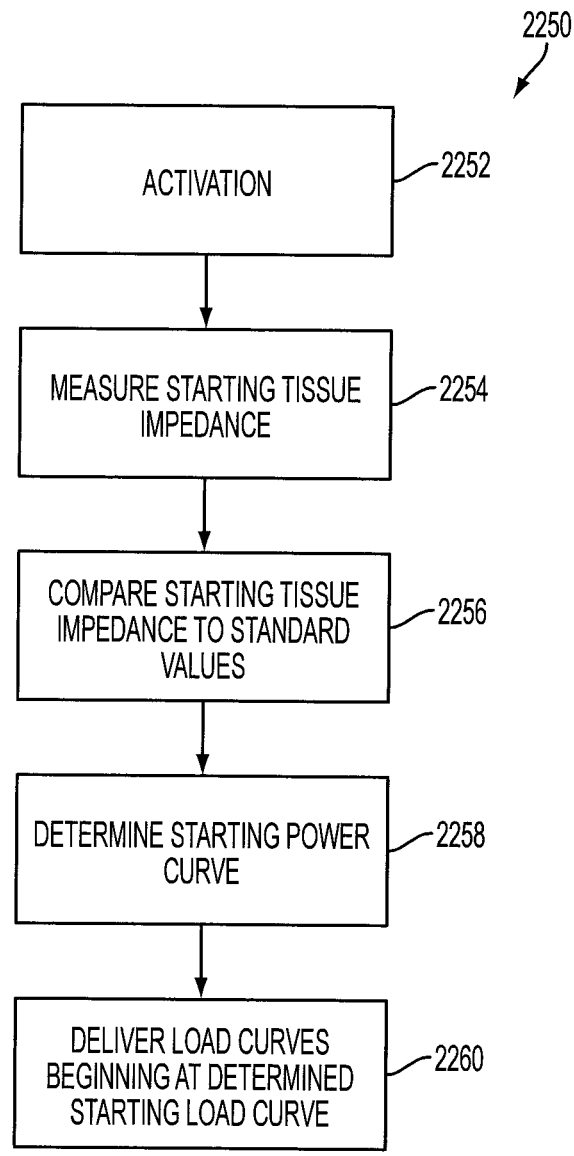
FIG. 27 illustrates a process flow that may be executed by the generator to select an initial power curve.

In various embodiments, the generator 102, 220 may select an appropriate initial composite load curve or other power curve based on one or more tissue properties. FIG. 27 illustrates a process flow 2250 that may be executed by the generator 102, 220 to select an initial power curve. The process flow 2250 may be executed in conjunction with, for example, any of the process flows 1330, 1340, 1350, 1400, 1450, 1452 and 1488 described herein. Activation on a tissue bite may occur at 2252. At 2254, the generator 102, 220 may measure a starting tissue impedance or other starting tissue property. For example, the generator 102, 220 may apply a sensing signal across electrodes in contact with the tissue. When an electrosurgical device is used, the sensing signal may be applied across electrodes 177, 179. When an ultrasonic device is used, the sensing signal may be applied across electrodes 159, 157 and/or conductive jacket 472 and blade 151. In various embodiments, the sensing signal may be non-therapeutic. For example, the impedance sensing signal may have a voltage, current, power, and/or energy level that is not sufficient to significantly affect the tissue. The sensing signal may have any suitable properties that may depend on the particular application. For example, in some embodiments, the sensing signal may have a maximum power of between 1 and 2 Watts, resulting in a maximum voltage of about 5 Volts or less. In some embodiments where the drive signal is pulsed, the sensing signal may be provided out of phase with therapeutic signal such that the sensing signal is provided when the therapeutic signal is "off" (e.g., equal to zero). For example, the pulse width of a sensing signal provided when the therapeutic signal is off may be between 20 and 100 milliseconds. In some embodiments, the starting tissue property may be a tissue impedance, although any suitable tissue property or derivative of tissue property may be used including, for example, tissue impedance, power provided to tissue over the sensing time, tissue temperature, pressure exerted on tissue over the sensing time, etc.

When sensing signal is an alternating current or AC signal, the impedance encountered by the sensing signal may depend on its frequency. In some embodiments, the frequency of the sensing signal may be selected to be offset from the frequency of the drive signal. In some embodiments, the frequency of the sensing signal is offset from the frequency of the drive signal by a factor of between about 10 and about 20. For example, the frequency of the sensing signal may be between ten and twenty times the frequency of the frequency of the drive signal or between one tenth and one twentieth of the frequency of the drive signal. Other offsets between the frequencies of the sensing signal and the drive signal may also be used. This may improve electrical isolation between the sensing signal and the drive signal. Also, for example, offsetting the frequencies of the sensing signal and the drive signal may allow both signals to be applied to the tissue simultaneously. Accordingly, for any of the embodiments described herein, tissue impedance may be measured using a sensing signal provided at the same time that a drive signal is also provided. In an ultrasonic device, the sensing signal may be applied across sensing electrodes 159, 157 and/or the conductive jacket 472 and blade 151 while the drive signal is provided to the transducer 114. For example, in an electrosurgical device, the drive signal and sensing signal may be applied simultaneously across electrodes 177, 179. Also, in some embodiments, the electrosurgical device may comprise separate sensing electrodes similar to 159 and 157. In such an embodiment, the sensing signal may be provided to the sensing electrodes while the drive signal is provided to the electrodes 177, 179. Also, for example, the sensing signal may be set at a frequency where a particular tissue property is more apparent.

At 2256, the generator 102, 220 may compare the measured starting tissue property with one or more standard tissue impedance values. At 2258, based on the comparison, the generator 102, 220 may select a first or initial power curve. For example, each power curve that may potentially be selected as the first power curve is associated with an impedance or range of impedances. When the measured starting tissue impedance corresponds to the impedance associated with a particular power curve, that power curve may be selected as the starting power curve. At 2260, the generator 102, 220 may deliver the drive signal configured according to the selected starting power curve.

Figure 28:
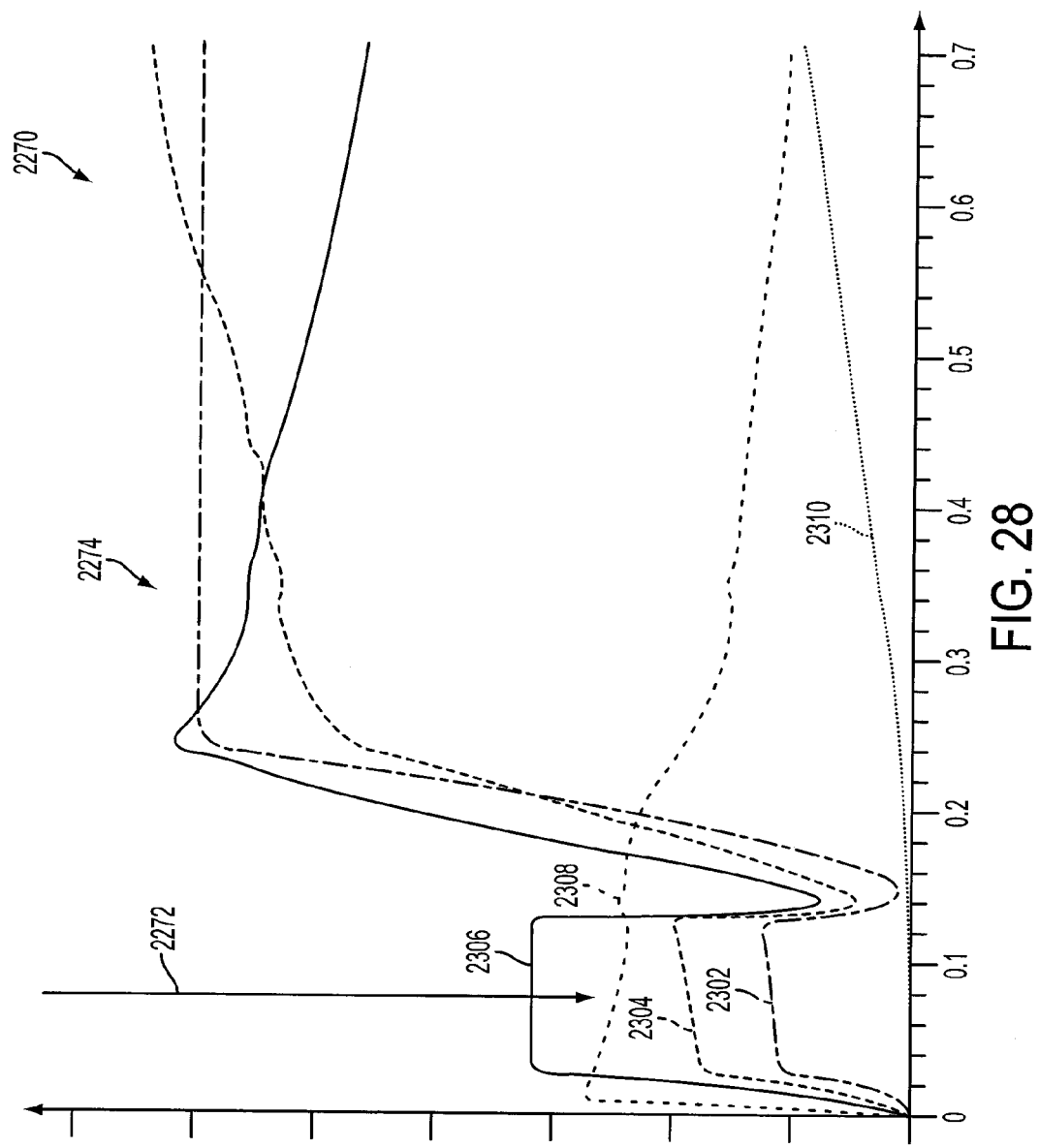
FIG. 28 illustrates a plot showing various properties of one embodiment of an impedance sensing signal.

FIG. 28 illustrates a plot showing various properties of one embodiment of an impedance sensing signal 2272. The impedance sensing signal 2272 is illustrated as a pulse. In various embodiments, the voltage 2306 of the impedance sensing signal may be held constant. The impedance 2302 may then be found utilizing ohm's law based on the measured current 2308. In the embodiment illustrated in FIG. 25, the impedance sensing signal is non-therapeutic. For example, a drive signal 2274 is illustrated next to the impedance sensing signal. The drive signal 2274, as illustrated, brings about a higher voltage 2306, current 2308 and power 2302.

Figure 29:
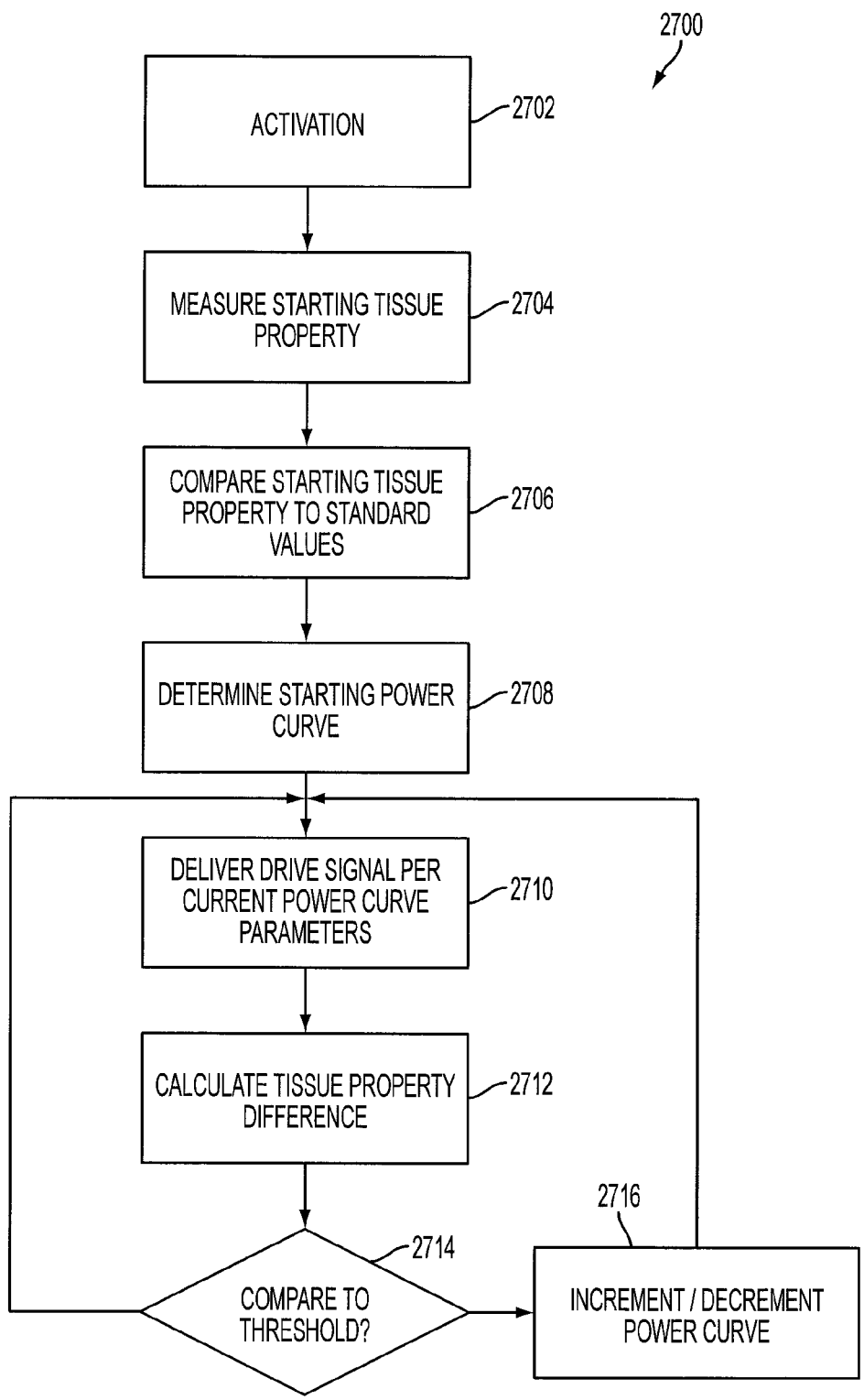
FIG. 29 illustrates a process flow that may be executed by the generator to select an initial power curve and increment and/or decrement a power curve based on a tissue property difference.

FIG. 29 illustrates a process flow 2700 that may be executed by the generator 102, 220 to select an initial power curve and increment and/or decrement a power curve based on a tissue property difference. The process flow 2700 may be executed by the generator 102, 220 by itself, or in conjunction with another process flow for shifting power curves, such as process flows 1330, 1340, 1350, 1400, 1450, 1452 and 1488 described herein. At 2702, the surgical system may activate on a tissue bite. At 2704, the generator 102, 220 may measure a starting tissue property such as, for example, impedance as illustrated above with reference to FIGS. 27-28. At 2706, the generator 102, 220 may compare the starting tissue property to standard values, for example, as described above with respect to 2256 of the process flow 2250. A starting power curve may be determined at 2708. A drive signal according to the starting power curve may be applied to the tissue at 2710. A tissue property difference may be found at 2712 and compared to a threshold (or thresholds) at 2714. If the tissue property difference exceeds an increment or decrement threshold, the drive signal may be modified according to an incremented or decremented power curve at 2716. If no increment or decrement threshold is exceeded, the generator 102, 220 may continue to apply the first power curve.

Although the various embodiments of the devices have been described herein in connection with certain disclosed embodiments, many modifications and variations to those embodiments may be implemented. For example, different types of end effectors may be employed. Also, where materials are disclosed for certain components, other materials may be used. The foregoing description and following claims are intended to cover all such modification and variations.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Various aspects of the subject matter described herein are set out in the following numbered clauses:

1. A surgical system for providing a drive signal to a surgical device for treating tissue, the surgical system comprising:
   a surgical generator, wherein the surgical generator is programmed to:
      deliver the drive signal according to a first composite load curve, wherein the first composite load curve defines a first level of power to be delivered to the tissue as a function of at least one measured property of the tissue, and wherein the first composite load curve defines a plurality of pulses to be sequentially applied to the drive signal;

receive a first tissue measurement indicating a property of the tissue at a first time during the delivery of the drive signal;

receive a second tissue measurement indicating the property of the tissue at a second time during the delivery of the drive signal, wherein the second time is after the first time;

based on the first and second tissue measurements, determine a difference in the property of the tissue between the first time and the second time;

when the difference in the property of the tissue exceeds a difference threshold, deliver the drive signal according to a second composite load curve, wherein the second composite load curve is more aggressive than the first composite load curve.

2. The surgical system of clause 1, wherein the property of the tissue is selected from the group consisting of: an impedance of the tissue; a power provided to the tissue; a temperature of the tissue; and a pressure exerted on the tissue.

3. The surgical system of any of clauses 1-2, wherein the property of the tissue is an impedance of the tissue.

4. The surgical system of any of clauses 1-3, wherein the first time is at a first point of a first pulse of the plurality of pulses and wherein the second time is at a second point of the first pulse.

5. The surgical system of any of clauses 1-4, wherein the change threshold is at least one property selected from the group consisting of: a predetermined impedance value; a percentage of the first tissue measurement; and a multiple of the first tissue measurement.

6. The surgical system of any of clauses 2, 4, wherein the property of the tissue is a power provided to the tissue, and wherein the first time is during a first pulse of the plurality of pulses and the second time is during a second pulse of the plurality of pulses.

7. The surgical system of clause 6, wherein the surgical generator is further programmed to receive a plurality of tissue measurements indicating the property of the tissue during the first pulse, including the first tissue measurement, and a plurality of tissue measurements indicating the property of the tissue during the second pulse, including the second tissue measurement, and wherein determining a change in the power provided to the tissue between the first time and the second time comprises determining a change in an average power provided to the tissue during the first pulse and an average power provided to the tissue during the second pulse.

8. The surgical system of any of clauses 1-7, further comprising:

receiving a third tissue measurement indicating the property of the tissue at a third time during delivery of the drive signal;

receiving a fourth tissue measurement indicating the property of the tissue at a fourth time during delivery of the drive signal; and based on third and fourth tissue measurements, determine a second change in the property between the third time and the fourth time;

when the second change in the property is greater than a second change threshold, deliver the drive signal according to a third composite load curve, wherein the third composite load curve is less aggressive than the second composite load curve.

9. The surgical system of any of clauses 1-8, further comprising:

receiving a third tissue measurement indicating the property of the tissue at a third time during delivery of the drive signal;

receiving a fourth tissue measurement indicating the property of the tissue at a fourth time during delivery of the drive signal; and based on third and fourth tissue measurements, determine a second change in the property between the third time and the fourth time;

when the second change in the property is not greater than a second change threshold, continue to deliver the drive signal according to the second composite load curve.

10. The surgical system of clause 9, further comprising, when the second change in the property is not greater than a second change threshold, continue to deliver the drive signal according to the second composite load curve until a termination of the second composite load curve.

11. The surgical system of any of clauses 1-10, wherein relative to the first composite load curve, the second composite load curve has a higher delivered power over a range of potential tissue impedances.

12. The surgical system of any of clauses 1-11, wherein the property of the tissue is selected from the group consisting of a current of the drive signal, a voltage of the drive signal, a temperature of the tissue, a reflectivity of the drive signal, and a force applied to the tissue.

13. The surgical system of any of clauses 1-12, wherein the surgical generator is further programmed to:

before delivering the drive signal according to the first composite load curve, receive a starting tissue measurement indicating a starting property of the tissue; and based on the pre-treatment property of the tissue, select the first composite load curve.

14. A method of providing a drive signal to a surgical device for treating tissue, the method comprising:

delivering the drive signal to a surgical device according to a first composite load curve, wherein the first composite load curve defines a first level of power to be delivered to the tissue as a function of at least one measured property of the tissue, and wherein the first composite load curve defines a plurality of pulses to be sequentially applied to the drive signal;

receiving a first tissue measurement indicating a property of the tissue at a first time during the delivery of the drive signal;

receiving a second tissue measurement indicating the property of the tissue at a second time during the delivery of the drive signal, wherein the second time is after the first time;

based on the first and second tissue measurements, determining a difference in the property of the tissue between the first time and the second time;

when the difference in the property of the tissue exceeds a difference threshold, delivering the drive signal according to a second composite load curve, wherein the second composite load curve is more aggressive than the first composite load curve.

15. A surgical system for providing a drive signal to a surgical device for treating tissue, the surgical system comprising:

a surgical generator, wherein the surgical generator is programmed to:
  receive a first tissue measurement indicating a property of the tissue;
  based on the first tissue measurement, select a first power curve, wherein the first power curve defines a first level of power to be delivered to the tissue as a function of at least one measured property of the tissue;
  deliver the drive signal according to the composite power curve.

16. The surgical system of clause 15, further comprising:
a first electrode;
a second electrode; and
wherein the surgical generator is further programmed to:
  applying an impedance sensing signal to the tissue via the first and second electrodes;
  determine the property of the tissue based on the impedance sensing signal.

17. The surgical system of clause 16, wherein applying the impedance sensing signal comprises applying the impedance sensing signal for an impedance sensing signal time period.

18. The surgical system of clause 17, wherein the surgical generator is further configured to:
  hold a voltage of the sensing signal constant during the impedance sensing time period; and
  receive an indication of a current of the sensing signal during the impedance sensing time;
  based on the current, determine an impedance of the tissue.

19. The surgical system of any of clauses 15-18, wherein the property of the tissue is selected from the group consisting of: an impedance of the tissue; a power provided to the tissue; a temperature of the tissue; and a pressure exerted on the tissue.

We claim:

1. A surgical system for providing a drive signal to a surgical device for treating tissue, the surgical system comprising:
  a surgical generator, wherein the surgical generator is programmed to:
  deliver the drive signal according to a first composite load curve, wherein the first composite load curve defines a first level of power to be delivered to the tissue as a function of at least one measured property of the tissue, and wherein the first composite load curve defines a plurality of pulses to be sequentially applied to the tissue;
  receive a first tissue measurement over a period of a pulse of the plurality of pulses of the drive signal indicating a property of the tissue at a first time during the delivery of the pulse of the plurality of pulses of the drive signal;
  receive a second tissue measurement over the period of the pulse indicating the property of the tissue at a second time during the delivery of the pulse of the plurality of pulses of the drive signal, wherein the second time is after the first time;
  determine, prior to completion of the delivery of the pulse, a difference in the property of the tissue between the first time and the second time based on the first and second tissue measurements;
  prior to completion of the first composite load curve, when the difference in the property of the tissue exceeds a difference threshold of the property of the tissue, deliver the drive signal according to a second composite load curve, wherein the second composite load curve defines a second level of power, and wherein the second level of power is greater than the first level of power.

2. The surgical system of claim 1, wherein the property of the tissue is selected from the group consisting of: an impedance of the tissue; a temperature of the tissue; and a pressure exerted on the tissue.

3. The surgical system of claim 1, wherein the property of the tissue is an impedance of the tissue.

4. The surgical system of claim 3, wherein the surgical generator is further programmed to determine the period of the pulse.

5. The surgical system of claim 3, wherein the difference threshold is at least one property selected from the group consisting of: a predetermined impedance value; a percentage of the first tissue measurement; and a multiple of the first tissue measurement.

6. The surgical system of claim 1, further comprising:
  receiving a third tissue measurement indicating the property of the tissue at a third time during delivery of the drive signal;
  receiving a fourth tissue measurement indicating the property of the tissue at a fourth time during delivery of the drive signal; and
  based on the third and fourth tissue measurements, determine a second change in the property between the third time and the fourth time;
  when the second change in the property is greater than a second change threshold, deliver the drive signal according to a third composite load curve, wherein the third composite load curve defines a third level of power, and wherein the third level of power is greater than the second level of power.

7. The surgical system of claim 1, further comprising:
  receiving a third tissue measurement indicating the property of the tissue at a third time during delivery of the drive signal;
  receiving a fourth tissue measurement indicating the property of the tissue at a fourth time during delivery of the drive signal; and
  based on the third and fourth tissue measurements, determine a second change in the property between the third time and the fourth time;
  when the second change in the property is not greater than a second difference threshold, continue to deliver the drive signal according to the second composite load curve.

8. The surgical system of claim 7, further comprising, when the second change in the property is not greater than the second difference threshold, continue to deliver the drive signal according to the second composite load curve until a termination of the second composite load curve.

9. The surgical system of claim 1, wherein relative to the first composite load curve, the second composite load curve has a higher delivered power over a range of potential tissue impedances.

10. The surgical system of claim 1, wherein the surgical generator is further programmed to:
  before delivering the drive signal according to the first composite load curve, receive a starting tissue measurement indicating a starting property of the tissue; and
  prior to treatment, select the first composite load curve based on the property of the tissue.

11. A surgical system for providing a drive signal to a surgical device for treating tissue, the surgical system comprising:

a surgical generator, wherein the surgical generator is programmed to:

deliver the drive signal according to a first composite load curve, wherein the first composite load curve defines a first level of power to be delivered to the tissue as a function of at least one measured property of the tissue, and wherein the first composite load curve defines a plurality of pulses to be sequentially applied to the tissue;

receive a first tissue measurement over a period of a pulse of the plurality of pulses of the drive signal indicating a property of the tissue at a first time during the delivery of the pulse of the plurality of pulses of the drive signal;

receive a second tissue measurement over the period of the pulse indicating the property of the drive signal at a second time during the delivery of the pulse of the plurality of pulses of the drive signal, wherein the second time is after the first time;

determine, prior to completion of the delivery of the pulse of the drive signal, a difference in the property of the drive signal between the first time and the second time based on the first and second tissue measurements;

prior to completion of the first composite load curve, when the difference in the property of the drive signal exceeds a difference threshold of the property of the tissue, deliver the drive signal according to a second composite load curve, wherein the second composite load curve defines a second level of power, and wherein the second level of power is greater than the first level of power.

12. The surgical system of claim 11, wherein the property of the drive signal is a power provided to the tissue, and wherein determining a change in the power provided to the tissue between the first time and the second time comprises determining a change in an average power provided to the tissue during a first pulse of the plurality of pulses and an average power provided to the tissue during a second pulse of the plurality of pulses.

13. The surgical system of claim 11, wherein the property of the drive signal is selected from the group consisting of a current of the drive signal, a voltage of the drive signal a reflectivity of the drive signal, and a force applied to the tissue.

14. A method of providing a drive signal to a surgical device for treating tissue, the method comprising:

delivering the drive signal to a surgical device according to a first composite load curve, wherein the first composite load curve defines a first level of power to be delivered to the tissue as a function of at least one measured property of the tissue, and wherein the first composite load curve defines a plurality of pulses to be sequentially applied to the drive signal;

receiving a first tissue measurement over a period of a pulse of the plurality of pulses of the drive signal indicating a property of the tissue at a first time during the delivery of the pulse of the plurality of pulses of the drive signal;

receiving a second tissue measurement over the period of the pulse indicating the property of the tissue at a second time during the delivery of the pulse of the plurality of pulses of the drive signal, wherein the second time is after the first time;

determining, prior to completion of the delivery of the pulse, a difference in the property of the tissue between the first time and the second time based on the first and second tissue measurements;

prior to completion of the first composite load curve, when the difference in the property of the tissue exceeds a difference threshold of the property of the tissue, delivering the drive signal according to a second composite load curve, wherein the second composite load curve defines a second level of power, and wherein the second level of power is greater than the first level of power.

* * * * *